(12) United States Patent
Clark et al.

(10) Patent No.: US 8,063,013 B2
(45) Date of Patent: Nov. 22, 2011

(54) METHOD OF TREATING GLAUCOMA COMPRISING ADMINISTERING A COMPOSITION COMPRISING HUMAN BMP7

(75) Inventors: Abbot F. Clark, Arlington, TX (US); Robert J. Wordinger, Euless, TX (US)

(73) Assignees: Novartis AG, Basel (CH); University of North Texas Health Science Center, Fort Worth, TX (US)

( * ) Notice: Subject to any disclaimer, the term of this patent is extended or adjusted under 35 U.S.C. 154(b) by 0 days.

(21) Appl. No.: 12/766,056

(22) Filed: Apr. 23, 2010

(65) Prior Publication Data

US 2010/0204086 A1     Aug. 12, 2010

Related U.S. Application Data

(60) Division of application No. 12/106,653, filed on Apr. 21, 2008, now Pat. No. 7,744,873, which is a continuation of application No. 10/286,152, filed on Oct. 31, 2002, now Pat. No. 7,405,192.

(60) Provisional application No. 60/334,852, filed on Oct. 31, 2001.

(51) Int. Cl.
*A61K 38/00* (2006.01)

(52) U.S. Cl. ........................................ 514/1.1; 530/350

(58) Field of Classification Search ........................ None
See application file for complete search history.

(56) References Cited

U.S. PATENT DOCUMENTS

| | | | |
|---|---|---|---|
| 5,145,871 | A | 9/1992 | Cavazza |
| 5,364,884 | A | 11/1994 | Varma et al. |
| 6,207,450 | B1 | 3/2001 | Sheffield et al. |
| 6,248,571 | B1 | 6/2001 | Schmidt et al. |
| 6,248,867 | B1 | 6/2001 | Nguyen et al. |
| 6,613,563 | B1 | 9/2003 | Sosnowski et al. |
| 2008/0194515 | A1 | 8/2008 | Kimko et al. |

FOREIGN PATENT DOCUMENTS

| | | |
|---|---|---|
| WO | 9820889 | 5/1998 |
| WO | 0061774 | 10/2000 |
| WO | 0068247 | 11/2000 |
| WO | 0077021 | 12/2000 |
| WO | 02077006 | 10/2002 |
| WO | 02085909 | 10/2002 |

OTHER PUBLICATIONS

Fuchshofer et al., Invest Ophthalmol. Vis Sci. 48: 715-726, 2007.*
Fuchshofer et al., Exp. Eye Res. 88: 1020-1032, 2009.*
Miyazono, "Positive and negative regulation of TGF-b signaling", J. Cell Science, 113:1101-1109 (2000).
Mohan, et al., "Bone morphogenic proteins 2 and 4 and their receptors in the adults human cornea," Invest. Ophthalmol. & Vis. Sci. 39(13):2626-2636 (1998).
Morrison JC, et al., "Optic nerve head extracellular matrix in primary optic atrophy and experimental glaucoma," Arch. Ophthalmol. 108:1020-1024 (1990).
Murphy, M., et al., "Suppression Subtractive Hybridization Identified High Glucose Levels as a Stimulus for Expression of Connective Tissue Growth Factor and Other Genes in Human Mesangial Cells", J. Biol. Chem. 274(9):5830-5834 (1999).
Nickel et al., "The Crystal Structure of the BMP-2:BMPR-IA Complex and the Generation of BMP-2 Antagonists", J Bone & Joint Surgery 83-A(suppl 1):S1-7—S1-14 (2001).
Nohno, T., et al., "Identification of a Human Type II Receptor for Bone Morphogenetic Protein-4 That Forms Differential Heteromeric Complexes with Bone Morphogenetic Protein Type I Receptors", J. Biol. Chem. 270(38):22522-22526 (1995).
Nonner et al., "Bone morphogenic proteins (BMP6 and BMP7) enhance the protective effect of neurotrophins on cultured septal cholinergic neurons during hypoglycemia," Journal of Neurochemistry 77:691-699 (2001).
Oakley et al., "The Human Glucocorticoid Receptor β Isoform", J. Biol. Chem. 271(16):9550-9559 (1996).
Oakley et al., "Expression and Subcellular Distribution of the β-Isoform of the Human Glucocorticoid Receptor", Endocrinology 138(11):5028-5038 (1997).
Obata et al., "Expression of transforming growth factor-beta superfamily receptors in rat eyes," Acta. Ophthalmol. Scand. 77:151-156 (1999).
Pang I-H, et al., "Human ocular perfusion organ culture: a versatile ex vivo model for glaucoma research," J. Glaucoma 9:468-479 (2000).
Pena et al, "Transforming growth factor beta isoforms in human optic nerve heads," Br. J. Ophthalmol. 83:209-218 (1999).
Picht et al, "Transforming growth factor β2 levels in the aqueous humor in different types of glaucoma and the relation to filtering bleb development," Graefes Arch. Clin. Exp. Ophthalmol. 239:199-207 (2001).
Quigley HA, et al., "Retinal ganglion cell death in experimental glaucoma and after axotomy occurs by apoptosis," Invest. Ophthalmol. Vis. Sci. 36(5):774-786 (1995).
Quigley HA, "Neuronal death in glaucoma," Prog. Retin. Eye Res. 18:39-57 (1999).
Quigley HA, et al., "Retrograde axonal transport of BDNF in retinal ganglion cells is blocked by acute IOP elevation in rats," Invest. Ophthalmol. Vis. Sci. 41(11):3460-3466 (2000).
Reddi, "Bone morphonegetic proteins: an unconventional approach to isolation of first mammalian morphogens," Cytokine & Growth Factor Rev. 8(1):11-20 (1997).
Reddi, "Bone morphogenic proteins and skeletal development: the kidney-bone connection," Pediatr Nephrol. 14:598-601 (2000).
Rohen JW, "Why is Intraocular Pressure Elevated in Chronic Simple Glaucoma? Anatomical considerations." Ophthalmology 90:758-765 (1983).
Steely HT, et al., "The effects of dexamethasone on fibronectin expression in cultured human trabecular meshwork cells," Invest. Ophthalmol. Vis. Sci. 33(7): 2242-2250 (1992).
Steely HT, et al., "The Similarity of protein expression in trabecular meshwork and lamina cribrosa: implications for glaucoma," Exp. Eye Res. 70:17-30 (2000).
Stone EM, et al., "Identification of a gene that causes primary open angle glaucoma," Science 275:668-670 (1997).

(Continued)

*Primary Examiner* — Gyan Chandra
(74) *Attorney, Agent, or Firm* — Jason J. Derry

(57) ABSTRACT

The present invention provides methods and kits for diagnosing and treating glaucoma.

1 Claim, 26 Drawing Sheets

OTHER PUBLICATIONS

Strong, N. P., "How optometrists screen for glaucoma: A survey", Ophthal. Physiol. Opt., 12:3-7 (1992).
Ten Dijke, PP, et al., "Activin receptor-like kinases: a novel subclass of cell-surface receptors with predicted serine/threonine kinase activity", Oncogene 8(10):2879-2887 (1993).
Tripathi RC, et al., "Analysis of Human Aqueous Humor for Epidermal Growth Factor," Exp. Eye Res. 53:407-409 (1991).
Tripathi RC, et al., "Detection, quantification, and significance of basic fibroblast growth factor in the aqueous humor of man, cat, dog and pig," Exp. Eye Res. 54:447-454 (1992).
Tripathi RC, et al., "Trabecular cells of the eye express messenger RNA for transforming growth factor-beta 1 and secrete this cytokine," Invest. Ophthalmol. Vis. Sci. 34(8):2562-2569 (1993).
Tripathi RC, et al., "Aqueous Humor in Glaucomatous Eyes Contains an Increased Level of TFG-β2," Exp. Eye Res. 59:723-727 (1994).
Tripathi RC, et al., "Immunolocalization of bFGF in the Trabecular Meshwork and Detection of its mRNA in Trabecular Cells," Exp. Eye Res. 58:503-507 (1994).
Tripathi RC, et al., "Trabecular Cells Express the TFG-β2 Gene and Secrete the Cytokine," Exp. Eye Res. 58:523-528 (1994).
Tripathi RC, et al., "Clinical implications of aqueous humor growth factors in glaucoma," in Ritch R., Shields, M.B., Krupin, T. (eds). The Glaucomas, 2nd ed. St Louis: Mosby-Year; pp. 71-87 (1996).
Trousse F et al., "BMP4 mediates apoptotic cell death in the developing chick eye," J. Neurosci. 21(4):1292-1301 (2001).
Tuck MW, et al., "Relative effectiveness of different modes of glaucoma screening in optometric practice", Ophthal. Physiol. Opt., 13:227-232 (1993).
Varma R and Minckler D, "Anatomy and pathophysiology of the retina and optic nerve." in Ritch R., Shields, M.B., Krupin, T. (eds). The Glaucomas, 2nd ed. St Louis: Mosby-Year; pp. 139-175 (1996).
Vaughan, D. et al., In: General Ophthalmology, Appleton & Lange, Norwalk, Conn., pp. 213-230 (1992).
Vernon, SA, "Intra-Eye Pressure Range and Pulse Profiles in Normals With the Pulsair Non-Contact Tonometer", Eye 7:134-137 (1993).
von Bubnoff A and Cho KW, "Intracellular BMP signaling regulation in vertebrates: pathway or network?" Dev. Biol. 239:1-14 (2001).
Wang W-H, et al., "Optimal procedure for extracting RNA from human ocular tissues and expression profiling of the congenital glaucoma gene FOXC1 using quantitative RT-PCR," Molecular Vision 7:89-94 (2001).
Wilson K, et al., "Dexamethasone induced ultrastructural changes in cultured human trabecular meshwork cells," Current Eye Research 12(9):783-793 (1993).
Wordinger RJ, et al., "Cultured human trabecular meshwork cells express functional growth factor receptors," Invest. Ophthalmol. & Vis. Sci. 39(9): 1575-1589 (1998).
Dermer, G; "Another anniversary for the war on cancer" ; Bio/Technology; 12:320 (1994).
Liu Y, et al.; The effect of bone morphogenic protein-7 (BMP-7) on functional recovery, local cerebral glucose utilization and blood flow after transient focal cerebral ischemia in rats; Brain Res.; 905:81-90 (2001).
Nishimura, et al.; The forkhead transcription factor gene FKHL7 is responsible for glaucoma phenotypes which map to 6p25; Nature Gen.; 19:140-147; (1998).
Strachan, et al.; Molecular pathology; Human Molecular Genetics; Chapter 15; pp. 401-426; (1996).
Taniguchi, et al.; Clinical phenotype of a Japanese family with primary open angle glaucoma caused by a Pro370Leu mutation in the MYOC/TIGR Gene; Japan J. Ophthalmol; 43:80-84 (1999).
Tripathi RC, et al. Trabecular cells express receptors that bind TGF-beta and TGF-beta 2: a qualitative and quantitative characterization; Invest. Ophthalmol. Vis. Sci; 34(1):260-263 (1993b).
Wordinger et al.; The expression of ciliary neurotrophic factor (CNTF), glial derived neurotrophic factor (GDNF) and their receptors by human trabecular meshwork (TM); Cells and Tissues, IVOS; 40(4):S504 (1999).
Wordinger, RJ, et al.; Expression of alternatively spliced growth factor receptor isoforms in the human trabecular meshwork; Invest. Ophthalmol. Vis. Sci.; 40(1):242-247 (1999).
Wordinger RJ, et al.; Expression of bone morphogenetic proteins (BMP), BMP receptors, and BMP associated proteins in human trabecular meshwork and optic nerve head cells and tissues; Molecular Vision; 8:241-250 (2002).
Wordinger RJ, et al.; Human trabecular meshwork cells secrete neurotrophins and express neurotrophin receptors (Trk),; Invest. Ophthalmol. & Vis. Sci.; 41:3833-3841; (2000).
Yamashita et al., "Bone morphogenic protein receptors," Bone 19:569-574 (1996).
You et al., "Bone morphogenic proteins and growth and differentiation factors in the human cornea," Invest. Ophthalmol. & Vis. Sci. 40(2):296-311 (1999).
Zhang et al., "Development of bone morphogenetic protein receptors in the nervous system and possible roles in regulating trkC expression," J. Neurosci. 18:3314-3326 (1998).
NCBI Entrez database nucleotide sequences, National Center for Biotechnology Information, National Library of Medicine, NIH (Bethesda, MD, USA) Accession No. M19481, Apr. 27, 1993 [D18].
NCBI Entrez database nucleotide sequences, National Center for Biotechnology Information, National Library of Medicine, NIH (Bethesda, MD, USA) Accession No. Z22535, Sep. 29, 1993 [D13].
NCBI Entrez database nucleotide sequences, National Center for Biotechnology Information, National Library of Medicine, NIH (Bethesda, MD, USA) Accession No. M22849, Oct. 31, 1994 [D9].
NCBI Entrez database nucleotide sequences, National Center for Biotechnology Information, National Library of Medicine, NIH (Bethesda, MD, USA) Accession No. X51801, Mar. 23, 1995 [D12].
NCBI Entrez database nucleotide sequences, National Center for Biotechnology Information, National Library of Medicine, NIH (Bethesda, MD, USA) Accession No. U31202, Dec. 13, 1995 [D19].
NCBI Entrez database nucleotide sequences, National Center for Biotechnology Information, National Library of Medicine, NIH (Bethesda, MD, USA) Accession No. X98494, Jul. 9, 1997 [D8].
NCBI Entrez database nucleotide sequences, National Center for Biotechnology Information, National Library of Medicine, NIH (Bethesda, MD, USA) Accession No. AF090189, Mar. 12, 1999 [D20].
NCBI Entrez database nucleotide sequences, National Center for Biotechnology Information, National Library of Medicine, NIH (Bethesda, MD, USA) Accession No. M60314, Dec. 22, 1999 [D11].
NCBI Entrez database nucleotide sequences, National Center for Biotechnology Information, National Library of Medicine, NIH (Bethesda, MD, USA) Accession No. U89326, Feb. 28, 2000 [D14].
NCBI Entrez database nucleotide sequences, National Center for Biotechnology Information, National Library of Medicine, NIH (Bethesda, MD, USA) Accession No. AF110137, Jul. 27, 2000 [D17].
NCBI Entrez database nucleotide sequences, National Center for Biotechnology Information, National Library of Medicine, NIH (Bethesda, MD, USA) Accession No. NM_001204, Oct. 31, 2000 [D15].
NCBI Entrez database nucleotide sequences, National Center for Biotechnology Information, National Library of Medicine, NIH (Bethesda, MD, USA) Accession No. NM_001202, Oct. 31, 2000 [D10].
NCBI Entrez database nucleotide sequences, National Center for Biotechnology Information, National Library of Medicine, NIH (Bethesda, MD, USA) Accession No. AF209930, Aug. 3, 2001 [D16].
Lappin et al.; "Gremlin: an example of the re-emergence of developmental programmes in diabetic nephropathy"; Nephrol Dial Transplant; Supplement 9; vol. 17; pp. 65-67 (2002).
Stabile et al.; "Bone morphogenic protein antagonist Drm/gremlin is a novel proangiogenic factor"; Chemokines, Cytokines and Interleukins; The American Society of Hematology; Blood; vol. 109, No. 5, pp. 1834-1840 (Mar. 1, 2007).
Agarwal et al., "Expression of Transforming Growth Factor Beta Isoforms (TGF-β 1-3) And Receptors (TGFβ RI-RIII) in Cultured Human Trabecular Meshwork Cells", IOVS 38(4):S563 (1997).
Agarwal R, et al., "FAS-activated apoptosis and other apoptosis mediators in human trabecular meshwork cells," Exp. Eye Res. 68:583-590 (1999).
Agarwal et al., "The Expression of Bone Morphogenetic Protein (BMP) and BMP Receptor mRNA by Human Trabecular Meshwork and Optic Nerve Head Cells and Tissues", IOVS 41(4):S506 (2000).

Astrom, A.K., et al., "Chromosomal localization of three human genes encoding bone morphogenetic protein receptors", Mammalian Genome 10(3):299-302 (1999).

Attisano L, Tuen Lee-Hoeflich S, "The Smads," Genome Biol. 2(8) Reviews/3010.1 (2001) 1-8.

Bengtsson B, "Incidence of manifest glaucoma," BR J Ophthalmol, 73:483-487 (1989).

Birren, et al., Genome Analysis, A Laboratory Manual vol. 2 Detecting Genes, (Bruce Birren ed., Cold Spring Harbor Laboratory Press 1998) 287-292.

Chang et al., "Haploinsufficient Bmp4 ocular phenotypes include anterior segment dysgenesis with elevated intraocular pressure", BioMed Central, BMC Genetics, 2:18 (2001).

Chundru et al., "Detection of neurotrophins in human aqueous humor," Invest. Ophthalmol. Vis. Sci. 41(4):S326 (2000).

Clark AF, et al., "Glucocorticoid-induced formation of cross-linked actin networks in cultured human trabecular meshwork cells," Invest. Ophthalmol. & Vis. Sci. 35(1):281-294 (1994).

Clark AF, et al., "Cell biology of the human lamina cribrosa," In Drance SM (ed). Optic Nerve in Glaucoma. Kugler Publications, New York: pp. 79-105 (1995).

Clark AF, et al., "Cytoskeletal changes in cultured human glaucoma trabecular meshwork cells," J. Glaucoma 4:183-188 (1995).

Clark AF, et al., "Dexamethasone-induced ocular hypertension in perfusion-cultured human eyes," Invest. Ophthalmol. & Vis. Sci. 36(2):478-489 (1995).

Clark AF, et al., "Inhibition of dexamethasone-induced cytoskeletal changes in cultured human trabecular meshwork cells by tetrahydrocortisol," Invest. Ophthalmol. & Vis. Sci. 37(5):805-813 (1996).

Clark AF, et al., "Expression of the glaucoma gene myocilin (MYOC) in the human optic nerve head," FASEB J. 15:1251-1253 (2001).

Clark AF, et al., "Glucocorticoid induction of the glaucoma gene MYOC in human and monkey trabecular meshwork cells and tissues," Invest. Ophthalmol. & Vis. Sci. 42(8):1769-1780 (2001).

Cummings, Michael R., Human Heredity, Fourth Edition, (West/Wadsworth 1997) 266-283.

Dickerson JE, et al., "The effect of dexamethasone on integrin and laminin expression in cultured human trabecular meshwork cells," Exp. Eye Res. 66:731-738 (1998).

Dudley et al., "A requirement for bone morphogenic protein-7 during development of the mammalian kidney and eye," Genes & Development 9:2795-2807 (1995).

Elbashir SM, et al., "Duplexes of 21-nucleotide RNAs mediate RNA interference in cultured mammalian cells", Nature 411:494-498, 2001.

Encio et al., "The Genomic Structure of the Human Glucocorticoid Receptor", J. Biol. Chem. 266(11):7182-7188 (1991).

Furuta and Hogan, "BMP4 is essential for lens induction in the mouse embryo," Genes & Dev. 12:3764-3775 (1998).

Giguère et al., "Functional Domains of the Human Glucocorticoid Receptor", Cell 46:645-652 (1986).

Greve, M. et al., "Comparison of the oculokinetic perimetry glaucoma screener with two types of visual filed analyser", Can. J. Ophthamol. 28(5):201-206 (1993).

Grierson I et al., "Characteristics of Meshwork Cells and Age Changes in the Outflow System of the Eye: Their Relevance to Primary Open Angle Glaucoma." in Mills KB (ed). Glaucoma. Proceedings of the Fourth International Symposium of the Northern Eye Institute, Manchester, UK, New York, Pergamon: pp. 12-31 (1988).

Gutteridge, "Normal tension glaucoma: diagnostic features and comparison with primary open angle glaucoma"; Clinical and Exp. Optometry; 83: 161-172 (2000).

Hernandez M and Gong H, "Extracellular matrix of the trabecular meshwork and optic nerve head." in Ritch R., Shields, M.B., Krupin, T. (eds). The Glaucomas, 2nd ed. St Louis: Mosby-Year; pp. 213-249 (1996).

Hernandez, et al., "Changes in the Extracellular Matrix of the Human Optic Nerve Head in Primary Open-Angle Glaucoma," Am. J. Ophthalmol. 109:180-188 (1990).

Hernandez MR and Pena JD, "The optic nerve head in glaucomatous optic neuropathy," Arch Ophthalmol. 115:389-395 (1997).

Hitchings RA, "Glaucoma screening", Br. J. Ophthamol. 77:326 (1993).

Jain, R.; "Vascular and interstitial barriers to delivery of therapeutic agents in tumors"; Cancer and Metastasis Reviews; 9; 253-266 (1990).

Liu X., et al.; Human trabecular meshwork cells express the ciliary neurotrophic factor (CNTF) tripartate receptor complex; Exp. Eye Res.; 72:711-717 (2001).

Hogan BL, "Bone morphogenic proteins: multifunctional regulators of vertebrate development," Genes Dev. 10:1580-1594 (1996).

Hollenberg et al., "Primary Structure and Expression of a Functional Human Glucocorticoid Receptor cDNA", Nature 318(19):635-641 (1985).

Hu and Ritch, "Hepatocyte Growth Factor is Increased in the Aqueous Humor of Glaucomatous Eyes," J. Glaucoma 10:152-157 (2001).

Inatani et al., "Transforming growth factor β2 levels in aqueous humor of glaucomatous eyes," Graefes Arch. Clin. Exp. Ophthalmol. 239:109-113 (2001).

Itoh et al., "Signaling of transforming growth factor-β family members through Smad proteins", Eur. J. Biochem. 267:6954-6967 (2000).

Jacobson N, et al., "Non-secretion of mutant proteins of the glaucoma gene myocilin in cultured trabecular meshwork cells and in aqueous humor," Human Molecular Genetics 10(2):117-125 (2001).

Jena et al., "BMP7 null mutation in mice: developmental defects in skeleton, kidney, and eye," Exp. Cell Res. 230:28-37 (1997).

Jorde, et al., Medical Genetics, Second Edition, (Mosby 1999) 29-57.

Kawabata et al., "Signal Transduction by Bone Morphogenetic Proteins", Cytokine & Growth Factor Reviews, vol. 9, No. 1, 49-61 (1998).

Kerrigan et al., "Tunel-positive ganglion cells in human primary open-angle glaucoma," Arch. Ophthalmol. 115:1031-1035 (1997).

Lambert et al., "Expression of TGF-Beta Isoforms and Their Receptor mRNA'S in Cultured Human Lamina Cribrosa Cells", IOVS 38(4):S162 (1997).

Lambert, et al. "Map Kinase Activation and Cell Proliferation of Cultured Lamina Cribrosa Cells Following Exogenous NGF Treatment", IOVS 41(4):S827 (2000).

Lambert W, et al., "Neurotrophin and neurotrophin receptor expression by cells from the human lamina cribrosa," Invest. Ophthalmol. Vis. Sci., 42(10):2315-2323 (2001).

Leske MC, et al., "The Epidemiology of Open-Angle Glaucoma: A Review", American Journal of Epidemilogy, 118(2):166-191 (1983).

Liu et al., "Expression of Ciliary Neurotrophic Factor (CNTF), Glial Derived Neurotrophic Factor (GDNF) And Their Receptors by Cells of the Human Optic Nerve Head", IOVS 40(4):S673 (1999).

Luo et al., "BMP-7 is an inducer of nephrogenesis, and is also required for eye development and skeletal patterning," Genes & Development 9:2808-2820 (1995).

Lütjen-Drecoll E. and Rohen J.W., "Morphology of aqueous outflow pathways in normal and glaucomatous eyes," in Ritch R., Shields, M.B., Krupin, T. (eds). The Glaucomas, 2nd ed. St Louis: Mosby-Year; pp. 89-123 (1996).

McMahon R., et al., "IHG-2, a Mesangial Cell Gene Induced by High Glucose, Is Human gremlin", J. Biol. Chem. 275(14):9901-9904 (2000).

* cited by examiner

FIG. 1a

```
1    ggggacttct tgaacttgca gggagaataa cttGCGCACC CCACTTTGCG CCGGTGCCTT

61   TGCCCCAGCG GAGCCTGCTT CGCCATCTCC GAGCCCCACC GCCCCTCCAC TCCTCGGCCT

121  TGCCCGACAC TGAGACGCTG TTCCCAGCGT GAAAAGAGAG ACTGCGCGGC CGGCACCCGG

181  GAGAAGGAGG AGGCAAAGAA AAGGAACGGA CATTCGGTCC TTGCGCCAGG TCCTTTGACC

241  AGAGTTTTTC CATGTGGACG CTCTTTCAAT GGACGTGTCC CCGCGTGCTT CTTAGACGGA
```

|     |     |     |     |     | THR | MET | VAL | ALA | GLY | THR | ARG | 7 |
|-----|-----|-----|-----|-----|-----|-----|-----|-----|-----|-----|-----|---|
| 301 | CTGCGGTCTC | | CTAAAGGTCG | ACC | ATG | GTG | GCC | GGG | ACC | CGC | |

|     | CYS | LEU | LEU | ALA | LEU | LEU | LEU | PRO | GLN | VAL | LEU | 18 |
|-----|-----|-----|-----|-----|-----|-----|-----|-----|-----|-----|-----|----|
| 342 | TGT | CTT | CTA | GCG | TTG | CTG | CTT | CCC | CAG | GTC | CTC | |

|     | LEU | GLY | GLY | ALA | ALA | GLY | LEU | VAL | PRO | GLU | LEU | 29 |
|-----|-----|-----|-----|-----|-----|-----|-----|-----|-----|-----|-----|----|
| 375 | CTG | GGC | GGC | GCG | GCT | GGC | CTC | GTT | CCG | GAG | CTG | |

|     | GLY | ARG | ARG | LYS | PHE | ALA | ALA | ALA | SER | SER | GLY | 40 |
|-----|-----|-----|-----|-----|-----|-----|-----|-----|-----|-----|-----|----|
| 408 | GGC | CGC | AGG | AAG | TTC | GCG | GCG | GCG | TCG | TCG | GGC | |

|     | ARG | PRO | SER | SER | GLN | PRO | SER | ASP | GLU | VAL | LEU | 51 |
|-----|-----|-----|-----|-----|-----|-----|-----|-----|-----|-----|-----|----|
| 441 | CGC | CCC | TCA | TCC | CAG | CCC | TCT | GAC | GAG | GTC | CTG | |

|     | SER | GLU | PHE | GLU | LEU | ARG | LEU | LEU | SER | MET | PHE | 62 |
|-----|-----|-----|-----|-----|-----|-----|-----|-----|-----|-----|-----|----|
| 474 | AGC | GAG | TTC | GAG | TTG | CGG | CTG | CTC | AGC | ATG | TTC | |

|     | GLY | LEU | LYS | GLN | ARG | PRO | THR | PRO | SER | ARG | ASP | 73 |
|-----|-----|-----|-----|-----|-----|-----|-----|-----|-----|-----|-----|----|
| 507 | GGC | CTG | AAA | CAG | AGA | CCC | ACC | CCC | AGC | AGG | GAC | |

|     | ALA | VAL | VAL | PRO | PRO | TYR | MET | LEU | ASP | LEU | TYR | 84 |
|-----|-----|-----|-----|-----|-----|-----|-----|-----|-----|-----|-----|----|
| 540 | GCC | GTG | GTG | CCC | CCC | TAC | ATG | CTA | GAC | CTG | TAT | |

|     | ARG | ARG | HIS | SER | GLY | GLN | PRO | GLY | SER | PRO | ALA | 95 |
|-----|-----|-----|-----|-----|-----|-----|-----|-----|-----|-----|-----|----|
| 573 | CGC | AGG | CAC | TCA | GGT | CAG | CCG | GGC | TCA | CCC | GCC | |

|     | PRO | ASP | HIS | ARG | LEU | GLU | ARG | ALA | ALA | SER | ARG | 106 |
|-----|-----|-----|-----|-----|-----|-----|-----|-----|-----|-----|-----|-----|
| 606 | CCA | GAC | CAC | CGG | TTG | GAG | AGG | GCA | GCC | AGC | CGA | |

|     | LA  | ASN | THR | VAL | ARG | SER | PHE | HIS | HIS | GLU | GLU | 117 |
|-----|-----|-----|-----|-----|-----|-----|-----|-----|-----|-----|-----|-----|
| 639 | GCC | AAC | ACT | GTG | CGC | AGC | TTC | CAC | CAT | GAA | GAA | |

FIG. 1b

|     |     |     |     |     |     |     |     |     |     |     |     |
|-----|-----|-----|-----|-----|-----|-----|-----|-----|-----|-----|-----|
|     | SER | LEU | GLU | GLU | LEU | PRO | GLU | THR | SER | GLY | LYS | 128 |
| 672 | TCT | TTG | GAA | GAA | CTA | CCA | GAA | ACG | AGT | GGG | AAA |     |
|     | THR | THR | ARG | ARG | PHE | PHE | PHE | ASN | LEU | SER | SER | 139 |
| 705 | ACA | ACC | CGG | AGA | TTC | TTC | TTT | AAT | TTA | AGT | TCT |     |
|     | ILE | PRO | THR | GLU | GLU | PHE | ILE | THR | SER | ALA | GLU | 150 |
| 738 | ATC | CCC | ACG | GAG | GAG | TTT | ATC | ACC | TCA | GCA | GAG |     |
|     | LEU | GLN | VAL | PHE | ARG | GLU | GLN | MET | GLN | ASP | ALA | 161 |
| 771 | CTT | CAG | GTT | TTC | CGA | GAA | CAG | ATG | CAA | GAT | GCT |     |
|     | LEU | GLY | ASN | ASN | SER | SER | PHE | HIS | HIS | ARG | ILE | 172 |
| 804 | TTA | GGA | AAC | AAT | AGC | AGT | TTC | CAT | CAC | CGA | ATT |     |
|     | ASN | ILE | TYR | GLU | ILE | ILE | LYS | PRO | ALA | THR | ALA | 183 |
| 837 | AAT | ATT | TAT | GAA | ATC | ATA | AAA | CCT | GCA | ACA | GCC |     |
|     | ASN | SER | LYS | PHE | PRO | VAL | THR | ARG | LEU | LEU | ASP | 194 |
| 870 | AAC | TCG | AAA | TTC | CCC | GTG | ACC | AGA | CTT | TTG | GAC |     |
|     | THR | ARG | LEU | VAL | ASN | GLN | ASN | ALA | SER | ARG | TRP | 205 |
| 903 | ACC | AGG | TTG | GTG | AAT | CAG | AAT | GCA | AGC | AGG | TGG |     |
|     | GLU | SER | PHE | ASP | VAL | THR | PRO | ALA | VAL | MET | ARG | 216 |
| 936 | GAA | AGT | TTT | GAT | GTC | ACC | CCC | GCT | GTG | ATG | CGG |     |
|     | TRP | THR | ALA | GLN | GLY | HIS | ALA | ASN | HIS | GLY | PHE | 227 |
| 969 | TGG | ACT | GCA | CAG | GGA | CAC | GCC | AAC | CAT | GGA | TTC |     |
|     | VAL | VAL | GLU | VAL | ALA | HIS | LEU | GLU | GLU | LYS | GLN | 238 |
| 1002| GTG | GTG | GAA | GTG | GCC | CAC | TTG | GAG | GAG | AAA | CAA |     |
|     | GLY | VAL | SER | LYS | ARG | HIS | VAL | ARG | ILE | SER | ARG | 249 |
| 1035| GGT | GTC | TCC | AAG | AGA | CAT | GTT | AGG | ATA | AGC | AGG |     |
|     | SER | LEU | HIS | GLN | ASP | GLU | HIS | SER | TRP | SER | GLN | 260 |
| 1068| TCT | TTG | CAC | CAA | GAT | GAA | CAC | AGC | TGG | TCA | CAG |     |
|     | ILE | ARG | PRO | LEU | LEU | VAL | THR | PHE | GLY | HIS | ASP | 271 |
| 1101| ATA | AGG | CCA | TTG | CTA | GTA | ACT | TTT | GGC | CAT | GAT |     |
|     | GLY | LYS | GLY | HIS | PRO | LEU | HIS | LYS | ARG | GLU | LYS | 282 |
| 1134| GGA | AAA | GGG | CAT | CCT | CTC | CAC | AAA | AGA | GAA | AAA |     |

FIG. 1c

```
           ARG  GLN  ALA  LYS  HIS  LYS  GLN  ARG  LYS  ARG  LEU    293
1167       CGT  CAA  GCC  AAA  CAC  AAA  CAG  CGG  AAA  CGC  CTT

LYS  SER  SER  CYS  LYS  ARG  HIS  PRO  LEU  TYR  VAL    304
1200       AAG  TCC  AGC  TGT  AAG  AGA  CAC  CCT  TTG  TAC  GTG

ASP  PHE  SER  ASP  VAL  GLY  TRP  ASN  ASP  TRP  ILE    315
1233       GAC  TTC  AGT  GAC  GTG  GGG  TGG  AAT  GAC  TGG  ATT

VAL  ALA  PRO  PRO  GLY  TYR  HIS  ALA  PHE  TYR  CYS    326
1266       GTG  GCT  CCC  CCG  GGG  TAT  CAC  GCC  TTT  TAC  TGC

HIS  GLY  GLU  CYS  PRO  PHE  PRO  LEU  ALA  ASP  HIS    337
1299       CAC  GGA  GAA  TGC  CCT  TTT  CCT  CTG  GCT  GAT  CAT

LEU  ASN  SER  THR  ASN  HIS  ALA  ILE  VAL  GLN  THR    348
1332       CTG  AAC  TCC  ACT  AAT  CAT  GCC  ATT  GTT  CAG  ACG

LEU  VAL  ASN  SER  VAL  ASN  SER  LYS  ILE  PRO  LYS    359
1365       TTG  GTC  AAC  TCT  GTT  AAC  TCT  AAG  ATT  CCT  AAG

ALA  CYS  CYS  VAL  PRO  THR  GLU  LEU  SER  ALA  ILE    370
1398       GCA  TGC  TGT  GTC  CCG  ACA  GAA  CTC  AGT  GCT  ATC

SER  MET  LEU  TYR  LEU  ASP  GLU  ASN  GLU  LYS  VAL    381
1431       TCG  ATG  CTG  TAC  CTT  GAC  GAG  AAT  GAA  AAG  GTT

VAL  LEU  LYS  ASN  TYR  GLN  ASP  MET  VAL  VAL  GLU    392
1464       GTA  TTA  AAG  AAC  TAT  CAG  GAC  ATG  GTT  GTG  GAG

GLY  CYS  GLY  CYS  ARG                                  397
1497       GGT  TGT  GGG  TGT  CGC

1512       TAG  TACAGCAAAATTAAATACATAAATATATATA
```

FIG. 2a

```
1    GAAAGCGAGG GAGGGAAAGA GGAGGAAGGA AGATGCGAGA AGGCAGAGGA GGAGGGAGGG

61   AGGGAAGGAG CGCGGAGCCC GGCCCGGAAG CTAGGTGAGT GTGGCATCCG AGCTGAGGGA

121  CGCGAGCCTG AGACGCCGCT GCTGCTCCGG CTGAGTATCT AGCTTGTCTC CCCGATGGGA

181  TTCCCGTCCA AGCTATCTCG AGCCTGCAGC GCCACAGTCC CCGGCCCTCG CCCAGGTTCA

241  CTGCAACCGT TCAGAGGTCC CCAGGAGCTG CTGCTGGCGA GCCCGCTACT GCAGGGACCT

301  ATGGAGCCAT TCCGTAGTGC CATCCCGAGC AACGCACTGC TGCAGCTTCC CTGAGCCTTT

361  CCAGCAAGTT TGTTCAAGAT TGGCTGTCAA GAATCATGGA CTGTTATTAT ATGCCTTGTT
```

|     |            |       | Met | Ile | Pro | Gly | Asn | Arg | Met | Leu | 8   |
|-----|------------|-------|-----|-----|-----|-----|-----|-----|-----|-----|-----|
| 421 | TTCTGTCAAG | ACACC | ATG | ATT | CCT | GGT | AAC | CGA | ATG | CTG |     |

|     | Met | Val | Val | Leu | Leu | Cys | Gln | Val | Leu | Leu | Gly | 19 |
|-----|-----|-----|-----|-----|-----|-----|-----|-----|-----|-----|-----|----|
| 460 | ATG | GTC | GTT | TTA | TTA | TGC | CAA | GTC | CTG | CTA | GGA |    |

|     | Gly | Ala | Ser | His | Ala | Ser | Leu | Ile | Pro | Glu | Thr | 30 |
|-----|-----|-----|-----|-----|-----|-----|-----|-----|-----|-----|-----|----|
| 493 | GGC | GCG | AGC | CAT | GCT | AGT | TTG | ATA | CCT | GAG | ACG |    |

|     | Gly | Lys | Lys | Lys | Val | Ala | Glu | Ile | Gln | Gly | His | 41 |
|-----|-----|-----|-----|-----|-----|-----|-----|-----|-----|-----|-----|----|
| 526 | GGG | AAG | AAA | AAA | GTC | GCC | GAG | ATT | CAG | GGC | CAC |    |

|     | Ala | Gly | Gly | Arg | Arg | Ser | Gly | Gln | Ser | His | Glu | 52 |
|-----|-----|-----|-----|-----|-----|-----|-----|-----|-----|-----|-----|----|
| 559 | GCG | GGA | GGA | CGC | CGC | TCA | GGG | CAG | AGC | CAT | GAG |    |

|     | Leu | Leu | Arg | Asp | Phe | Glu | Ala | Thr | Leu | Leu | Gln | 63 |
|-----|-----|-----|-----|-----|-----|-----|-----|-----|-----|-----|-----|----|
| 592 | CTC | CTG | CGG | GAC | TTC | GAG | GCG | ACA | CTT | CTG | CAG |    |

|     | Met | Phe | Gly | Leu | Arg | Arg | Arg | Pro | Gln | Pro | Ser | 74 |
|-----|-----|-----|-----|-----|-----|-----|-----|-----|-----|-----|-----|----|
| 625 | ATG | TTT | GGG | CTG | CGC | CGC | CGC | CCG | CAG | CCT | AGC |    |

|     | Lys | Ser | Ala | Val | Ile | Pro | Asp | Tyr | Met | Arg | Asp | 85 |
|-----|-----|-----|-----|-----|-----|-----|-----|-----|-----|-----|-----|----|
| 658 | AAG | AGT | GCC | GTC | ATT | CCG | GAC | TAC | ATG | CGG | GAT |    |

|     | Leu | Tyr | Arg | Leu | Gln | Ser | Gly | Glu | Glu | Glu | Glu | 96 |
|-----|-----|-----|-----|-----|-----|-----|-----|-----|-----|-----|-----|----|
| 691 | CTT | TAC | CGG | CTT | CAG | TCT | GGG | GAG | GAG | GAG | GAA |    |

|     | Glu | Gln | Ile | His | Ser | Thr | Gly | Leu | Glu | Tyr | Pro | 107 |
|-----|-----|-----|-----|-----|-----|-----|-----|-----|-----|-----|-----|-----|
| 724 | GAG | CAG | ATC | CAC | AGC | ACT | GGT | CTT | GAG | TAT | CCT |     |

FIG. 2b

| | | | | | | | | | | | |
|---|---|---|---|---|---|---|---|---|---|---|---|
| 757 | Glu GAG | Arg CGC | Pro CCG | Ala GCC | Ser AGC | Arg CGG | Ala GCC | Asn AAC | Thr ACC | Val GTG | Arg AGG | 118 |
| 790 | Ser AGC | Phe TTC | His CAC | His CAC | Glu GAA | Glu GAA | His CAT | Leu CTG | Glu GAG | Asn AAC | Ile ATC | 129 |
| 823 | Pro CCA | Gly GGG | Thr ACC | Ser AGT | Glu GAA | Asn AAC | Ser TCT | Ala GCT | Phe TTT | Arg CGT | Phe TTC | 140 |
| 856 | Leu CTC | Phe TTT | Asn AAC | Leu CTC | Ser AGC | Ser AGC | Ile ATC | Pro CCT | Glu GAG | Asn AAC | Glu GAG | 151 |
| 889 | Ala GCG | Ile ATC | Ser TCC | Ser TCT | Ala GCA | Glu GAG | Leu CTT | Arg CGG | Leu CTC | Phe TTC | Arg CGG | 162 |
| 922 | Glu GAG | Gln CAG | Val GTG | Asp GAC | Gln CAG | Gly GGC | Pro CCT | Asp GAT | Trp TGG | Glu GAA | Arg AGG | 173 |
| 955 | Gly GGC | Phe TTC | His CAC | Arg CGT | Ile ATA | Asn AAC | Ile ATT | Tyr TAT | Glu GAG | Val GTT | Met ATG | 184 |
| 988 | Lys AAG | Pro CCC | Pro CCA | Ala GCA | Glu GAA | Val GTG | Val GTG | Pro CCT | Gly GGG | His CAC | Leu CTC | 195 |
| 1021 | Ile ATC | Thr ACA | Arg CGA | Leu CTA | Leu CTG | Asp GAC | Thr ACG | Arg AGA | Leu CTG | Val GTC | His CAC | 206 |
| 1054 | His CAC | Asn AAT | Val GTG | Thr ACA | Arg CGG | Trp TGG | Glu GAA | Thr ACT | Phe TTT | Asp GAT | Val GTG | 217 |
| 1087 | Ser AGC | Pro CCT | Ala GCG | Val GTC | Leu CTT | Arg CGC | Trp TGG | Thr ACC | Arg CGG | Glu GAG | Lys AAG | 228 |
| 1120 | Gln CAG | Pro CCA | Asn AAC | Tyr TAT | Gly GGG | Leu CTA | Ala GCC | Ile ATT | Glu GAG | Val GTG | Thr ACT | 239 |
| 1153 | His CAC | Leu CTC | His CAT | Gln CAG | Thr ACT | Arg CGG | Thr ACC | His CAC | Gln CAG | Gly GGC | Gln CAG | 250 |
| 1186 | His CAT | Val GTC | Arg AGG | Ile ATT | Ser AGC | Arg CGA | Ser TCG | Leu TTA | Pro CCT | Gln CAA | Gly GGG | 261 |
| 1219 | Ser AGT | Gly GGG | Asn AAT | Trp TGG | Ala GCC | Gln CAG | Leu CTC | Arg CGG | Pro CCC | Leu CTC | Leu CTG | 272 |

FIG. 2c

```
           Val  Thr  Phe  Gly  His  Asp  Gly  Arg  Gly  His  Ala   283
    1252   GTC  ACC  TTT  GGC  CAT  GAT  GGC  CGG  GGC  CAT  GCC

Leu  Thr  Arg  Arg  Arg  Arg  Ala  Lys  Arg  Ser  Pro   294
    1285   TTG  ACC  CGA  CGC  CGG  AGG  GCC  AAG  CGT  AGC  CCT

Lys  His  His  Ser  Gln  Arg  Ala  Arg  Lys  Lys  Asn   305
    1318   AAG  CAT  CAC  TCA  CAG  CGG  GCC  AGG  AAG  AAG  AAT

Lys  Asn  Cys  Arg  Arg  His  Ser  Leu  Tyr  Val  Asp   316
    1351   AAG  AAC  TGC  CGG  CGC  CAC  TCG  CTC  TAT  GTG  GAC

Phe  Ser  Asp  Val  Gly  Trp  Asn  Asp  Trp  Ile  Val   327
    1384   TTC  AGC  GAT  GTG  GGC  TGG  AAT  GAC  TGG  ATT  GTG

Ala  Pro  Pro  Gly  Tyr  Gln  Ala  Phe  Tyr  Cys  His   338
    1417   GCC  CCA  CCA  GGC  TAC  CAG  GCC  TTC  TAC  TGC  CAT

Gly  Asp  Cys  Pro  Phe  Pro  Leu  Ala  Asp  His  Leu   349
    1450   GGG  GAC  TGC  CCC  TTT  CCA  CTG  GCT  GAC  CAC  CTC

Asn  Ser  Thr  Asn  His  Ala  Ile  Val  Gln  Thr  Leu   360
    1483   AAC  TCA  ACC  AAC  CAT  GCC  ATT  GTG  CAG  ACC  CTG

Val  Asn  Ser  Val  Asn  Ser  Ser  Ile  Pro  Lys  Ala   371
    1516   GTC  AAT  TCT  GTC  AAT  TCC  AGT  ATC  CCC  AAA  GCC

Cys  Cys  Val  Pro  Thr  Glu  Leu  Ser  Ala  Ile  Ser   382
    1549   TGT  TGT  GTG  CCC  ACT  GAA  CTG  AGT  GCC  ATC  TCC

Met  Leu  Tyr  Leu  Asp  Glu  Tyr  Asp  Lys  Val  Val   393
    1582   ATG  CTG  TAC  CTG  GAT  GAG  TAT  GAT  AAG  GTG  GTA

Leu  Lys  Asn  Tyr  Gln  Glu  Met  Val  Val  Ala  Gly   404
    1615   CTG  AAA  AAT  TAT  CAG  GAG  ATG  GTA  GTA  GAG  GGA

Cys  Gly  Cys  Arg                                       408
    1648   TGT  GGG  TGC  CGC  TGA  GATCAGGCAGTCCTTGAGGATAGACAGATATAC

1696   ACACCACACACACACACCACATACACCACACACACACGTTCCCATCCACTCACCCACACACTA

1759   CACAGACTGCTTCCTTATAGCTGGACTTTTATTTAAAAAAAAAAAAAAAAAAAATGGAAAAAAT
```

FIG. 2d

1822 CCCTAAACATTCACCTTGACCTTATTTATGACTTTACGTGCAAATGTTTTGACCATATTGATC

1885 ATATATTTTGACAAAATATATTTATAACTACGTATTAAAAGAAAAAAATAAAATGAGTCATT

FIG. 3a

```
1    CTGGTATATT TGTGCCTGCT GGAGGTGGAA TTAACAGTAA GAAGGAGAAA GGGATTGAAT
61   GGACTTACAG GAAGGATTTC AAGTAAATTC AGGGAAACAC ATTTACTTGA ATAGTACAAC
121  CTAGAGTATT ATTTTACACT AAGACGACAC AAAAGATGTT AAAGTTATCA CCAAGCTGCC
181  GGACAGATAT ATATTCCAAC ACCAAGGTGC AGATCAGCAT AGATCTGTGA TTCAGAAATC
241  AGGATTTGTT TTGGAAAGAG CTCAAGGGTT GAGAAGAACT CAAAAGCAAG TGAAGATTAC
301  TTTGGGAACT ACAGTTTATC AGAAGATCAA CTTTTGCTAA TTCAAATACC AAAGGCCTGA
361  TTATCATAAA TTCATATAGG AATGCATAGG TCATCTGATC AAATAATATT AGCCGTCTTC
421  TGCTACATCA ATGCAGCAAA AACTCTTAAC AACTGTGGAT AATTGGAAAT CTGAGTTTCA
481  GCTTTCTTAG AAATAACTAC TCTTGACATA TTCCAAAATA TTTAAAATAG GACAGGAAAA
541  TCGGTGAGGA TGTTGTGCTC AGAAATGTCA CTGTCATGAA AAATAGGTAA ATTTGTTTTT
601  TCAGCTACTG GGAAACTGTA CCTCCTAGAA CCTTAGGTTT TTTTTTTTTT AAGAGGACAA
```

|       |      |      |      |      |      |      |      | Met | His | Leu | Thr | 4  |
|-------|------|------|------|------|------|------|------|-----|-----|-----|-----|----|
| 661   | GAAGGACTAA AAATATCAAC TTTTGCTTTT GGACAAAA |      |      |      |      |      |      | ATG | CAT | CTG | ACT |    |

|     | Val | Phe | Leu | Leu | Lys | Gly | Ile | Val | Gly | Phe | Leu | 15 |
|-----|-----|-----|-----|-----|-----|-----|-----|-----|-----|-----|-----|----|
| 711 | GTA | TTT | TTA | CTT | AAG | GGT | ATT | GTG | GGT | TTC | CTC |    |

|     | Trp | Ser | Cys | Trp | Val | Leu | Val | Gly | Tyr | Ala | Lys | 26 |
|-----|-----|-----|-----|-----|-----|-----|-----|-----|-----|-----|-----|----|
| 744 | TGG | AGC | TGC | TGG | GTT | CTA | GTG | GGT | TAT | GCA | AAA |    |

|     | Gly | Gly | Leu | Gly | Asp | Asn | His | Val | His | Ser | Ser | 37 |
|-----|-----|-----|-----|-----|-----|-----|-----|-----|-----|-----|-----|----|
| 777 | GGA | GGT | TTG | GGA | GAC | AAT | CAT | GTT | CAC | TCC | AGT |    |

|     | Phe | Ile | Tyr | Arg | Arg | Leu | Arg | Asn | His | Glu | Arg | 48 |
|-----|-----|-----|-----|-----|-----|-----|-----|-----|-----|-----|-----|----|
| 810 | TTT | ATT | TAT | AGA | AGA | CTA | CGG | AAC | CAC | GAA | AGA |    |

|     | Arg | Glu | Ile | Gln | Arg | Glu | Ile | Leu | Ser | Ile | Leu | 59 |
|-----|-----|-----|-----|-----|-----|-----|-----|-----|-----|-----|-----|----|
| 843 | CGG | GAA | ATA | CAA | AGG | GAA | ATT | CTC | TCT | ATC | TTG |    |

|     | Gly | Leu | Pro | His | Arg | Pro | Arg | Pro | Phe | Ser | Pro | 70 |
|-----|-----|-----|-----|-----|-----|-----|-----|-----|-----|-----|-----|----|
| 876 | GGT | TTG | CCT | CAC | AGA | CCC | AGA | CCA | TTT | TCA | CCT |    |

|     | Gly | Lys | Gln | Ala | Ser | Ser | Ala | Pro | Leu | Phe | Met | 81 |
|-----|-----|-----|-----|-----|-----|-----|-----|-----|-----|-----|-----|----|
| 909 | GGA | AAA | CAA | GCG | TCC | TCT | GCA | CCT | CTC | TTT | ATG |    |

|     | Leu | Asp | Leu | Tyr | Asn | Ala | Met | Thr | Asn | Glu | Glu | 92 |
|-----|-----|-----|-----|-----|-----|-----|-----|-----|-----|-----|-----|----|
| 942 | CTG | GAT | CTC | TAC | AAT | GCC | ATG | ACC | AAT | GAA | GAA |    |

FIG. 3b

```
          Asn  Pro  Glu  Glu  Ser  Glu  Tyr  Ser  Val  Arg  Ala   103
975       AAT  CCT  GAA  GAG  TCG  GAG  TAC  TCA  GTA  AGG  GCA

Ser  Leu  Ala  Glu  Glu  Thr  Arg  Gly  Ala  Arg  Lys   114
1008      TCC  TTG  GCA  GAA  GAG  ACC  AGA  GGG  GCA  AGA  AAG

Gly  Tyr  Pro  Ala  Ser  Pro  Asn  Gly  Tyr  Pro  Arg   125
1041      GGA  TAC  CCA  GCC  TCT  CCC  AAT  GGG  TAT  CCT  CGT

Arg  Ile  Gln  Leu  Ser  Arg  Thr  Thr  Pro  Leu  Thr   136
1074      CGC  ATA  CAG  TTA  TCT  CGG  ACG  ACT  CCT  CTG  ACC

Thr  Gln  Ser  Pro  Pro  Leu  Ala  Ser  Leu  His  Asp   147
1107      ACC  CAG  AGT  CCT  CCT  CTA  GCC  AGC  CTC  CAT  GAT

Thr  Asn  Phe  Leu  Asn  Asp  Ala  Asp  Met  Val  Met   158
1140      ACC  AAC  TTT  CTG  AAT  GAT  GCT  GAC  ATG  GTC  ATG

Ser  Phe  Val  Asn  Leu  Val  Glu  Arg  Asp  Lys  Asp   169
1173      AGC  TTT  GTC  AAC  TTA  GTT  GAA  AGA  GAC  AAG  GAT

Phe  Ser  His  Gln  Arg  Arg  His  Tyr  Lys  Glu  Phe   180
1206      TTT  TCT  CAC  CAG  CGA  AGG  CAT  TAC  AAA  GAA  TTT

Arg  Phe  Asp  Leu  Thr  Gln  Lle  Pro  His  Gly  Glu   191
1239      CGA  TTT  GAT  CTT  ACC  CAA  ATT  CCT  CAT  GGA  GAG

Ala  Val  Thr  Ala  Ala  Glu  Phe  Arg  Ile  Tyr  Lys   202
1272      GCA  GTG  ACA  GCA  GCT  GAA  TTC  CGG  ATA  TAC  AAG

Asp  Arg  Ser  Asn  Asn  Arg  Phe  Glu  Asn  Glu  Thr   213
1305      GAC  CGG  AGC  AAC  AAC  CGA  TTT  GAA  AAT  GAA  ACA

Ile  Lys  Ile  Ser  Ile  Tyr  Gln  Ile  Ile  Lys  Glu   224
1338      ATT  AAG  ATT  AGC  ATA  TAT  CAA  ATC  ATC  AAG  GAA

Tyr  Thr  Asn  Arg  Asp  Ala  Asp  Leu  Phe  Leu  Leu   235
1371      TAC  ACA  AAT  AGG  GAT  GCA  GAT  CTG  TTC  TTG  TTA

Asp  Thr  Arg  Lys  Ala  Gln  Ala  Leu  Asp  Val  Gly   246
1404      GAC  ACA  AGA  AAG  GCC  CAA  GCT  TTA  GAT  GTG  GGT

Trp  Leu  Val  Phe  Asp  Ile  Thr  Val  Thr  Ser  Asn   257
1437      TGG  CTT  GTC  TTT  GAT  ATC  ACT  GTG  ACC  AGC  AAT
```

FIG. 3c

```
            His   Trp   Val   Ile   Asn   Pro   Gln   Asn   Asn   Leu   Gly   268
     1470   CAT   TGG   GTG   ATT   AAT   CCC   CAG   AAT   AAT   TTG   GGC

Leu   Gln   Leu   Cys   Ala   Glu   Thr   Gly   Asp   Gly   Arg   279
     1503   TTA   CAG   CTC   TGT   GCA   GAA   ACA   GGG   GAT   GGA   CGC

Ser   Ile   Asn   Val   Lys   Ser   Ala   Gly   Leu   Val   Gly   290
     1536   AGT   ATC   AAC   GTA   AAA   TCT   GCT   GGT   CTT   GTG   GGA

Arg   Gln   Gly   Pro   Gln   Ser   Lys   Gln   Pro   Phe   Met   301
     1569   AGA   CAG   GGA   CCT   CAG   TCA   AAA   CAA   CCA   TTC   ATG

Val   Ala   Phe   Phe   Lys   Ala   Ser   Glu   Val   Leu   Leu   312
     1602   GTG   GCC   TTC   TTC   AAG   GCG   AGT   GAG   GTA   CTT   CTT

Arg   Ser   Val   Arg   Ala   Ala   Asn   Lys   Arg   Lys   Asn   323
     1635   CGA   TCC   GTG   AGA   GCA   GCC   AAC   AAA   CGA   AAA   AAT

Gln   Asn   Arg   Asn   Lys   Ser   Ser   Ser   His   Gln   Asp   334
     1668   CAA   AAC   CGC   AAT   AAA   TCC   AGC   TCT   CAT   CAG   GAC

Ser   Ser   Arg   Met   Ser   Ser   Val   Gly   Asp   Tyr   Asn   345
     1701   TCC   TCC   AGA   ATG   TCC   AGT   GTT   GGA   GAT   TAT   AAC

Thr   Ser   Glu   Gln   Lys   Gln   Ala   Cys   Lys   Lys   His   356
     1734   ACA   AGT   GAG   CAA   AAA   CAA   GCC   TGT   AAG   AAG   CAC

Glu   Leu   Tyr   Val   Ser   Phe   Arg   Asp   Leu   Gly   Trp   367
     1767   GAA   CTC   TAT   GTG   AGC   TTC   CGG   GAT   CTG   GGA   TGG

Gln   Asp   Trp   Ile   Ile   Ala   Pro   Glu   Gly   Tyr   Ala   378
     1800   CAG   GAC   TGG   ATT   ATA   GCA   CCA   GAA   GGA   TAC   GCT

Ala   Phe   Tyr   Cys   Asp   Gly   Glu   Cys   Ser   Phe   Pro   389
     1833   GCA   TTT   TAT   TGT   GAT   GGA   GAA   TGT   TCT   TTT   CCA

Leu   Asn   Ala   His   Met   Asn   Ala   Thr   Asn   His   Ala   400
     1866   CTT   AAC   GCC   CAT   ATG   AAT   GCC   ACC   AAC   CAC   GCT

Ile   Val   Gln   Thr   Leu   Val   His   Leu   Met   Phe   Pro   411
     1899   ATA   GTT   CAG   ACT   CTG   GTT   CAT   CTG   ATG   TTT   CCT

Asp   His   Val   Pro   Lys   Pro   Cys   Cys   Ala   Pro   Thr   422
     1932   GAC   CAC   GTA   CCA   AAG   CCT   TGT   TGT   GCT   CCA   ACC
```

FIG. 3d

|      | Lys | Leu | Asn | Ala | Ile | Ser | Val | Leu | Tyr | Phe | Asp | 433 |
|------|-----|-----|-----|-----|-----|-----|-----|-----|-----|-----|-----|-----|
| 1965 | AAA | TTA | AAT | GCC | ATC | TCT | GTT | CTG | TAC | TTT | GAT |     |

|      | Asp | Ser | Ser | Asn | Val | Ile | Leu | Lys | Lys | Tyr | Arg | 444 |
|------|-----|-----|-----|-----|-----|-----|-----|-----|-----|-----|-----|-----|
| 1998 | GAC | AGC | TCC | AAT | GTC | ATT | TTG | AAA | AAA | TAT | AGA |     |

|      | Asn | Met | Val | Val | Arg | Ser | Cys | Gly | Cys | His |     | 454 |
|------|-----|-----|-----|-----|-----|-----|-----|-----|-----|-----|-----|-----|
| 2031 | AAT | ATG | GTA | GTA | CGC | TCA | TGT | GGC | TGC | CAC | TAA |     |

2064 TATTAAATAATATTGATAATAACAAAAAGATCTGTATTAAGGTTTATGGCTGCAATAAAAGCA

2128 TACTTTCAGACAAACAGAAAAAAAAA

FIG. 4a

```
1    GGGCGCAGCG GGGCCCGTCT GCAGCAAGTG ACCGACGGCC GGGACGGCCG CCTGCCCCCT

61   CTGCCACCTG GGGCGGTGCG GGCCCGGAGC CCGGAGCCCG GGTAGCGCGT AGAGCCGGCG
```

|     |     | Met | His | Val | Arg | Ser | Leu | Arg | Ala | Ala | Ala | 10  |
|-----|-----|-----|-----|-----|-----|-----|-----|-----|-----|-----|-----|-----|
| 121 | CG  | ATG | CAC | GTG | CGC | TCA | CTG | CGA | GCT | GCG | GCG |     |

|     | Pro | His | Ser | Phe | Val | Ala | Leu | Trp | Ala | Pro | Leu | 21  |
|-----|-----|-----|-----|-----|-----|-----|-----|-----|-----|-----|-----|-----|
| 153 | CCG | CAC | AGC | TTC | GTG | GCG | CTC | TGG | GCA | CCC | CTG |     |

|     | Phe | Leu | Leu | Arg | Ser | Ala | Leu | Ala | Asp | Phe | Ser | 32  |
|-----|-----|-----|-----|-----|-----|-----|-----|-----|-----|-----|-----|-----|
| 186 | TTC | CTG | CTG | CGC | TCC | GCC | CTG | GCC | GAC | TTC | AGC |     |

|     | Leu | Asp | Asn | Glu | Val | His | Ser | Ser | Phe | Ile | His | 43  |
|-----|-----|-----|-----|-----|-----|-----|-----|-----|-----|-----|-----|-----|
| 219 | CTG | GAC | AAC | GAG | GTG | CAC | TCG | AGC | TTC | ATC | CAC |     |

|     | Arg | Arg | Leu | Arg | Ser | Gln | Glu | Arg | Arg | Glu | Met | 54  |
|-----|-----|-----|-----|-----|-----|-----|-----|-----|-----|-----|-----|-----|
| 252 | CGG | CGC | CTC | CGC | AGC | CAG | GAG | CGG | CGG | GAG | ATG |     |

|     | Gln | Arg | Glu | Ile | Leu | Ser | Ile | Leu | Gly | Leu | Pro | 65  |
|-----|-----|-----|-----|-----|-----|-----|-----|-----|-----|-----|-----|-----|
| 285 | CAG | CGC | GAG | ATC | CTC | TCC | ATT | TTG | GGC | TTG | CCC |     |

|     | His | Arg | Pro | Arg | Pro | His | Leu | Gln | Gly | Lys | His | 76  |
|-----|-----|-----|-----|-----|-----|-----|-----|-----|-----|-----|-----|-----|
| 318 | CAC | CGC | CCG | CGC | CCG | CAC | CTC | CAG | GGC | AAG | CAC |     |

|     | Asn | Ser | Ala | Pro | Met | Phe | Met | Leu | Asp | Leu | Tyr | 87  |
|-----|-----|-----|-----|-----|-----|-----|-----|-----|-----|-----|-----|-----|
| 351 | AAC | TCG | GCA | CCC | ATG | TTC | ATG | CTG | GAC | CTG | TAC |     |

|     | Asn | Ala | Met | Ala | Val | Glu | Glu | Gly | Gly | Gly | Pro | 98  |
|-----|-----|-----|-----|-----|-----|-----|-----|-----|-----|-----|-----|-----|
| 384 | AAC | GCC | ATG | GCG | GTG | GAG | GAG | GGC | GGC | GGG | CCC |     |

|     | Gly | Gly | Gln | Gly | Phe | Ser | Tyr | Pro | Tyr | Lys | Ala | 109 |
|-----|-----|-----|-----|-----|-----|-----|-----|-----|-----|-----|-----|-----|
| 417 | GGC | GGC | CAG | GGC | TTC | TCC | TAC | CCC | TAC | AAG | GCC |     |

|     | Val | Phe | Ser | Thr | Gln | Gly | Pro | Pro | Leu | Ala | Ser | 120 |
|-----|-----|-----|-----|-----|-----|-----|-----|-----|-----|-----|-----|-----|
| 450 | GTC | TTC | AGT | ACC | CAG | GGC | CCC | CCT | CTG | GCC | AGC |     |

|     | Leu | Gln | Asp | Ser | His | Phe | Leu | Thr | Asp | Ala | Asp | 131 |
|-----|-----|-----|-----|-----|-----|-----|-----|-----|-----|-----|-----|-----|
| 483 | CTG | CAA | GAT | AGC | CAT | TTC | CTC | ACC | GAC | GCC | GAC |     |

|     | Met | Val | Met | Ser | Phe | Val | Asn | Leu | Val | Glu | His | 142 |
|-----|-----|-----|-----|-----|-----|-----|-----|-----|-----|-----|-----|-----|
| 516 | ATG | GTC | ATG | AGC | TTC | GTC | AAC | CTC | GTG | GAA | CAT |     |

|     | Asp | Lys | Glu | Phe | Phe | His | Pro | Arg | Tyr | His | His | 153 |
|-----|-----|-----|-----|-----|-----|-----|-----|-----|-----|-----|-----|-----|
| 549 | GAC | AAG | GAA | TTC | TTC | CAC | CCA | CGC | TAC | CAC | CAT |     |

FIG. 4b

|  |  |  |  |  |  |  |  |  |  |  |  |
|---|---|---|---|---|---|---|---|---|---|---|---|
| 582 | Arg CGA | Glu GAG | Phe TTC | Arg CGG | Phe TTT | Asp GAT | Leu CTT | Ser TCC | Lys AAG | Ile ATC | Pro CCA | 164 |
| 615 | Glu GAA | Gly GGG | Glu GAA | Ala GCT | Val GTC | Thr ACG | Ala GCA | Ala GCC | Glu GAA | Phe TTC | Arg CGG | 175 |
| 648 | Ile ATC | Tyr TAC | Lys AAG | Asp GAC | Tyr TAC | Ile ATC | Arg CGG | Glu GAA | Arg CGC | Phe TTC | Asp GAC | 186 |
| 681 | Asn AAT | Glu GAG | Thr ACG | Phe TTC | Arg CGG | Ile ATC | Ser AGC | Val GTT | Tyr TAT | Gln CAG | Val GTG | 197 |
| 714 | Leu CTC | Gln CAG | Glu GAG | His CAC | Leu TTG | Gly GGC | Arg AGG | Glu GAA | Ser TCG | Asp GAT | Leu CTC | 208 |
| 747 | Phe TTC | Leu CTG | Leu CTC | Asp GAC | Ser AGC | Arg CGT | Thr ACC | Leu CTC | Trp TGG | Ala GCC | Ser TCG | 219 |
| 780 | Glu GAG | Glu GAG | Gly GGC | Trp TGG | Leu CTG | Val GTG | Phe TTT | Asp GAC | Ile ATC | Thr ACA | Ala GCC | 230 |
| 813 | Thr ACC | Ser AGC | Asn AAC | His CAC | Trp TGG | Val GTG | Val GTC | Asn AAT | Pro CCG | Arg CGG | His CAC | 241 |
| 846 | Asn AAC | Leu CTG | Gly GGC | Leu CTG | Gln CAG | Leu CTC | Ser TCG | Val GTG | Glu GAG | Thr ACG | Leu CTG | 252 |
| 879 | Asp GAT | Gly GGG | Gln CAG | Ser AGC | Ile ATC | Asn AAC | Pro CCC | Lys AAG | Leu TTG | Ala GCG | Gly GGC | 263 |
| 912 | Leu CTG | Ile ATT | Gly GGG | Arg CGG | His CAC | Gly GGG | Pro CCC | Gln CAG | Asn AAC | Lys AAG | Gln CAG | 274 |
| 945 | Pro CCC | Phe TTC | Met ATG | Val GTG | Ala GCT | Phe TTC | Phe TTC | Lys AAG | Ala GCC | Thr ACG | Glu GAG | 285 |
| 978 | Val GTC | His CAC | Phe TTC | Arg CGC | Ser AGC | Ile ATC | Arg CGG | Ser TCC | Thr ACG | Gly GGG | Ser AGC | 296 |
| 1011 | Lys AAA | Gln CAG | Arg CGC | Ser AGC | Gln CAG | Asn AAC | Arg CGC | Ser TCC | Lys AAG | Thr ACG | Pro CCC | 307 |
| 1044 | Lys AAG | Asn AAC | Gln CAG | Glu GAA | Ala GCC | Leu CTG | Arg CGG | Met ATG | Ala GCC | Asn AAC | Val GTG | 318 |

FIG. 4c

```
          Ala  Glu  Asn  Ser  Ser  Ser  Asp  Gln  Arg  Gln  Ala       329
     1077 GCA  GAG  AAC  AGC  AGC  AGC  GAC  CAG  AGG  CAG  GCC

Cys  Lys  Lys  His  Glu  Leu  Tyr  Val  Ser  Phe  Arg       351
     1110 TGT  AAG  AAG  CAC  GAG  CTG  TAT  GTC  AGC  TTC  CGA

Asp  Leu  Gly  Trp  Gln  Asp  Trp  Ile  Ile  Ala  Pro       362
     1143 GAC  CTG  GGC  TGG  CAG  GAC  TGG  ATC  ATC  GCG  CCT

Glu  Gly  Tyr  Ala  Ala  Tyr  Tyr  Cys  Glu  Gly  Glu       373
     1176 GAA  GGC  TAC  GCC  GCC  TAC  TAC  TGT  GAG  GGG  GAG

Cys  Ala  Phe  Pro  Leu  Asn  Ser  Tyr  Met  Asn  Ala       384
     1209 TGT  GCC  TTC  CCT  CTG  AAC  TCC  TAC  ATG  AAC  GCC

Thr  Asn  His  Ala  Ile  Val  Gln  Thr  Leu  Val  His       395
     1242 ACC  AAC  CAC  GCC  ATC  GTG  CAG  ACG  CTG  GTC  CAC

Phe  Ile  Asn  Pro  Glu  Thr  Val  Pro  Lys  Pro  Cys       406
     1275 TTC  ATC  AAC  CCG  GAA  ACG  GTG  CCC  AAG  CCC  TGC

Cys  Ala  Pro  Thr  Gln  Leu  Asn  Ala  Ile  Ser  Val       417
     1308 TGT  GCG  CCC  ACG  CAG  CTC  AAT  GCC  ATC  TCC  GTC

Leu  Tyr  Phe  Asp  Asp  Ser  Ser  Asn  Val  Ile  Leu       428
     1341 CTC  TAC  TTC  GAT  GAC  AGC  TCC  AAC  GTC  ATC  CTG

Lys  Lys  Tyr  Arg  Asn  Met  Val  Val  Arg  Ala  Cys       439
     1374 AAG  AAA  TAC  AGA  AAC  ATG  GTG  GTC  CGG  GCC  TGT

Gly  Cys  His                                                442
     1407 GGC  TGC  CAC  TAG

1419 CTCCTCCGAGAATTCAGACCCTTTGGGGCCAAGTTTTTCTGGATCCTCCATTGCTCGCCTTGGC

1483 CAGGAACCAGCAGACCAACTGCCTTTTGTGAGACCTTCCCCTCCCTATCCCCAACTTTAAAGGT

1547 GTGAGAGTATTAGGAAACATGAGCAGCATATGGCTTTTGATCAGTTTTTCAGTGGCAGCATCCA

1611 ATGAACAAGATCCTACAAGCTGTGCAGGCAAAACCTAGCAGGAAAAAAAAACAACGCATAAAGA

1675 AAAATGGCCGGGCCAGGTCATTGGCTGGGAAGTCTCAGCCATGCACGGACTCGTTTCCAGAGGT
```

FIG. 4d

1739 AATTATGAGCGCCTACCAGCCAGGCCACCCAGCCGTGGGAGGAAGGGGGCGTGGCAAGGGGTGG

1803 GCACATTGGTGTCTGTGCGAAAGGAAAATTGACCCGGAAGTTCCTGTAATAAATGTCACAATAA

1867 AACGAATGAATG

METHOD OF TREATING GLAUCOMA COMPRISING ADMINISTERING A COMPOSITION COMPRISING HUMAN BMP7

The present application is a divisional of U.S. patent application Ser. No. 12/106,653 filed Apr. 21, 2008 (now allowed), which claims priority to U.S. patent application Ser. No. 10/286,152 filed Oct. 31, 2002 (now U.S. Pat. No. 7,405,192), which claims benefit to Provisional Application Ser. No. 60/334,852 filed Oct. 31, 2001.

BACKGROUND OF THE INVENTION

1. Field of the Invention

The present invention discloses methods and reagents for diagnosing and treating glaucoma and related disorders.

2. Description of the Related Art

"Glaucomas" are a group of debilitating eye diseases that are the leading cause of irreversible blindness in the United States and other developed nations. Primary Open Angle Glaucoma ("POAG"), the most common form of glaucoma, is characterized by the degeneration of the trabecular meshwork, leading to obstruction of the normal ability of aqueous humor to leave the eye without closure of the space (e.g., the "angle") between the iris and cornea (Vaughan, D. et al., (1992)). A characteristic of such obstruction in this disease is an increased intraocular pressure ("IOP"), resulting in progressive visual loss and blindness if not treated appropriately and in a timely fashion. The disease is estimated to affect between 0.4% and 3.3% of all adults over 40 years old (Leske, M. C. et al. (1986); Bengtsson, B. (1989); Strong, N. P. (1992)). Moreover, the prevalence of the disease rises with age to over 6% of those 75 years or older (Strong, N. P., (1992)).

Because increased IOP is a readily measurable characteristic of glaucoma, the diagnosis of the disease is largely screened for by measuring intraocular pressure (tonometry) (Strong, N. P. (1992); Greve, M. et al. (1993)). Unfortunately, because glaucomatous and normal pressure ranges overlap, such methods are of limited value unless multiple readings are obtained (Hitchings, R. A., (1993); Tuck, M. W. et al. (1993); Vaughan, D. et al., (1992); Vernon, S. A., (1993)). For this reason, additional methods, such as direct examination of the optic disk and determination of the extent of a patient's visual field loss are often conducted to improve the accuracy of diagnosis (Greve, M. et al., (1993)).

Glaucoma affects three separate tissues in the eye. The elevated IOP associated with POAG is due to morphological and biochemical changes in the trabecular meshwork (TM), a tissue located at the angle between the cornea and iris. Most of the nutritive aqueous humor exits the anterior segment of the eye through the TM. The progressive loss of TM cells and the build-up of extracellular debris in the TM of glaucomatous eyes leads to increased resistance to aqueous outflow (Lutjen-Drecoll and Rohen 1996; Rohen 1983; Rohen et al. 1993; Grierson and Calthorpe 1988), thereby raising IOP. Elevated IOP, as well as other factors such as ischemia, cause degenerative changes in the optic nerve head (ONH) leading to progressive "cupping" of the ONH (Varma and Minckler 1996; Hernandez and Gong 1996; Hernandez et al. 1990; Hernandez and Pena 1997; Morrison al. 1990) and loss of retinal ganglion cells (Quigley et al. 2000; Quigley 1999; Quigley et al. 1995; Kerrigan et al. 1997) and axons. The detailed molecular mechanisms responsible for glaucomatous damage to the TM, ONH, and the retinal ganglion cells are unknown.

Current glaucoma therapy is directed to lowering IOP, a major risk factor for the development and progression of glaucoma. These therapies lower IOP, but they do not directly address the pathogenic mechanisms, and the disease continues to progress. At least half of patients with glaucoma are undiagnosed, and by the time patients are diagnosed with glaucoma, they have already lost approximately 40% of their retinal ganglion cells. Therefore, methods for earlier detection and diagnosis of glaucoma are needed.

In view of the importance of glaucoma, and the at least partial inadequacies of prior methods of diagnosis, it would be desirable to have an improved, more accurate method for diagnosing glaucoma in its early stages. In addition, it would be desirable to have new therapeutic agents that address glaucomatous pathogenic mechanisms.

SUMMARY OF THE INVENTION

The present invention overcomes these and other drawbacks of the prior art by providing methods and kits for the early diagnosis of glaucoma, for treating glaucoma, and for the identification of compounds useful in the treatment of glaucoma.

In certain specific embodiments, the invention provides a method for diagnosing glaucoma in a sample obtained from a cell or bodily fluid by detecting altered expression of a bone morphogenic protein family member gene. The method generally includes the steps of:
  a) obtaining a tissue or fluid sample from a patient suspected of having glaucoma;
  b) extracting DNA from said sample;
  c) obtaining a plurality of PCR primers, wherein said primers each comprise a sequence consisting of from 18 to 1547 contiguous nucleotides from SEQ ID NO:1, SEQ ID NO:3, SEQ ID NO:5, SEQ ID NO:7, SEQ ID NO: 37, SEQ ID NO:39, SEQ ID NO:41, SEQ ID NO:43, SEQ ID NO:45, SEQ ID NO:47, or SEQ ID NO:53;
  d) amplifying regions of the extracted DNA using said primers to obtain a PCR product;
  e) resolving the PCR product; and
  f) identifying differences between the sequence of the PCR product and the normal gene sequence;
  where a difference between the amplified sequence and the normal gene sequence is diagnostic of glaucoma.

In general, the methods of the invention may include obtaining a sample from an individual and extracting DNA from said sample. Select PCR primers for specific members of the BMP gene family are then used to amplify relevant regions of the extracted gene to obtain a PCR product. The PCR product is resolved by a technique that effectively identifies DNA sequence differences between the normal and mutated form of the specific BMP family gene being evaluated (the extracted DNA). Identified differences between the sequences are indicative of glaucoma.

The tissue or fluid sample for use in the methods of the invention may be blood or buccal cells.

Typically, the primer sequences will have a length of between about 10, 15 or 18 nucleotides to about 20, or to about 30 nucleotides. Longer sequences, e.g., 40, 50, 80, 90, 95, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe, as described by Lathe (1985), which reference is specifically incorporated herein by reference for this purpose. Preferably, the nucleotide sequence will consist of from 20 to 100 contiguous nucleotides of SEQ ID NO:1, SEQ ID NO:3, SEQ ID NO:5, SEQ ID NO:7, SEQ ID NO:37, SEQ ID NO:39, SEQ ID NO:41, SEQ ID NO:43, SEQ ID NO:45, SEQ ID NO:47, or SEQ ID NO:53. It is also contemplated that the primer sequences may consist of sequences of at least 10, 15 or 18 contiguous nucleotides from the sequences of BMP receptor genes and from BMP-associated proteins, the sequences of which are known.

Nucleic acid molecules having stretches of 10, 18, 20, 30, 50, 60, 65 or even up to and including 100 nucleotides or so, complementary to any one of SEQ ID NO: 1, SEQ ID NO:3, SEQ ID NO:5, SEQ ID NO:7, SEQ ID NO:37, SEQ ID NO:39, SEQ ID NO:41, SEQ ID NO:43, SEQ ID NO:45, SEQ ID NO:47, or SEQ ID NO:53, have utility as hybridization probes. Primers or probes having a nucleotide length of about 18 nucleotides are recognized by those of skill in the art to provide highly specific hybridization to a target sequence. The total size of the fragment, as well as the size of the complementary stretches, will ultimately depend on the intended use of application of the particular nucleic acid segment. Smaller fragments will generally find use in hybridization embodiments, wherein the length of the complementary region may be varied, such as between about 10, 18, 20 or 30 and about 50, 60, 70, 80, 80 or 100 nucleotides, or even full length according to the complementary sequences one wishes to detect.

In specifically preferred embodiments, the primers will consist of contiguous sequences from SEQ ID NO: 1, SEQ ID NO:3, SEQ ID NO:5, SEQ ID NO:7, SEQ ID NO:37, SEQ ID NO:39, SEQ ID NO:41, SEQ ID NO:43, SEQ ID NO:45, SEQ ID NO:47, or SEQ ID NO:53. In other preferred embodiments, the primers will consist of contiguous sequences from BMP receptor genes (disclosed in ten Dijke et al. 1993; Astrom et al. 1999; Nohno et al. 1995, all incorporated herein by reference) or from BMP-associated genes, such as chordin (NCBI NM_029130), gremlin (Murphy et al. 1999; McMahon et al. 2000), follistatin (NCBI NM_003892) or bambi (NCBI NM_005791). Most preferably, the primers will consist of contiguous sequence from SEQ ID NO:3. In certain aspects, at least some of the primers may further include a detectable label.

In other embodiments, the invention provides a method for treating glaucoma by administering to a patient in need thereof a composition comprising a sequence consisting of at least one compound selected from the group consisting of a BMP2 agonist, a BMP4 agonist, a BMP5 agonist, a BMP7 agonist, a Smad 1/5 agonist, a chordin antagonist, a gremlin antagonist and a follistatin antagonist.

In additional aspects, the present invention provides a method for identifying a therapeutic agent for the treatment of glaucoma. Therapeutic agents may be identified, for example, by:
a) obtaining a first composition comprising a population of recombinant cells expressing BMP-2A, BMP4, BMP-5, or BMP7;
b) obtaining a candidate substance;
c) incubating said composition and said candidate substance;
testing said composition for its ability to turn on BMP-induced Smad signaling pathways and/or BMP-regulated gene expression; and identifying a candidate substance that inhibits, or stimulates, these downstream effects of BMP.

Another aspect of the invention are diagnostic kits containing sequences of the present invention and suitable reagents such as a detectable label linked to a protein, peptide or the antibody itself. Alternatively, the detectable label may be linked to a second sequence which selectively hybridizes to a sequence of the invention.

Related embodiments include therapeutic kits which include pharmaceutically-acceptable formulations of either the nucleic acid sequences or peptide or protein sequences disclosed herein. Such kits are useful in the detection of altered expression of the BMP genes and proteins in clinical samples for the diagnosis of glaucoma.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Nucleotide (SEQ ID NO: 1) and amino acid (SEQ ID NO: 2) sequence of BMP2A.

FIG. 2. Nucleotide (SEQ ID NO: 3) and amino acid (SEQ ID NO: 4) sequence of BMP4.

FIG. 3. Nucleotide (SEQ ID NO: 5) and amino acid (SEQ ID NO: 6) sequence of BMP5.

FIG. 4. Nucleotide (SEQ ID NO: 7) and amino acid (SEQ ID NO: 8) sequence of BMP7.

DETAILED DESCRIPTION PREFERRED EMBODIMENTS

Figure 5:
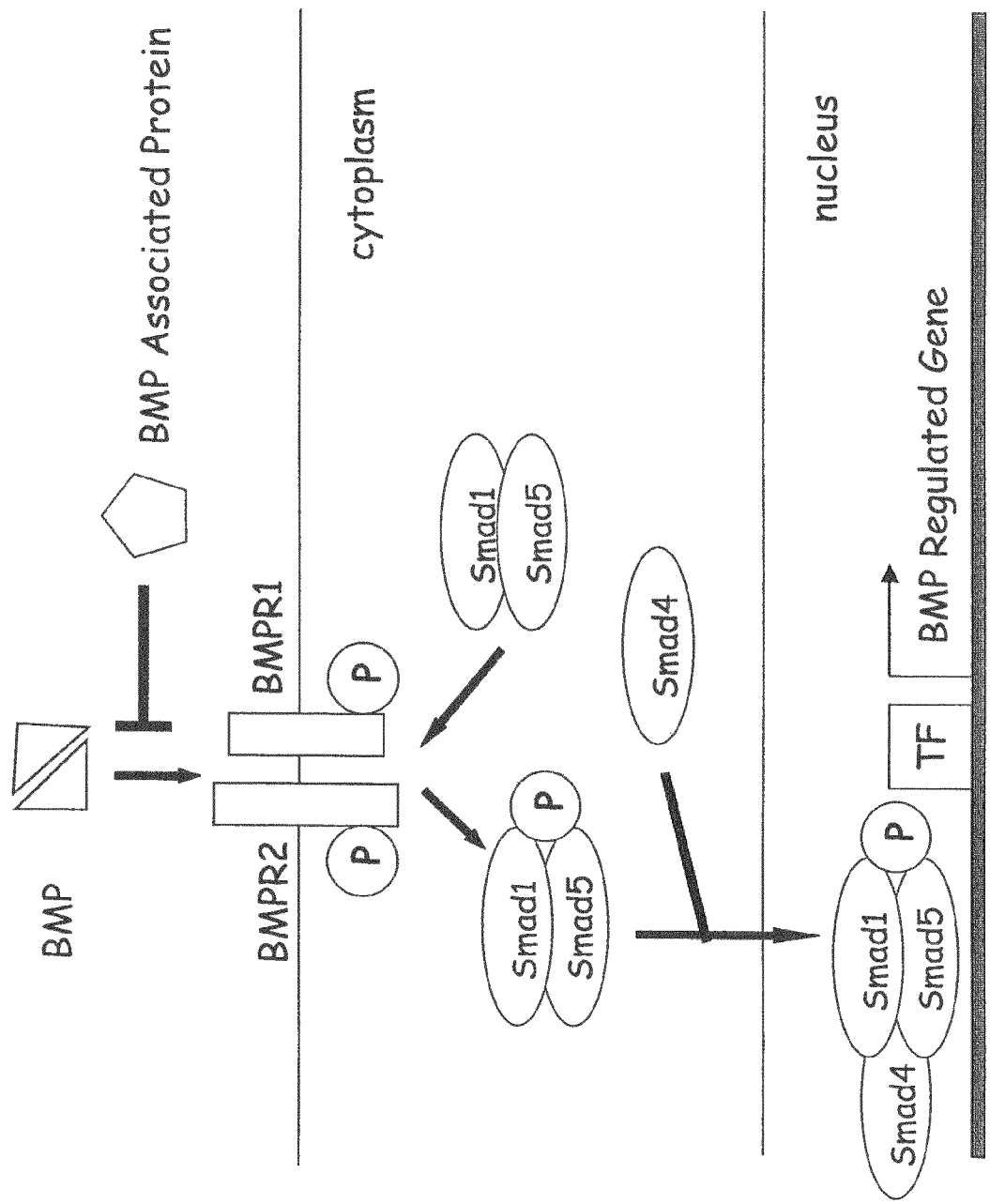
FIG. 5. Bone morphogenic protein signaling pathway. Bone Morphogenic Protein (BMP) dimers bind to a membrane complex composed of BMP receptors 1 and 2, which are serin/threonine kinases. The regulatory Smads (Smad1/Smad5) become phosphorylated and associate with a co-Smad (Smad 4). This resulting Smad complex enters the nucleus where it associates with transcription factors (TF) and regulates gene expression. BMP associated proteins act as BMP antagonists by binding BMPs and preventing BMP interaction with BMP receptors.

The trabecular meshwork has been proposed to play an important role in the normal flow of the aqueous humor, and has been presumed to be the major site of outflow resistance in glaucomatous eyes. Human trabecular meshwork (HTM) cells are specialized cells which line the outflow channels by which aqueous humor exits the eye. Altered synthetic function of the cells may be involved in the pathogenesis of POAG, steroid glaucoma, and other types of glaucoma.

Despite years of intensive research, the precise molecular mechanisms responsible for glaucomatous damage to the eye are not known. Recent research has suggested that growth factors may be important in maintaining normal homeostasis in the ocular tissues associated with glaucoma, and alterations in growth factor/growth factor receptors may play a role in glaucoma pathogenesis. Growth factors area very large family of polypeptides that control cell growth and differentiation. These molecules have a variety of cell-specific effects on gene expression, extracellular matrix composition and deposition, cytoskeletal organization, and regulation of cellular functions. The TM expresses a wide variety of growth factors, growth factor receptors (Tripathi et al. 1993a; Tripathi et al. 1993b; Tripathi et al. 1994a; Tripathi et al. 1994b; Wordinger et al. 1998; Wordinger et al. 1999) as well as neurotrophin/neurotrophic factors and their receptors (Liu et al. 2001; Wordinger et al. 2000). ONH astrocytes and lamina cribrosa cells, two cell types of the optic nerve head, express growth factors, neurotrophins and their receptors (Lambert et al. 2001; Pena et al. 1999). The aqueous humor also contains a variety of growth factors including FGF2, EGF, TGFβ, HGF (Tripathi et al. 1996; Tripathi et al. 1991; Tripathi et al. 1992; Hu and Ritch 2001) as well as neurotrophins (Chundru et al. 2000). Elevated levels of aqueous humor TGFβ-2 and HGF have been reported in POAG patients (Tripathi et al. 1994c; Inatani et al. 2001; Picht et al. 2001). Growth factors may be involved in glaucoma by altering the normal development and/or function of the TM and ONH.

The present invention stems in part from the recognition that bone morphogenic proteins (BMPs) not only induce bone and cartilage formation but are multifunctional cytokines having a wide range of effects on numerous cell types (Hogan 1996; Reddi 1997) and are expressed by both human trabecular meshwork (HTM) and optic nerve head (ONH) cells (Wordinger et al. 2002). BMPs are members of the TGFβ superfamily, and there are approximately 15-20 BMPs genes in man, 3 BMP receptors, and a number of BMP associated proteins that function as BMP antagonists (Yamashita et al. 1996). BMPs signal via a receptor complex consisting of BMPR-I and BMPR-II. It has been reported that superfamily members TGFβ and TGFβR (Agarwal et al. 1997; Lambert et al. 1997) and GDNF and GDNFR (Wordinger et al. 1999; Liu et al. 1999) are expressed by both HTM and ONH cells.

BMPs and BMP receptors are expressed in ocular tissues (Obata et al. 1999; You et al. 1999), but previous reports have focused on ocular development. The function of BMPs is important in ocular development since targeted disruption of genes encoding BMPs in mice leads to severe developmental defects in the retina and the lens (Jena et al. 1997; Luo et al. 1995; Dudley et al. 1995). BMP-2, BMP-4 and BMP-7 are involved in the development of the lens and retina (Jena et al. 1997; Furuta and Hogan 1998; Reddi 2000; Trousse et al. 2001). BMP-6 and BMP-7 also appear to play a role in protecting neurons from hypoglycemic or ischemic damage (Nonner et al. 2001; Liu et al. 2001), and BMP2 has been shown to enhance ganglion cell neurotrophin expression (Zhang et al. 1998). Heterozygous knock-out mice haploinsufficient for Bmp4 have ocular phenotypes including anterior segment dysgenesis, elevated IOP, and optic nerve abnormalities (Chang et al. 2001). There has been very limited information published concerning the role of BMPs in the human postnatal eye.

Mohan and colleagues (1998) reported that BMP-2 and BMP-4 and BMP receptors were expressed in cells of the adult cornea and suggested that BMP function might include corneal keratocyte proliferation and apoptosis. You and colleagues (1999) verified this study and also reported the expression of BMP-3, BMP-5, and BMP-7 in ex vivo and cultured corneal epithelium and stromal cells. They reported that the level of BMP transcription was higher in the stroma while the level for receptors was higher in cultured corneal epithelial cells.

Using RT-PCR, the present inventors discovered mRNAs for BMPs, BMP receptors BMPR-IA, BMPR-IB and BMPR-II, as well as BMP binding proteins gremlin, chordin, follistatin, and bambi, in HTM, lamina cribosa (LC) and ONH astrocyte cell lines and tissues (Wordinger et al. 2002). The present inventors further discovered that HTM and ONH cells express proteins BMP-2, BMP-4, BMP-5 and BMP-7.

Glaucoma will be diagnosed by characterization of genetic changes in genes of members of the BMP signaling family. As used herein, the phrases "bone morphogenic protein family member gene" and "BMP signaling family" refer to all BMPs, BMP receptors and associated proteins. The term "genetic changes" is well known by those skilled in the art. There are numerous examples of diseases associated with genetic changes in specific genes (for examples see Cummings 1997; Strachan, et al. 1996; Jorde, et al. 1999). Genetic changes in a specific gene (e.g. BMP) can be determined using a variety of techniques well known by those skilled in the art, such as: SSCP, DGGE, ASO, RFLP, heteroduplex analysis, CCM, PTT, and RNase cleavage (see Birren, et al. 1998).

Glaucoma may be caused by altered expression of one or more BMP family genes in the eye, which leads to elevated IOP and/or glaucomatous optic neuropathy. "Altered BMP gene expression" means expression of this gene product that is different from normal. The term may also refer to alterations in the sequence of the gene or protein. The normal BMP gene has been well characterized (see above), and the expression of BMP has been reported in a variety of tissues including the TM and ONH. Genetic changes in the coding region of BMP family genes may alter the function of these proteins. Genetic changes outside the coding region may also lead to glaucoma.

It is well known by those skilled in the art that "changes outside" of the coding region of a specific gene are important in the regulation of gene expression. For example, the region upstream (5') of the coding region of most genes is known as the promoter region which "promotes" and regulates the expression of that gene. The promoter region contains numerous nucleotide sequences recognized by various transcription factors and DNA binding proteins that are responsible for activation or repression of gene expression. Regions downstream (3') of the gene can determine poly-adenylation of the gene product, thereby regulating RNA processing and translation of the gene product.

The altered expression of BMP genes or mutations in the sequence of the genes that is indicative of glaucoma may be detected using techniques well known to those of skill in the art. For example, it is contemplated that a nucleic acid fragment of almost any length may be employed, with the total length preferably being limited by the ease of preparation and use in the intended protocol. The nucleic acid sequences disclosed herein may also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of BMP-2A (SEQ ID NO:1), BMP-4 (SEQ ID NO:3), BMP-5 (SEQ ID NO:5), BMP-7 (SEQ ID NO:7), BMP-RIA (SEQ ID NO:37), BMP-RIB (SEQ ID NO:39), BMP-RII (SEQ ID NO:41), chordin (SEQ ID NO:43), gremlin (SEQ ID NO:45), follistatin (SEQ ID NO:47), or bambi (SEQ ID NO:53) will find particular utility. Longer contiguous identical or complementary sequences, e.g., those of about 20, 30, 40, 50, 100, 200, 500, 1000 nucleotides (including all intermediate lengths), and even up to full length sequences of about 1547 nucleotides (for BMP-2A), 1946 nucleotides (for BMP-4), 2153 nucleotides (for BMP-5) and 1878 nucleotides (for BMP-7), 2932 nucleotides (for BMP-RIA), 2032 nucleotides (for BMP-RIB), 3611 nucleotides (for BMP-RII), 3561 nucleotides (for chordin), 4049 nucleotides (for gremlin), 1386 nucleotides (for follistatin), and 1523 nucleotides (for bambi) will also be of use in certain embodiments.

It will be readily understood that "intermediate lengths", in this context, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000 ranges, up to and including sequences of 2,001, 2002, 2050, 2051, and the like.

The ability of such nucleic acid probes and primers to specifically hybridize to BMP coding sequences and primers to specifically amplify BMP sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10, 20, 30, 50, or even of 100-200 nucleotides or so, identical or complementary to BMP-2A (SEQ ID NO:1), BMP4 (SEQ ID NO:3), BMP-5 (SEQ ID NO:5), BMP7 (SEQ ID NO:7), BMP-RIA (SEQ ID NO:37), BMP-RIB (SEQ ID NO:39), BMP-RII (SEQ ID NO:41), chordin (SEQ ID NO:43), gremlin (SEQ ID NO:45), follistatin (SEQ ID NO:47), or bambi (SEQ ID NO:53) are particularly contemplated as hybridization probes for use in, e.g., SNP evaluation and solid phase hybridization assays, in addition to Southern and northern blotting. This would allow BMP structural or regulatory genes to be analyzed, both in tissues and cells. The total size of fragment, as well as the size of the complementary stretch(es), will ultimately depend on the intended use of application of the particular nucleic acid segment. Smaller fragments will generally find use in hybridization embodiments, wherein the length of the contiguous complementary region may be varied, such as between about 10 and about 100 nucleotides, but larger contiguous complementary stretches of up to about 1547 nucleotides (for BMP-2A), 1946 nucleotides (for BMP-4), 2153 nucleotides (for BMP-5) and 1878 nucleotides (for BMP-7), 2932 nucleotides (for BMP-RIA), 2032 nucleotides (for BMP-RIB), 3611 nucleotides (for BMP-RII), 3561 nucleotides (for chordin), 4049 nucleotides (for gremlin), 1386 nucleotides (for follistatin), and 1523 nucleotides (for bambi) may be used, according to the length complementary sequences one wishes to detect.

The use of a hybridization probe of about 10-14 nucleotides in length allows the formation of a duplex molecule that is both stable and selective. Molecules having contiguous complementary sequences over stretches greater than 10 bases in length are generally preferred, though, in order to increase stability and selectivity of the hybrid, and thereby improve the quality and degree of specific hybrid molecules obtained, one will generally prefer to design nucleic acid molecules having gene-complementary stretches of 15 to 20 contiguous nucleotides, or even longer where desired.

Hybridization probes may be selected from any portion of any of the sequences disclosed herein. All that is required is to review the sequence set forth in SEQ ID NO:1, SEQ ID NO:3, SEQ ID NO:5, SEQ ID NO:7, SEQ ID NO:37, SEQ ID NO:39, SEQ ID NO:41, SEQ ID NO:43, SEQ ID NO:45, SEQ ID NO:47 or SEQ ID NO:53 and to select any continuous portion of the sequence, from about 10 nucleotides in length up to and including the full length sequence, that one wishes to utilize as a probe or primer. The choice of probe and primer sequences may be governed by various factors, such as, by way of example only, one may wish to employ primers from towards the termini of the total sequence, or from the ends of the functional domain-encoding sequences, in order to amplify further DNA.

The process of selecting, and preparing a nucleic acid segment that includes a contiguous sequence from within BMP-2A (SEQ ID NO:1), BMP4 (SEQ ID NO:3), BMP-5 (SEQ ID NO:5), BMP7 (SEQ ID NO:7), BMP-RIA (SEQ ID NO:37), BMP-RIB (SEQ ID NO:39), BMP-RII (SEQ ID NO:41), chordin (SEQ ID NO:43), gremlin (SEQ ID NO:45), follistatin (SEQ ID NO:47), or bambi (SEQ ID NO:53) may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 and U.S. Pat. No. 4,682,195 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of BMP genes or cDNAs. Depending on the application envisioned, one will desire to employ varying degrees of selectivity of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M-0.15M NaCl at temperatures of 50° C. to 70° C. Such selective conditions tolerate little, if any, mismatch between the probe and the template or target strand, and would be particularly suitable for examining BMP genes.

Of course, for some applications, for example, where one desires to prepare or identify mutants employing a mutant primer strand hybridized to an underlying template or where one seeks to isolate BMP encoding sequences from related species, functional equivalents, or the like, less stringent hybridization conditions will typically be needed in order to allow formation of the heteroduplex. In these circumstances, one may desire to employ conditions such a 0.15M-1.0M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by decreasing NaCl concentrations or by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

It will also be understood that this invention is not limited to the particular nucleic acid and amino acid sequences of BMP-2A (SEQ ID NO:1), BMP4 (SEQ ID NO:3), BMP-5 (SEQ ID NO:5), BMP7 (SEQ ID NO:7), BMP-RIA (SEQ ID NO:37), BMP-RIB (SEQ ID NO:39), BMP-RII (SEQ ID NO:41), chordin (SEQ ID NO:43), gremlin (SEQ ID NO:45), follistatin (SEQ ID NO:47), or bambi (SEQ ID NO:53). Recombinant vectors and isolated DNA segments may therefore variously include the BMP coding regions themselves, upstream or downstream regions of the genes, coding regions bearing selected alterations or modifications in the basic coding region, or they may encode larger polypeptides that nevertheless include BMP coding regions or may encode biologically functional equivalent proteins or polypeptides that have variant amino acid sequences.

The DNA segments of the present invention encompass biologically functional equivalent BMP proteins and polypeptides. Such sequences may arise as a consequence of codon redundancy and functional equivalency that are known to occur naturally within nucleic acid sequences and the proteins thus encoded. Alternatively, functionally equivalent proteins or polypeptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test BMP mutants in order to examine binding activity at the molecular level.

The therapeutic agent for the treatment of glaucoma can be: a peptide or protein, a peptide mimetic, an oligonucleotide or derivatized oligonucleotide, or small drug-like molecule, all which affect one or more aspects of the ocular BMP pathways. Preferred therapeutic agents are those that are: (1) BMP2, BMP4, BMP5, or BMP7 agonists; (2) chordin, gremlin, follistatin, or bambi antagonists; and/or (3) Smad1, Smad5 and/or Smad4 agonists.

The agent may be delivered directly to the eye (for example: topical ocular drops or ointments; slow release devices in the cul-de-sac or implanted adjacent to the sclera or within the eye; periocular, conjunctival, sub-Tenons, intracameral or intravitreal injections) or parenterally (for example: orally; intravenous, subcutaneous or intramuscular injections; dermal delivery; etc.) using techniques well known by those skilled in the art. The following are examples of possible formulations embodied by this invention.

|  | wt. % |
|---|---|
| (a) Topical ocular formulation | |
| Agent that increases ocular BMP-4 expression | 0.01-2 |
| HPMC | 0.5 |
| Sodium chloride | 0.8 |
| BAC | 0.01% |
| EDTA | 0.01 |
| NaOH/HCl | qs pH 7.4 |
| Purified water | qs 100 mL |

-continued

| | wt. % |
|---|---|
| (b) Topical ocular formulation | |
| Gremlin antagonist | 0.01-2 |
| HPMC | 0.5 |
| Sodium chloride | 0.8 |
| BAC | 0.01 |
| EDTA | 0.01 |
| NaOH/HCl | qs pH 7.4 |
| Purified water | qs 100 mL |
| (c) Topical ocular formulation | |
| Smad 1/5 agonist | 0.01-2 |
| HPMC | 0.5 |
| Sodium chloride | 0.8 |
| BAC | 0.01 |
| EDTA | 0.01 |
| NaOH/HCl | qs pH 7.2 |
| Purified water | qs 100 mL |

It is further contemplated that the compounds of the invention could be formulated in intraocular insert devices.

A. Assay for Therapeutic Agents

This invention is also useful for the discovery of new anti-glaucoma therapeutic agents that are involved in the BMP signaling pathway (see FIG. 5). Selective BMP ligands bind to BMP type I and type II serine/threonine kinase receptors (BMP-RI and BMP-RII) and transduce signal via Smad proteins. The BMP signal is propagated by Smads through protein-protein and protein-DNA interactions (Attisano and Tuen Lee-Hoeflich 2001). Regulatory Smad 1 and Smad 5 are activated (via phosphorylation) by ligand bound BMP receptors (von Bubnoff and Cho 2001). These regulatory Smads then interact with Smad 4 to form a heteromeric complex that translocates to the nucleus. This complex is able to activate or repress the transcription of selective genes that recognize this transcriptional complex, depending on which nuclear co-factors are present.

The BMP/Smad signaling pathway is negatively regulated by several mechanisms. Certain BMP-binding proteins (such as gremlin, BAMBI, or follistatin) bind BMPs and inhibit their interaction with BMP receptors. In addition, there are inhibitory Smad proteins (e.g. Smad 6 and Smad 7), which bind and inactivate BMP receptors. (Kowabata et al. 1998; Itoh et al. 2000; Miyazono 2000). The present inventors have discovered that human TM cells, ONH astrocytes and lamina cribrosa cells express message and protein for the BMP receptor complex. Thus, these cells could respond to endogenous BMP ligands.

Various methods may be used to discover new anti-glaucoma therapeutic agents, and these techniques are well known to those skilled in the art. For example, peptide or peptide mimetic agents that act as agonists or inhibitors of BMPs can be discovered through molecular modeling of BMP/BMP receptor structures (Nickel et al. 2001). BMP signal transduction involves select sets of Smad proteins (Kawabata et al. 1998; Itoh et al. 2000; Attiseno et al. 2000). Select BMP agonists and Smad agonists can be discovered using cell based assays. The test cell should express the appropriate BMP receptor(s) and possess the appropriate BMP signaling pathway. Because one of the major effects of BMP signaling is the alteration of gene expression, BMP agonists and Smad agonists can be discovered by screening for BMP-induced genes. The induction of BMP regulated genes also may be assayed by quantitating levels of mRNA using quantitative RT-PCR (Wang et al. 2001), DNA microarrays, or reporter gene constructs. There are natural inhibitors of BMP signaling, the BMP binding proteins (also known as BMP-associated proteins), such as chordin, gremlin, and follistatin. Antagonists of the protein inhibitors can be discovered using ligand binding assays. For example, test agents can be added to recombinant purified gremlin, and those agents that bind to gremlin are identified using a variety of techniques known to those skilled in the art. To determine whether these agents are gremlin antagonists, a cell based assay similar to that described above is used.

It is contemplated that any known in vitro and in vivo screening models may be used in conjunction with the present invention to identify new glaucoma therapies directed to the BMP family of genes. Such models are well known to those skilled in the art and their practice has become routine. Small peptides or peptide mimetics can be designed based on structure/function knowledge of the BMP, BMPR, and/or BMP binding protein gene products. Ligand binding assays can be used to detect small molecules that bind to BMPs, BMPRs, or BMP binding proteins. Cell based assays can look at the effects of various agents on BMP signaling pathways. Knock-in cell lines containing BMP family gene promoters coupled to a reporter gene can be generated to look for agents that alter BMP family member gene expression. These assays can be used to identify both agonist and antagonist molecules. Ex vivo assays, such as perfusion cultured anterior segments from human eyes (Clark et al. 1995a; Pang et al. 2000), can be used to examine the effects of agents on IOP and on BMP signaling in TM tissue. Rodent models of glaucoma can be generated using well-known techniques to create stable BMP family member transgenic, knockout, or knock-in strains of mice and rats. These rodent models can be used to screen for agents that alter the glaucoma-like phenotype(s) (e.g. tonometry to evaluate effects on IOP, histology to evaluate effects on glaucomatous optic neurology).

B. Kits

The present invention provides methods, compositions and kits for the early detection of glaucoma. The kits can contain a nucleic acid segment encoding a BMP polypeptide or protein. The kit can further contain reagents for detecting an interaction between a sample and a nucleic acid or peptide of the present invention. The provided reagent can be radio-, fluorescently- or enzymatically-labeled. The kit can contain a known radiolabeled agent capable of binding or interacting with a nucleic acid or peptide or protein of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatography media, a test plate having a plurality of wells, or a microscope slide. When the reagent provided is a dry powder, the powder can be reconstituted by the addition of a suitable solvent, that may be provided.

In still further embodiments, the present invention concerns diagnostic methods and associated kits for the diagnosis of glaucoma. It is proposed that the BMP associated peptides and nucleic acids of the invention may be employed to detect polymorphisms or mutations in the BMP nucleic acids from patient samples. In general, these methods will include first obtaining a sample suspected of containing such a polymorphism or mutation, contacting the sample with a peptide or nucleic acid of the present invention, as the case may be, under conditions effective to allow the formation of a complex, and then detecting the presence of the complex.

In general, the detection of complex formation is quite well known in the art and may be achieved through the application of numerous approaches. For example, the present invention contemplates the application of ELISA, RIA, indirect fluorescence techniques and the like. Generally, complex formation will be detected through the use of a label, such as a radiolabel or an enzyme tag (such as alkaline phosphatase, horseradish peroxidase, or the like). Of course, one may find additional advantages through the use of a secondary binding ligand.

The following examples are representative of the techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Example 1

Cell culture: Human TM cells and ONH cells were generated from donor eyes as described (Steely et al. 1992; Steely et al. 2000; Wilson et al. 1993; Clark et al. 1994; Clark et al. 1995b; Clark et al. 1995c; Clark et al. 1996; Clark et al. 2001a; Clark et al. 2001b; Dickerson et al. 1998; Wordinger et al. 1998; Wordinger et al. 1999; Wordinger et al. 2000; Wordinger et al. 2002; Lambert et al. 2001; Agarwal et al. 1999; Liu et al. 2001). TM cells were grown from TM explants of donors ranging in age from 6 days to 90 years. Human optic nerve head astrocytes and lamina cribrosa (LC) cells were generated from carefully dissected optic nerve heads (donors aged 2 days to 90 years) and characterized according to previous reports (Lambert et al. 2001; Clark et al. 1995a). The cells were grown to confluency in the following media: Ham's F10 media (JRH Biosciences, Lenexa, Kans.) containing 10% fetal bovine serum (HyClone, Logan, Utah) and antibiotics (Gibco BRL-Life Technologies, Grand Island, N.Y.) for TM cells; Dulbecco's modified Eagle's media (DMEM, HyClone) containing 10% FBS for LC cells; and astrocyte growth medium (AGM, Clonetics, San Diego, Calif.) containing 5% FBS for ONH astrocytes.

RT-PCR: Human TM and ONH tissues also were dissected from donor eyes (Wordinger et al. 1998; Wang et al. 2001). Total RNA was extracted from the TM and ONH cells and tissues using TRIzol extraction (Gibco BRL-Life Technologies), and cDNA prepared by reverse transcription using standard procedures (Wordinger et al. 1998; Wordinger et al. 1999; Wordinger et al. 2000; Wordinger et al. 2002). PCR primers were designed using the Oligos 4.0 software program (see primer pairs in Table 1). All primer pairs were designed so that amplification of potentially contaminated genomic DNA sequences would produce mRNA PCR products that would be substantially larger than expected, because intron sequences that were excised during RNA processing would be included in genomic DNA. The β-actin PCR primers, AGGCCAACCGCGAGAAGATGACC (upstream) (SEQ ID NO: 55) and GAAGTCCAGGGCGACGTAGCAC (downstream) (SEQ ID NO: 56) with an annealing temperature of 55° C. yielded a PCR product of 350 bp.

PCR reactions were run as described (Wordinger et al. 1998; Wordinger et al. 1999; Wordinger et al. 2000; Lambert et al. 2001; Wordinger et al. 2002) using Taq Start Antibody Hot Start with the following cycle conditions: 2 minutes at 94° C., 2 minutes at 92° C., and 40 cycles of 30 seconds at the optimal annealing temperature, extension for 90 seconds at 72° C. and denaturation for 45 seconds at 92° C. The amplified PCR products were examined by horizontal electrophoresis in 1.5% agarose gels. To ensure specificity of the RT-PCR products, Southern blot analysis was performed with probes designed using Oligo 4.0 that hybridized to a region within the amplified PCR product. PCR products were sequenced to verify the specificity of the PCR reactions. Table 2 lists the members of the BMP family that are expressed in the human TM and ONH.

TABLE 1

PCR Primer Pairs, Annealing Temperature and Amplimer Size of BMPs

| Name | Assession Number | Upstream PCR Primer | Downstream PCR Primer | Ampl. Size (bp) |
| --- | --- | --- | --- | --- |
| BMP-2A | NM_001200 | ACTGCGGTCTCCTAAA GGTCGA (SEQ ID NO: 9) | GCTGACCTGAGTGCCT GCGAT (SEQ ID NO: 10) | 657 |
| BMP-4 | NM_001202 | GAATGCTGATGGTCGT TTTTATTATG (SEQ ID NO: 11) | AGACTGAAGCCGGTA AAGAT (SEQ ID NO: 12) | 348 |
| BMP-5 | NM_021073 | AAGAGGACAAGAAGG ACTAAAAATAT (SEQ ID NO: 13) | GTAGAGATCCAGCATA AAGAGAGGT (SEQ ID NO: 14) | 303 |
| BMP-7 | NM_001719 | AGCCCGGGTAGCGCGT AGAG (SEQ ID NO: 15) | GCGCCGGTGGATGAA GCTCGA (SEQ ID NO: 16) | 202 |
| BMPR-1A | NM_004329 | TAAAGGTGACAGTACA CAGGAACA (SEQ ID NO: 17) | TCTATGATGGCAAAGC AATGTCC (SEQ ID NO: 18) | 298 |
| BMPR-1B | NM_001203 | TACAAGCCTGCCATAA GTGAAGAAGC (SEQ ID NO: 19) | ATCATCGTGAAACAAT ATCCGTCTG (SEQ ID NO: 20) | 211 |
| BMPR-II | NM_001204 | TCCTCTCATCAGCCAT TTGTCCTTTC (SEQ ID NO: 21) | AGTTACTACACATTCT TCATAG (SEQ ID NO: 22) | 457 |

TABLE 1-continued

PCR Primer Pairs, Annealing Temperature and Amplimer Size of BMPs

| Name | Assession Number | Upstream PCR Primer | Downstream PCR Primer | Ampl. Size (bp) |
|---|---|---|---|---|
| Chordin (CHRD) | AF209930 | CTCTGCTCACTCTGCA CCTG (SEQ ID NO: 23) | CCGGTCACCATCAAAA TAGC (SEQ ID NO: 24) | 198 |
| Gremlin (CKTSF1 B1) | NM_013372 | ATCAACCGCTTCTGTT ACGG (SEQ ID NO: 25) | ATGCAACGACACTGCT TCAC (SEQ ID NO: 26) | 197 |
| Follistatin (FST) | NM_006350 | TGCCACCTGAGAAAGG CTAC (SEQ ID NO: 27) | ACAGACAGGCTCATCC GACT (SEQ ID NO: 28) | 201 |
| Noggin (NOG) | NM_005450 | CACTACGACCCAGGCT TCAT (SEQ ID NO: 29) | CTCCGCAGCTTCTTGC TTAG (SEQ ID NO: 30) | 212 |
| CER-1 | NM_005454 | ATAGTGAGCCCTTCCC ACCT (SEQ ID NO: 33) | AATGAACAGACCCGC ATTTC (SEQ ID NO: 34) | 294 |
| NMA (BAMBI) | NM_005791 | GATCGCCACTCCAGCT ACATC (SEQ ID NO: 35) | GGGCACGGCAATGACC (SEQ ID NO: 36) | 471 |

TABLE 2

BMP Family Members Expressed in Human TM and ONH

| BMP Family Member | Trabecular Meshwork | Optic Nerve Head |
|---|---|---|
| BMP-2 | + | + |
| BMP-4 | + | + |
| BMP-5 | + | + |
| BMP-7 | + | + |
| BMPR-IA | + | + |
| BMPR-IB | + | + |
| BMPR-II | + | + |
| Chordin | + | + |
| Gremlin | + | + |
| Follistatin | + | + |
| Bambi | + | + |
| Noggin | − | − |
| CER-1 | − | − |

Western immunoblotting: Protein was extracted from cultured cells using lysis buffer, and proteins were separated by denaturing polyacrylamide gel electrophoresis prior to electrophoretic transfer to nitrocellulose membranes (Lambert et al. 2001). The membranes were blocked with 5% milk (for BMPs) or 3% gelatin (for BMPRs) and incubated with the following primary antibodies: BMP2, BMP4, BMP5, BMP7 (all from Santa Cruz, Santa Cruz, Calif.), or BMP-RIA, BMP-RIB, BMP-RII (from Jackson Immuno Research, West Grove, Pa.). The membranes were washed, incubated with secondary antibodies (goat anti-mouse IgG-horseradish peroxidase for BMPs, Santa Cruz; donkey anti-goat-horseradish peroxidase for BMP receptors, Jackson Immuno Research), and developed using the WesternBreeze chemiluminescence immunodetection system (Invitrogen, Carlsbad, Calif.).

Figure 6:
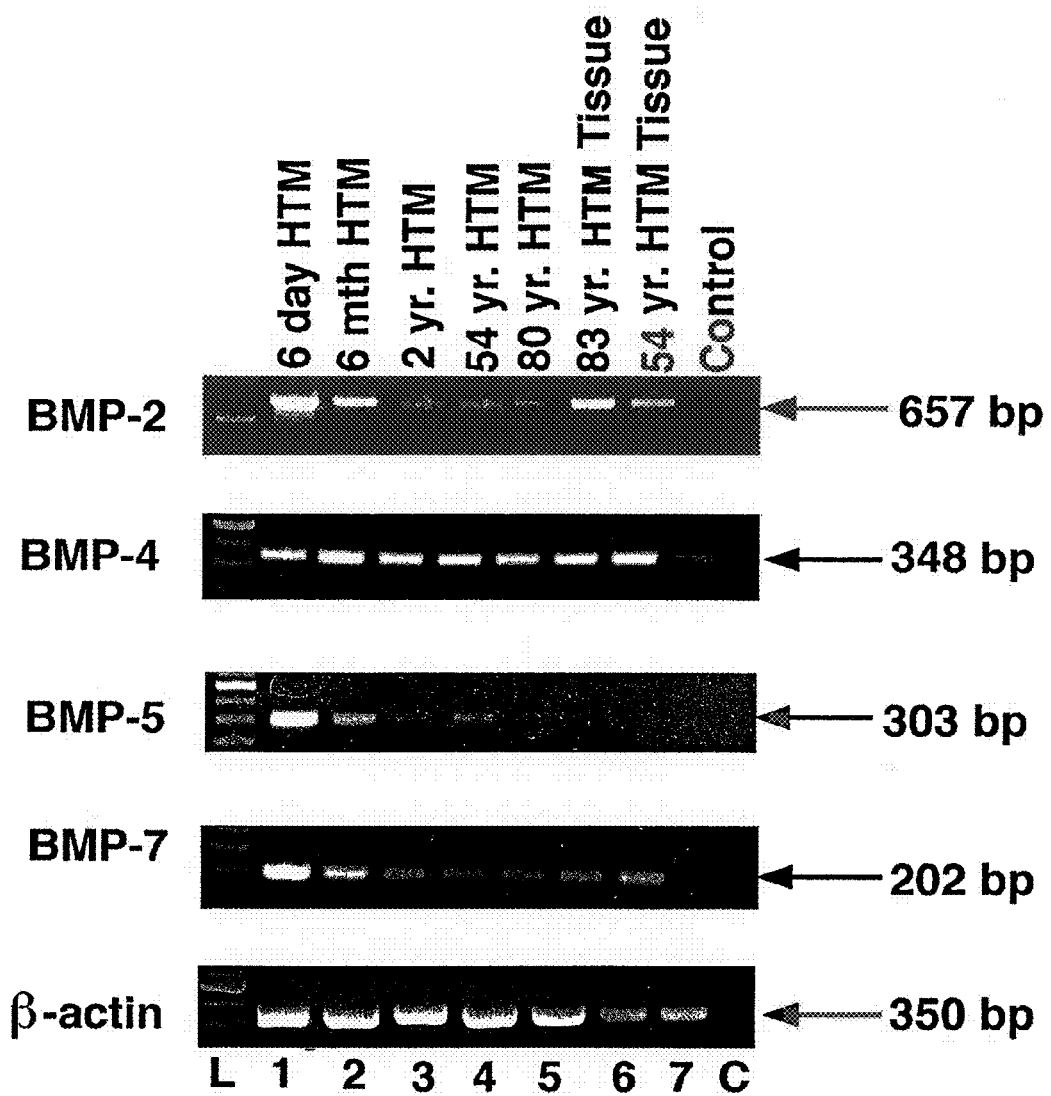
FIG. 6. BMP expression in human TM cells and tissues. Ethidium bromide-stained agarose gel of BMP PCR products from cDNA samples generated from RT-PCR analysis of BMP expression in human TM cells (lanes 1-5) and tissues (lanes 6-7). L=base pair markers. C=PCR negative control lane. β-actin was used as a positive RT-PCR internal control.

Expression of BMPs, BMPRs mRNA in human TM cells and tissues: Amplification products of expected for BMP-2, BMP-4, BMP-5 and BMP-7 primer pairs in human TM cells and tissues are shown in FIG. 6. Southern blots using specific probes verified that these were the expected PCR products. All human TM cell lines and tissues expressed message for BMP-2, BMP-4, and BMP-7. However, message for BMP-5 was low to undetectable in human TM tissue samples (FIG. 6, lanes 6 and 7). Control reactions without cDNA did not result in amplification products indicating that reagents and primers were free of DNA or RNA contamination (FIG. 6, lane C).

Figure 7:
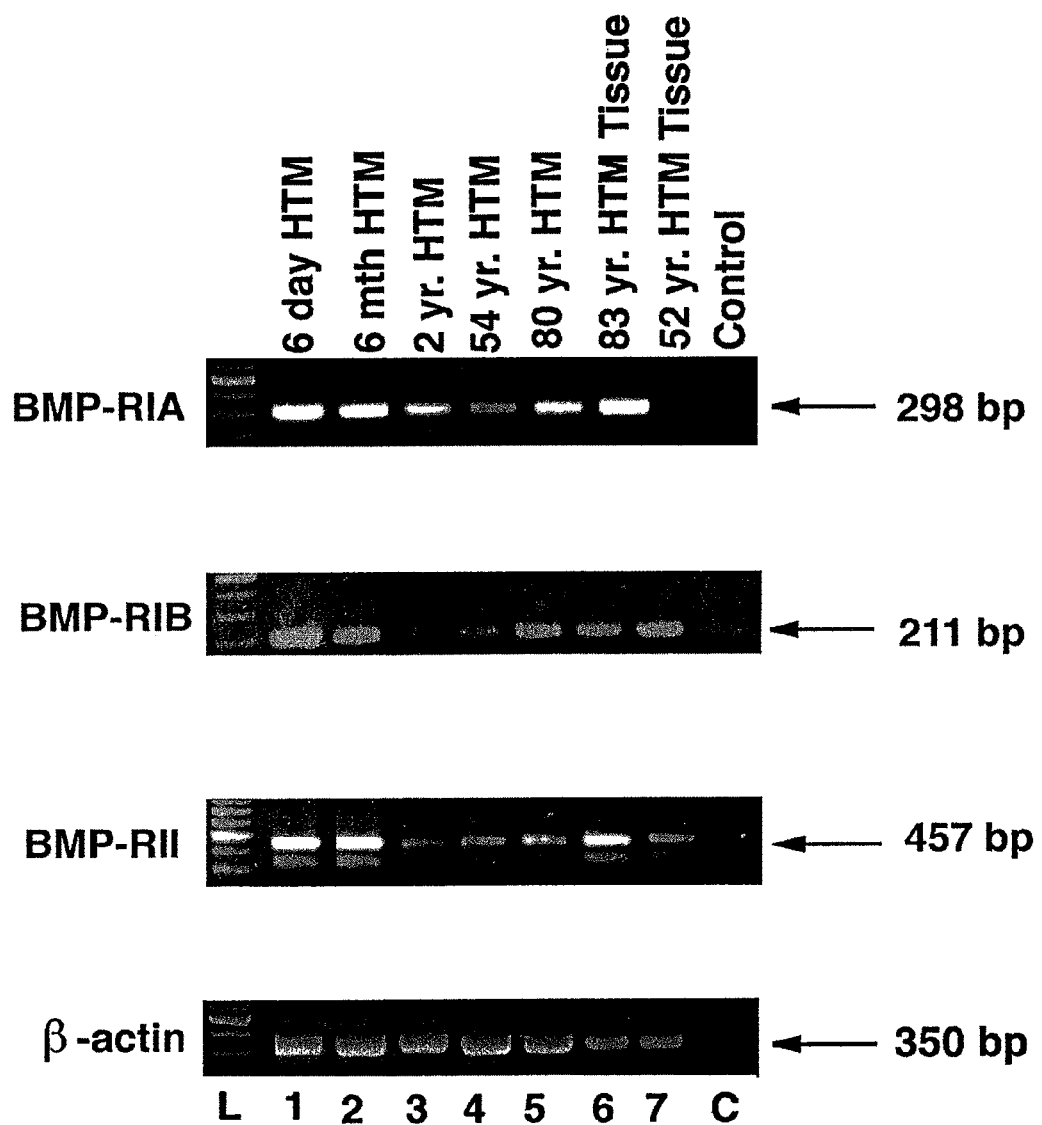
FIG. 7. BMP receptor expression in human TM cells and tissues. Ethidium bromide-stained agarose gel of PCR products from cDNA samples generated from RT-PCR analysis of BMP receptor expression in human TM cells (lanes 1-5) and tissues (lanes 6-7). L=base pair markers. C=PCR negative control lane. β-actin was used as a positive RT-PCR internal control.

FIG. 7 shows the amplification products of expected size for BMP-RIA, BMP-RIB, and BMP-RII primer pairs in human TM cells and tissues. All human TM cells and tissues expressed message for the BMP receptor complexes. Southern blots using specific probes verified that these were the expected PCR products. An alternate amplification product (350 bp) was detected in the BMP-RII PCR reaction. The alternate amplification product was present in all human TM cells and tissues. This alternate band is currently being identified to determine if it is an alternate spliced form of the receptor. Control reactions without cDNA did not result in amplification products (FIG. 7, lane C) indicating that reagents and primers were free of DNA or RNA contamination.

Figure 8:
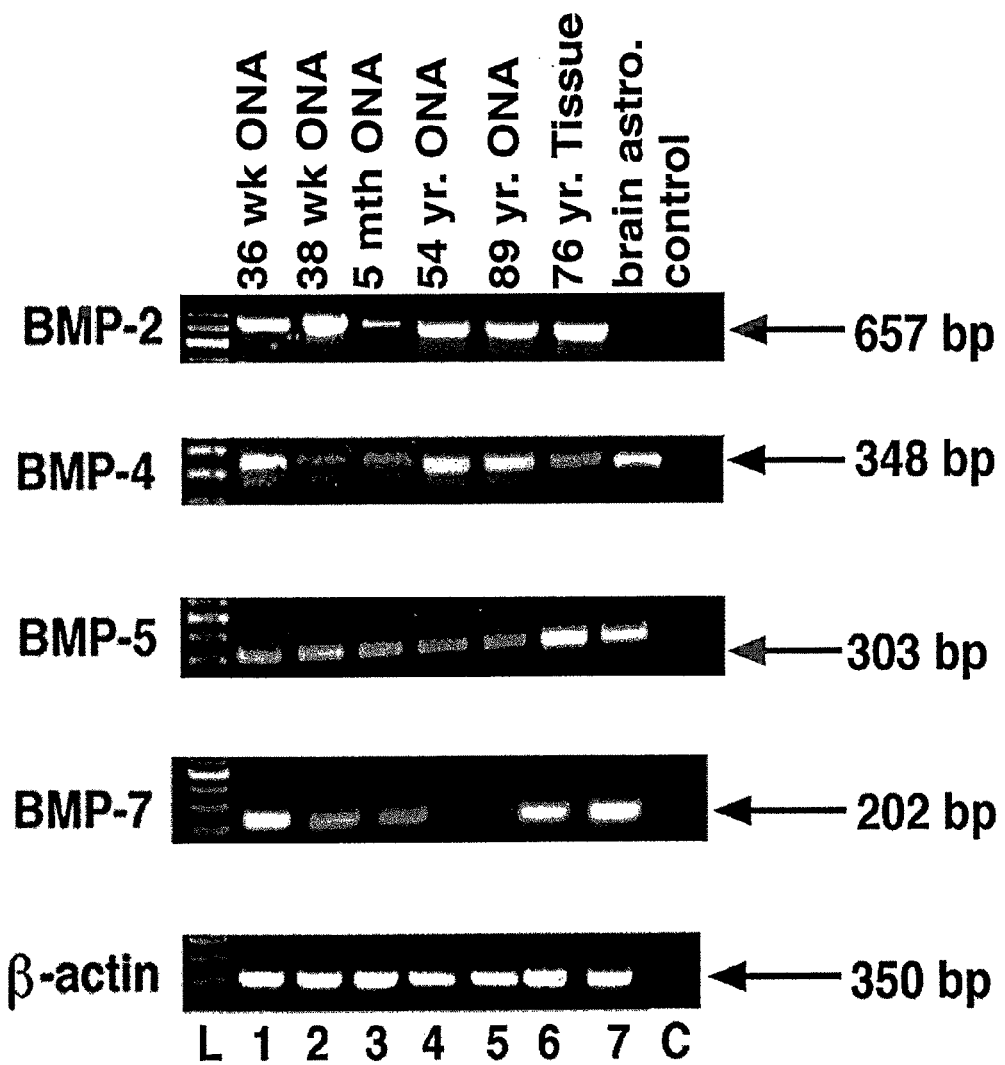
FIG. 8. BMP expression in human ONH astrocytes, ONH tissues, and human brain astrocytes. Ethidium bromide-stained agarose gel of PCR products from cDNA samples generated from RT-PCR analysis of BMP expression in human ONH astrocyte (lanes 1-5), ONH tissue (lane 6), and human brain astrocytes (lane 7). L=base pair markers. C=PCR negative control lane. β-actin was used as a positive RT-PCR internal control.

Expression of BMP and BMP receptor mRNA in human ONH cells and tissues: Amplification products of expected size for BMP-2, BMP-4, BMP-5 and BMP-7 primer pairs in human ONH astrocytes and ONH tissues are shown in FIG. 8. All ONH astrocytes and ONH tissue expressed message for the respective BMP. Human brain astrocytes were used as a positive control cell line. Southern blots using specific probes verified that these were the expected PCR products. With the exception of BMP-2, all other BMP were expressed by human brain astrocytes (FIG. 8, lane 7). Control reactions without cDNA did not result in amplification products (FIG. 8, lane C) indicating that reagents and primers were free of DNA or RNA contamination.

Figure 9:
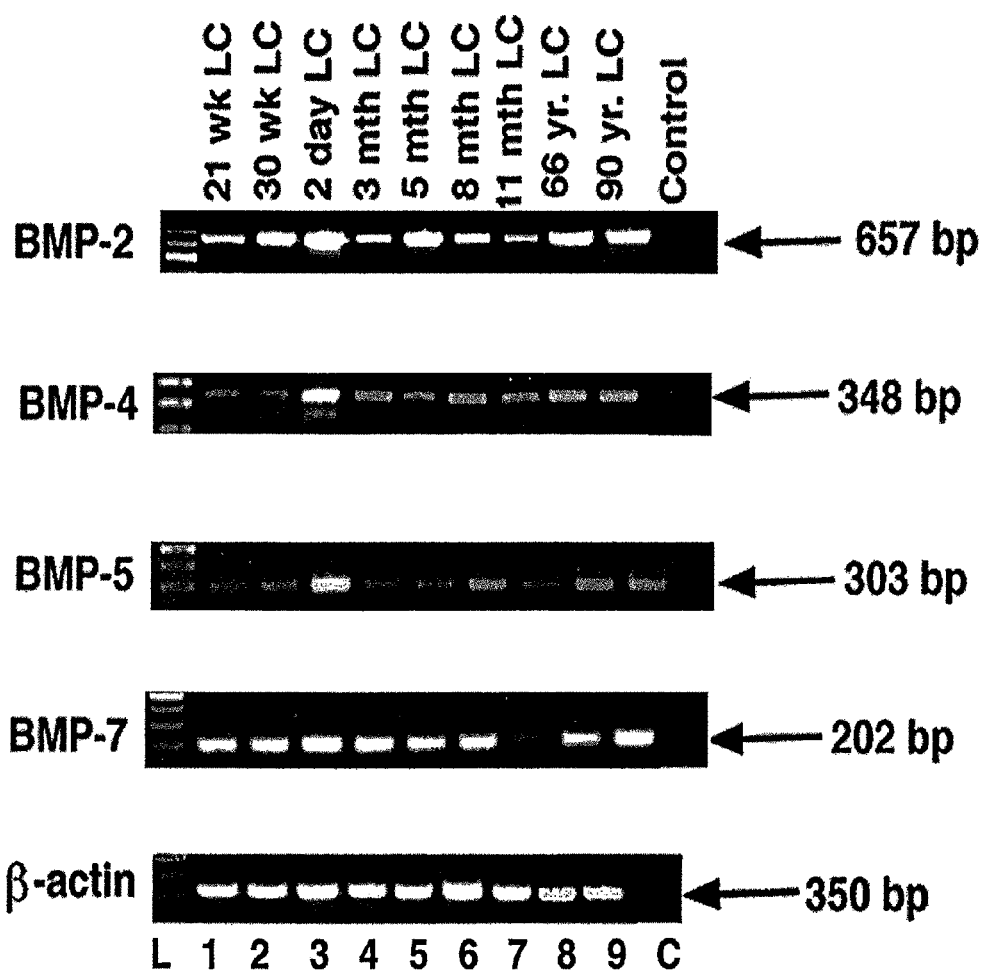
FIG. 9. BMP expression in human lamina cribrosa cell lines. Ethidium bromide-stained agarose gel of PCR products from cDNA samples generated from RT-PCR analysis of human lamina cribrosa cells (lanes 1-9). L=base pair markers. C=PCR negative control lane. β-actin was used as a positive RT-PCR internal control.

FIG. 9 shows the amplification products of expected sizes for BMP-2, BMP-4, BMP-5 and BMP-7 primer pairs in cultured human LC cells. All LC cell lines expressed message for each BMP. Southern blots using specific probes verified that these were the expected PCR products. Control reactions without cDNA did not result in amplification products (FIG. 9, lane C) indicating that reagents and primers were free of DNA or RNA contamination.

Figure 10:
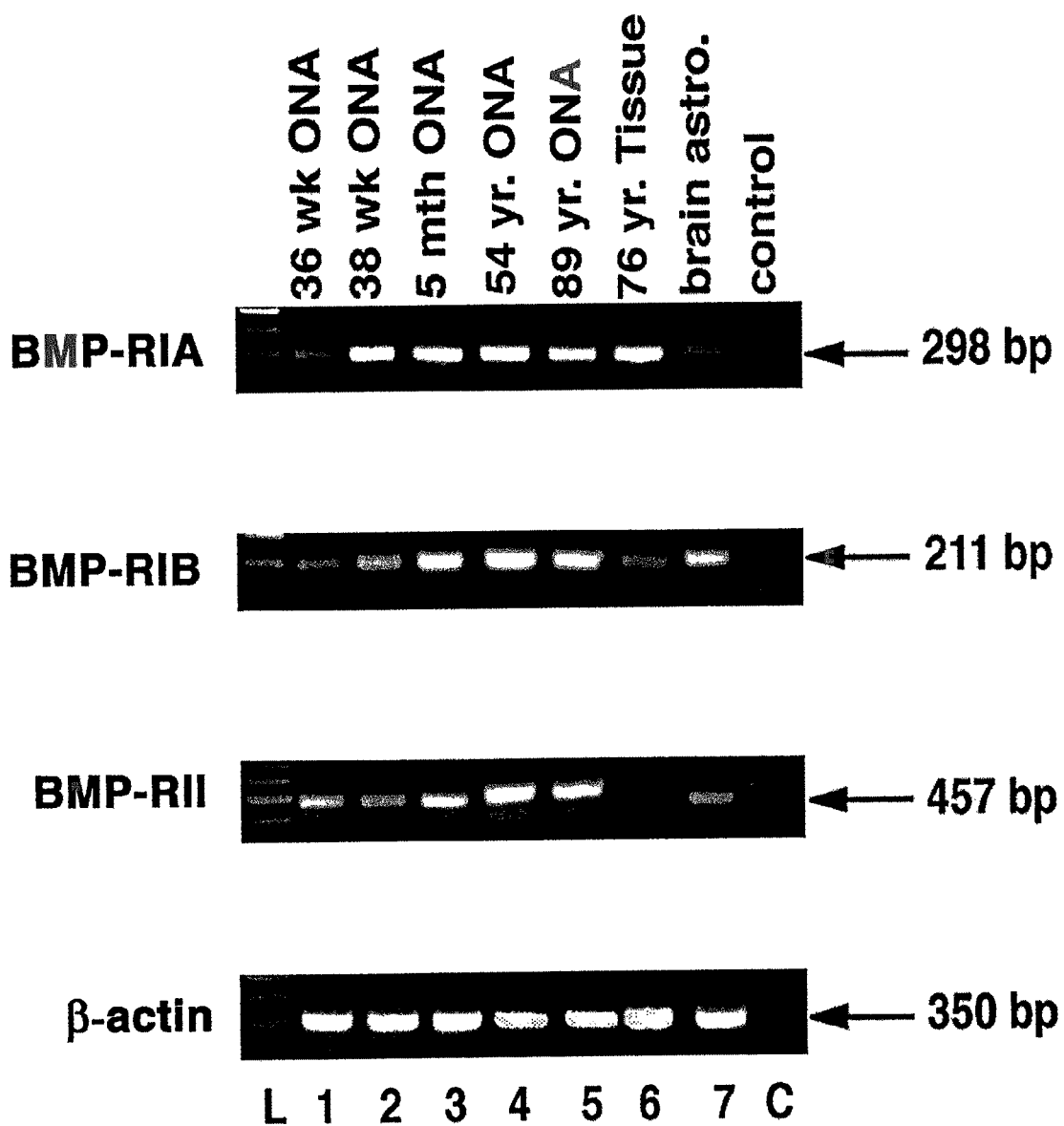
FIG. 10. BMP receptor expression in human ONH astrocytes, ONH tissues, and human brain astrocytes. Ethidium bromide-stained agarose gel of PCR products from cDNA samples generated from RT-PCR analysis of BMP receptor expression in human optic nerve head astrocytes (ONA) (lanes 1-5), ONH tissue (lane 6), and human brain astrocytes (lane 7). L=base pair markers. C=PCR negative control lane. β-actin was used as a positive RT-PCR control.

Amplification products of expected size for BMP-RIA, BMP-RIB, and BMP-RII primer pairs in human ONH astrocytes and ONH tissues are shown in FIG. 10. All ONH astrocyte cell lines and tissues expressed message for BMP-RIA and BMP-RIB. Southern blots using specific probes verified that these were the expected PCR products. With the exception of ONH tissue (FIG. 10, lane 6), BMP-RII was expressed by all ONH astrocyte cell lines. Message for all BMP receptors (FIG. 10, lane 7) was expressed by a human brain astrocyte cell line that served as a positive control. There appears to be a discrepancy in the expression of BMP-RII in ONH tissue and ONH cell lines. The reduced expression in ONH tissue may reflect a low level of expression. Control reactions without cDNA did not result in amplification products (FIG. 5, lane C) indicating that reagents and primers were free of DNA or RNA contamination.

Figure 11:
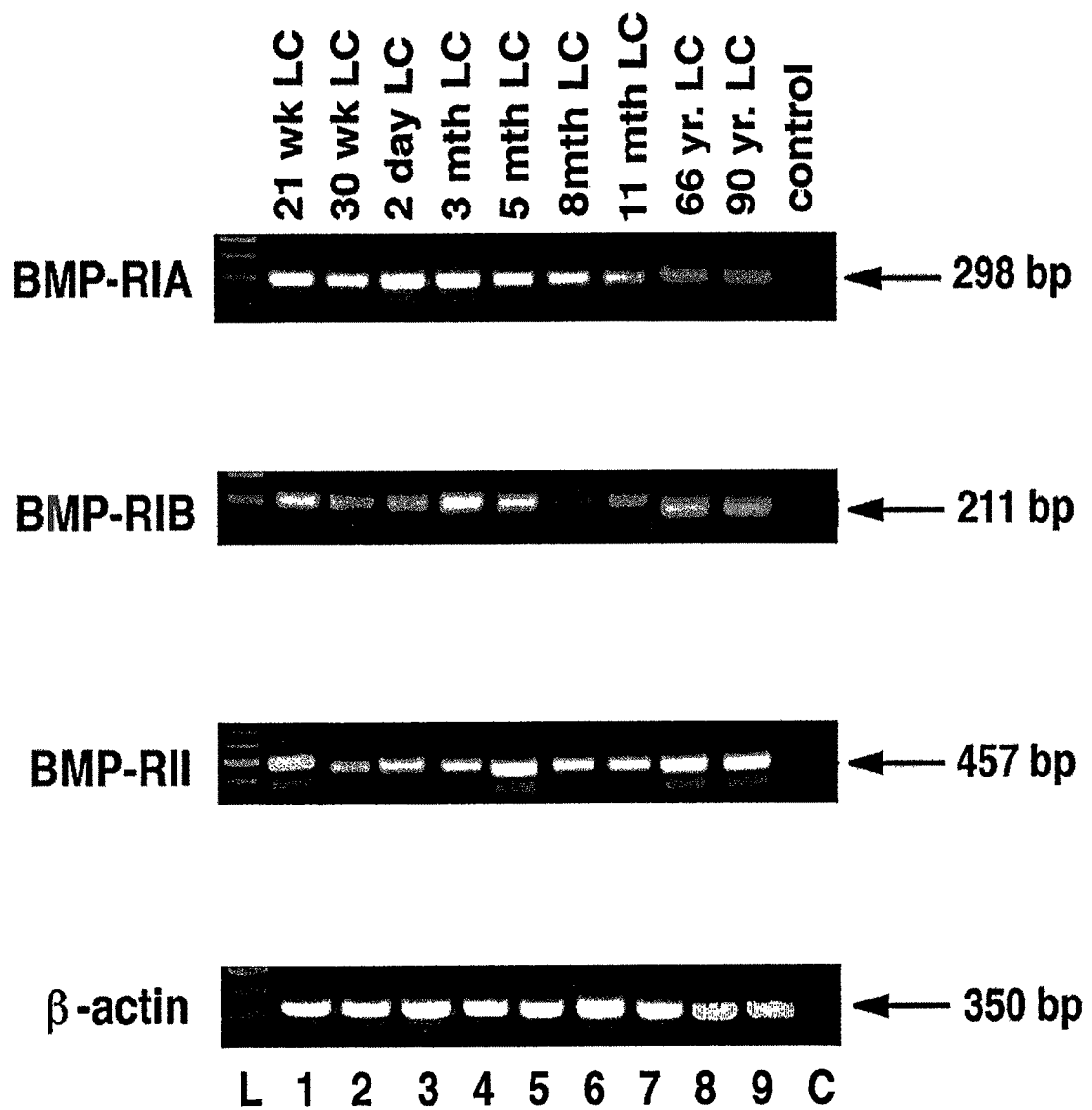
FIG. 11. BMP receptor expression in human lamina cribrosa cell lines. Ethidium bromide-stained agarose gel of PCR products from cDNA samples generated from RT-PCR analysis of human lamina cribrosa cells (lanes 1-9). L=base pair markers. C=PCR negative control lane. β-actin was used as a positive RT-PCR control.

FIG. 11 shows the amplification products of expected size for BMP-RIA, BMP-RIB, and BMP-RII primer pairs in cultured human LC cells. All LC cell lines expressed message for each BMP receptor. Southern blots using specific probes verified that these were the expected PCR products. Control reactions without cDNA did not result in amplification products (FIG. 11, lane C) indicating that reagents and primers were free of DNA or RNA contamination.

Figure 12:
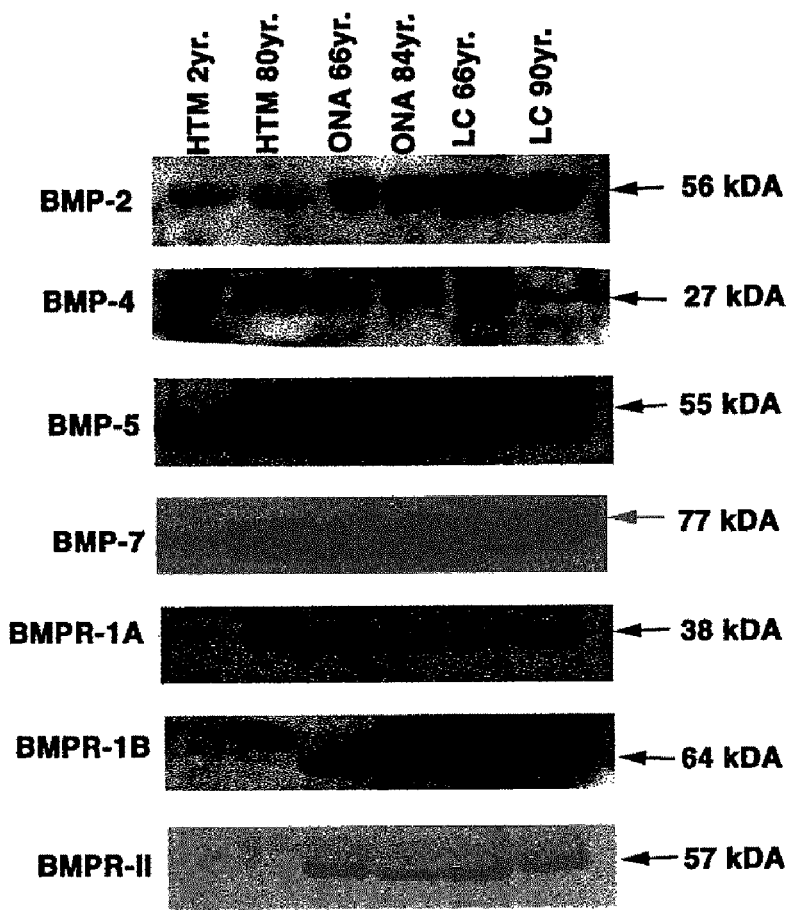
FIG. 12. Western immunoblot of BMP and BMP receptor expression in cultured human TM cells, optic nerve head astrocytes (ONA), and lamina cribrosa cells. Chemiluminescent detection of BMP proteins and BMP receptors in human trabecular meshwork cells (lanes 1-2), ONH astrocytes (lanes 3-4), and lamina cribrosa cells (lanes 5-6). Protein size indicated in kDa.

Expression of BMP proteins and BMP receptor proteins in human TM and ONH cells and tissues: FIG. 12 represents chemiluminescent immunoblot detection of BMP-2, BMP-4, BMP-5, BMP-7, BMP-RIA, BMP-RIB, and BMP-RII proteins in human TM and ONH cells and tissues. All cell lines studied expressed the respective BMP proteins. The BMP proteins were detected in cell lines the following molecular weights: 54-56 kDa for BMP-2, 25-27 kDa for BMP-4, 55-57 kDa for BMP-5, and 77 kDa for BMP-7. Multiple bands were detected for BMP-2 and BMP-4, which most likely represent glycosylated, and partially glycosylated forms of these BMPs as seen in other studies. However, we did not do glycosylation studies as they were beyond the scope of this study. The BMP receptor proteins were detected in cell lines at molecular weights: 38 kDa for BMP-RIA, 64 kDa for BMP-RIB, and 57 kDa for BMP-RII. Multiple bands were detected for BMP-RIB and BMP-RII in the TM cells, which most likely represent glycosylated, and partially glycosylated forms as seen in other studies. The expression levels of proteins for the BMP receptors appeared to be lower in the TM cells compared to ONH cells. For example BMP-RII was not detected in TM cells and BMP-RIB was greatly reduced.

Figure 13:
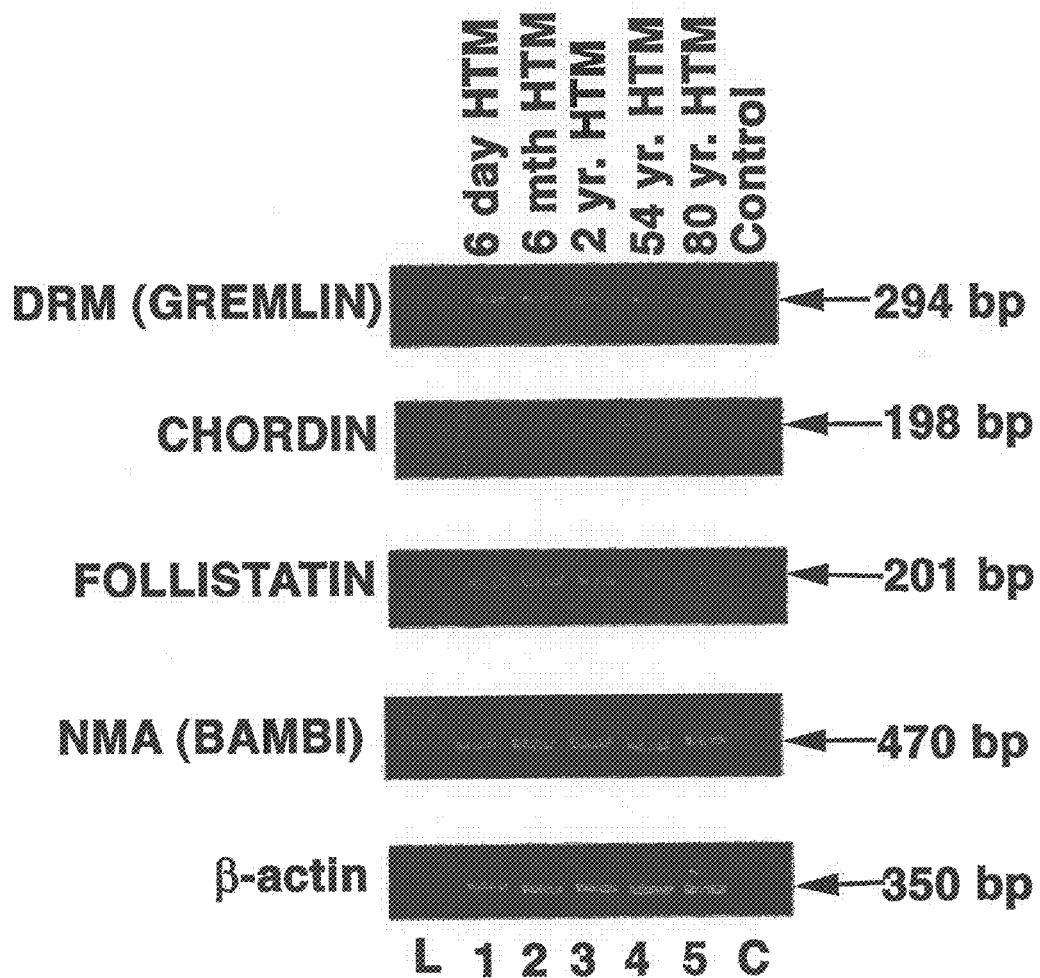
FIG. 13. BMP associated protein mRNA expression in human TM cells. Ethidium bromide-stained agarose gel of PCR products from cDNA samples generated from RT-PCR analysis of human TM cells (lanes 1-5). L=base pair markers. C=PCR negative control lane. β-actin was used as a positive RT-PCR internal control.

Expression of BMP associated protein mRNAs in cultured human TM cells and in human ONH cells: Amplification products of expected size for BMP associated protein primer pairs in human TM cell lines are shown in FIG. 13. Human TM cell lines expressed message for DRM (gremlin), chordin, follistatin, and NMA (BAMBI). Southern blots using specific probes verified that these were the expected PCR products. There was no apparent difference in message expression between cell lines. All human TM cells examined failed to express mRNA for the BMP associated proteins noggin and Cer-1. Control reactions without cDNA did not result in amplification products indicating that reagents and primers were free of DNA or RNA contamination.

Figure 14:
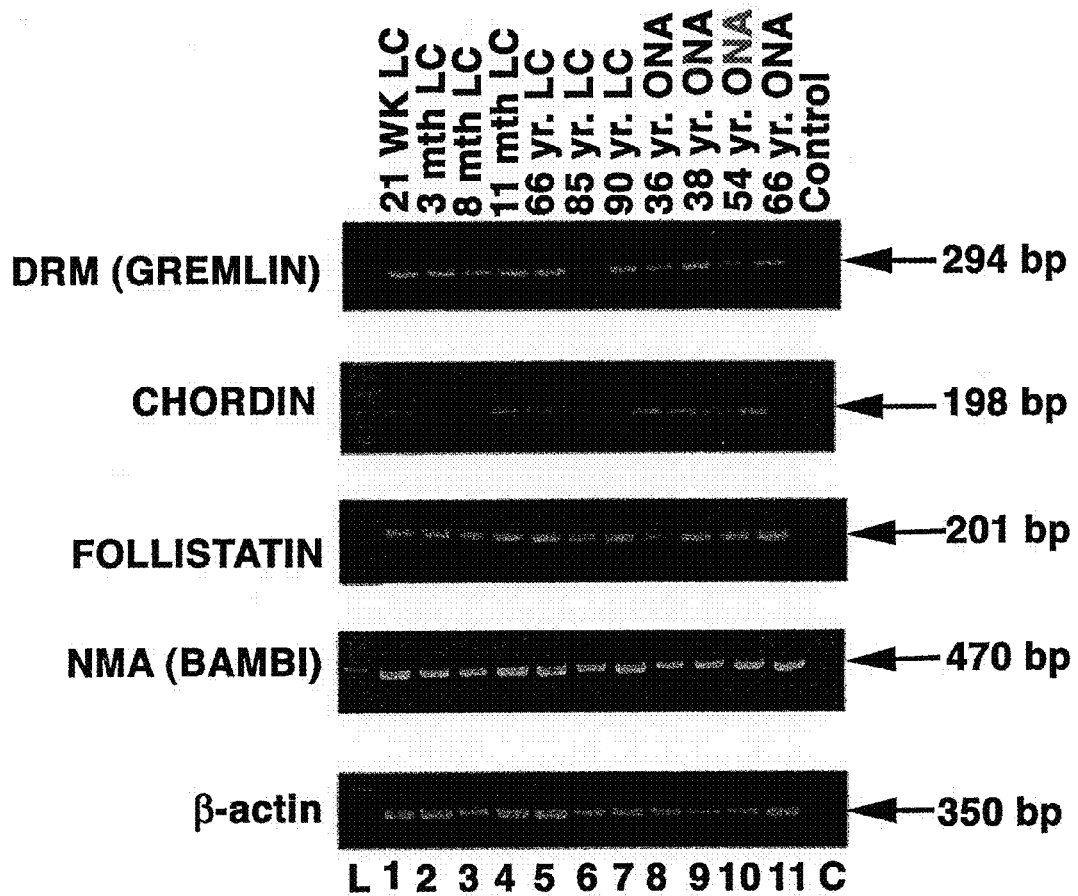
FIG. 14. BMP associated protein mRNA expression in human lamina cribrosa cells and ONH astrocytes. Ethidium bromide-stained agarose gel of PCR products from cDNA samples generated from RT-PCR analysis of lamina cribrosa (LC) cells (lanes 1-7) and ONH astrocytes (ONA) (lanes 8-11). L=base pair markers. C=PCR negative control lane. β-actin was used as a positive RT-PCR internal control.

Amplification products of expected size for BMP associated protein primer pairs in ONH astrocytes and LC cell lines are shown in FIG. 14. All ONH astrocytes and LC cell lines expressed message for DRM (gremlin), follistatin and NMA (BAMBI). Southern blots using specific probes verified that these were the expected PCR products. The majority of LC cells and ONH astrocytes expressed message for chordin. All human ONH astrocytes and LC cells examined failed to express mRNA for the BMP associated proteins noggin and Cer-1. Control reactions without cDNA did not result in amplification products indicating that reagents and primers were free of DNA and RNA contamination.

Figure 15:
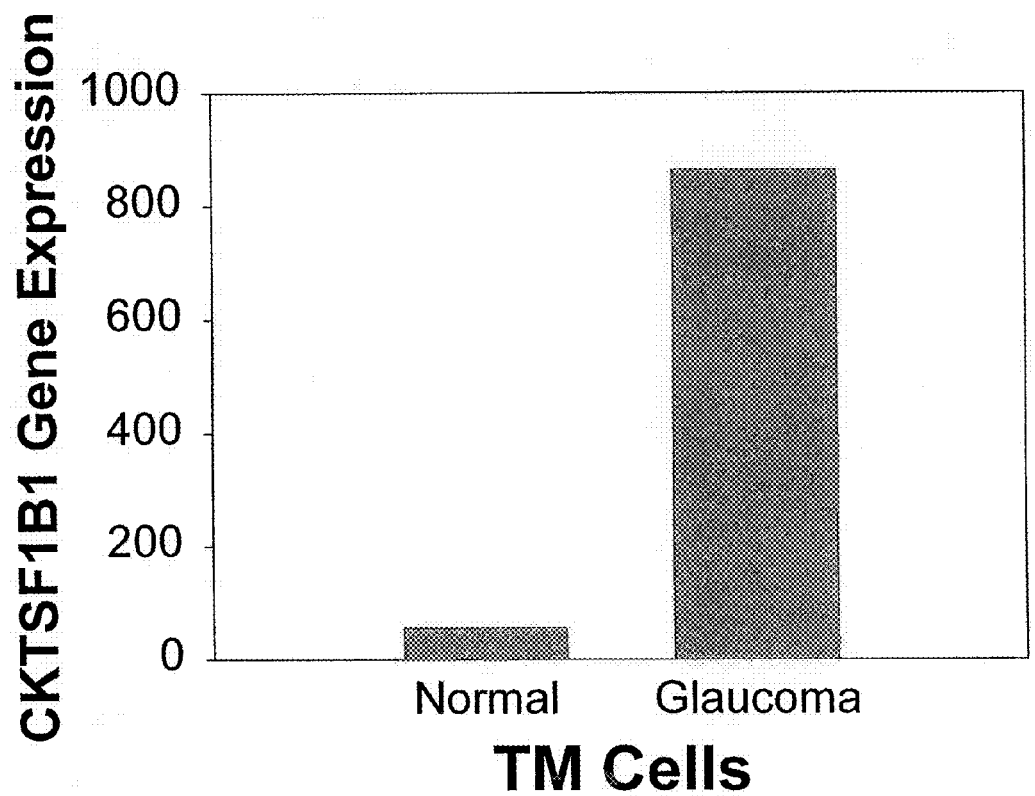
FIG. 15. Illustrates increased expression of the BMP antagonist gremlin (CKTSF1B1) in glaucomatous TM cells. Gene expression was assessed using Affymetrix gene arrays (Affymetrix gene chip U133A).

FIG. 15 shows increased expression of the BMP antagonist gremlin (CKTSF1B1) in glaucomatous TM cells. Gene expression was assessed using Affymetrix gene arrays (Affymetrix gene chip U133A).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

BOOKS

Birren, et al., GENOME ANALYSIS, Vol. 2, (1998).

Clark A F, Browder S, Steely H T, Wilson K, Cantu-Crouch D, McCartney M D, "Cell biology of the human lamina cribrosa," In Drance S M (ed). OPTIC NERVE IN GLAUCOMA. Kugler Publications, New York: pp. 79-105 (1995b).

Cummings, Michael R., HUMAN HEREDITY, Fourth Edition, (1997).

Grierson I, Calthorpe C M, "Characteristics of meshwork cells and age changes in the outflow system of the eye: their relevance to primary open angle glaucoma." In Mills K B (ed). GLAUCOMA. PROCEEDINGS OF THE FOURTH INTERNATIONAL SYMPOSIUM OF THE NORTHERN EYE INSTITUTE, Manchester, UK, New York, Pergamon: pp. 12-31 (1988).

Hernandez M, Gong H, "Extracellular matrix of the trabecular meshwork and optic nerve head." in Ritch R., Shields, M. B., Krupin, T. (eds). THE GLAUCOMAS, $2^{nd}$ ed. St Louis: Mosby-Year; pp. 213-249 (1996).

Jorde, et al., MEDICAL GENETICS, Second Edition, (1999).

Lutjen-Drecoll E., Rohen J. W., "Morphology of aqueous outflow pathways in normal and glaucomatous eyes," in Ritch R., Shields, M. B., Krupin, T. (eds). THE GLAUCOMAS, $2^{nd}$ ed. St Louis: Mosby-Year; pp. 89-123 (1996).

Strachan, et al., HUMAN MOLECULAR GENETICS, (1996).

Tripathi R C, Borisuth N S, Li, J, Tripathi B J, "Clinical implications of aqueous humor growth factors in glaucoma," in Ritch R., Shields, M. B., Krupin, T. (eds). THE GLAUCOMAS, $2^{nd}$ ed. St Louis: Mosby-Year; pp. 71-87 (1996).

Varma R, Minckler D, "Anatomy and pathophysiology of the retina and optic nerve." in Ritch R., Shields, M. B., Krupin, T. (eds). THE GLAUCOMAS, $2^{nd}$ ed. St Louis: Mosby-Year; pp. 139-175 (1996).

Vaughan, D. et al., In: GENERAL OPHTHALMOLOGY, Appleton & Lange, Norwalk, Conn., pp. 213-230 (1992).

OTHER PUBLICATIONS

Agarwal et al., *IOVS* 38(4):5563 (1997)

Agarwal R, Talati M, Lambert W, Clark A F, Wilson S E, Agarwal N, Wordinger R J, "*FAS-activated apoptosis and other apoptosis mediators in human trabecular meshwork cells,*" *Exp. Eye Res.* 68:583-590 (1999).

Astrom, A. K., Jin, D., Imamura, T., Roijer, E., Rosenzweig, B., Miyazono, K., ten Dijke, P., Stenman, G., *Mamm. Genome* 10(3):299-302 (1999).

Attisano L, Tuen Lee-Hoeflich S, "*The Smads,*" *Genome Biol.* 2:REVIEWS3010 (2001).

Bengtsson, B., *Br. J. Opthalmol.* 73:483-487 (1989).

Chang B, Smith R S, Peters M, Savinova D V, Hawes N L, Zabalata A, Nusinowitz S, Martin J E, Davisson M L, Sepko C L, Hogan B M L, John S W M, "*Haploinsufficient Bmp4 ocular phenotypes include anterior segment dysgenesis with elevated intraocular pressure,*" *BMC Genetics* 2:18 (2001).

Chundru R K, Agarwal R, Wordinger R J, Whitson J T, "*Detection of neurotrophins in human aqueous humor,*" *Invest. Opthalmol. Vis. Sci.* 41:S236 (2000).

Clark A F, Kawase K, English-Wright S, Lane D, Steely H T, Yamamoto T, Kitazawa Y, Kwon Y H, Fingert J H, Swiderski R E, Mullins R F, Hageman G S, Alward W L M, Sheffield V C, Stone E M, "*Expression of the glaucoma gene myocilin (MYOC) in the human optic nerve head,*" *FASEB J.* 15:1251-1253 (2001).

Clark A F, Lane D, Wilson K, Miggans S T, McCartney M D, "*Inhibition of dexamethasone-induced cytoskeletal changes in cultured human trabecular meshwork cells by tetrahydrocortisol,*" *Invest. Opthalmol. Vis. Sci.* 35:805-813 (1996).

Clark A F, Miggans S T, Wilson K, Browder S, McCartney M D, "*Cytoskeletal changes in cultured human glaucoma trabecular meshwork cells,*" *J. Glaucoma* 4:183-188 (1995c).

Clark A F, Steely H T, Dickerson J E, English-Wright S, Stropki K, McCartney M D, Jacobson N, Shepard A R, Clark J I, Matsushima H, Peskind E R, Leverenz J B, Wilkinson C W, Swiderski R E, Fingert J H, Sheffield V C, Stone E M, "*Glucocorticoid induction of the glaucoma gene MYOC in human and monkey trabecular meshwork cells and tissues,*" *Invest. Opthalmol. Vis. Sci.* 42:1769-1780 (2001b).

Clark A F, Wilson K, de Kater A W, Allingham R R, McCartney M D, "*Dexamethasone-induced ocular hypertension in perfusion-cultured human eyes,*" *Invest. Opthalmol. Vis. Sci.* 36:478-489 (1995a).

Clark A F, Wilson K, McCartney M D, Miggans S T, Kunkle M, Howe W, "*Glucocorticoid-induced formation of cross-linked actin networks in cultured human trabecular meshwork cells,*" *Invest. Opthalmol. Vis. Sci.* 35:281-294 (1994).

Dickerson J E, Steely H T, English-Wright S L, Clark A F, "*The effect of dexamethasone on integrin and laminin expression in cultured human trabecular meshwork cells,*" *Exp. Eye Res.* 66:731-738 (1998).

Dudley A T, Lyons K M, Robertson E J, "*A requirement for bone morphogenic protein-7 during development of the mammalian kidney and eye,*" *Genes Dev.* 9:2795-2807 (1995).

Furuta Y, Hogan B L, "*BMP4 is essential for lens induction in the mouse embryo,*" *Genes Dev.* 12:3764-3775 (1998).

Greve, M. et al., *Can. J. Ophthamol.* 28:201-206 (1993).

Giguère et al., *Cell* 46:645-652 (1986).

Hernandez M R, Andrzejewska W M, Neufeld A H, "*Changes in the extracellular matrix of the human optic nerve head in primary open-angle glaucoma,*" *Am. J. Opthalmol.* 109:180-188 (1990).

Hernandez M R, Pena J D, "*The optic nerve head in glaucomatous optic neuropathy,*" *Arch Opthalmol.* 115:389-395 (1997).

Hitchings, R. A., *Br. J. Ophthamol.* 77:326 (1993).

Hogan B L, "*Bone morphogenic proteins: multifunctional regulators of vertebrate development,*" *Genes Dev.* 10:1580-1594 (1996).

Hu D N, Ritch R, "*Hepatocyte growth factor is increased in the aqueous humor of glaucomatous eyes,*" *J. Glaucoma* 10:152-157 (2001).

Inatani M, Tanihara H, Katsuta H, Honjo M, Kido N, Honda Y, "*Transforming growth factor beta 2 levels in aqueous humor of glaucomatous eyes,*" *Graefes Arch. Clin. Exp. Opthalmol.* 239:109-113 (2001).

Itoh et al., *Eur. J. Biochem.* 267:6954-6967 (2000).

Jena N, Martin-Seisdedos C, McCue P, Croce C M, "*BMP7 null mutation in mice: developmental defects in skeleton, kidney, and eye,*" *Exp. Cell Res.* 230:28-37 (1997).

Kawabata et al., *Cytokine & Growth Factor Review,* 9:49-61 (1998).

Kerrigan L A, Zack D J, Quigley H A, Smith S D, Pease M E, "*TUNEL-positive ganglion cells in human primary open-angle glaucoma,*" *Arch. Opthalmol.* 115:1031-1035 (1997).

Lambert et al., *IOVS* 38(4):S162 (1997).

Lambert W, Agarwal R, Howe W, Clark A F, Wordinger R J, "*Neurotrophin and neurotrophin receptor expression by cells of the human lamina cribrosa,*" *Invest. Opthalmol. Vis. Sci.,* 42:2315-2323 (2001).

Leske, M. C. et al., *Amer. J. Epidemiol.* 113:1843-1846 (1986).

Liu et al., *IOVS* 40(4):5673 (1999).

Liu Y, Belayev L, Zhao W, Busto R, Saul I, Alonso O, Ginsberg M D, "*The effect of bone morphogenic protein-7 (BMP-7) on functional recovery, local cerebral glucose utilization and blood flow after transient focal cerebral ischemia in rats,*" *Brain Res.* 905:81-90 (2001).

Liu X, Lambert W, Agarwal R, Talati M, Cross W, Clark A F, Wordinger R J, "*Human trabecular meshwork cells express the ciliary neurotrophic factor (CNTF) tripartate receptor complex,*" *Exp. Eye Res.* 72:711-717 (2001).

Luo G, Gofmann C, Bronckers A L, Sohocki M, Bradley A, Karsenty G, "*BMP-7 is an inducer of nephrogenesis, and is also required for eye development and skeletal patterning,*" *Genes Dev.* 9:2808-2820 (1995).

McMahon, R., Murphy, M., Clarkson, M., Taal, M., Mackenzie, H. S., Godson, C., Martin, F., Brady, H. R., *J. Biol. Chem.* 275(14):9901-9904 (2000).

Miyazono, *J. Cell Science,* 113:1101-1109 (2000).

Mohan R R, Kim W J, Mohan R R, Chen L, Wilson S E, "*Bone morphogenic proteins 2 and 4 and their receptors in the adults human cornea,*" *Invest. Opthalmol. Vis. Sci.* 39:2626-2636 (1998).

Morrison J C, Dorman-Pease M E, Dunkelberger G R, Quigley H A, "*Optic nerve head extracellular matrix in primary optic atrophy and experimental glaucoma,*" *Arch. Opthalmol.* 108:1020-1024 (1990).

Murphy, M., Godson, C., Cannon, S., Kato, S., Mackenzie, H. S., Martin, F., Brady, H. R., *J. Biol. Chem.* 274(9):5830-5834 (1999).

Nickel J, Dreyer M K, Kirsch T, Sebold W, "*The crystal structure of BMP-2:BMPR-1A complex and the generation of BMP-2 antagonists,*" J. Bone & Joint Surgery 83-A (suppl 1):S1-57 (2001).

Nohno, T., Ishikawa, T., Saito, T., Hosokawa, K., Noji, S., Wolsing, D. H., Rosenbaum, J. S., *J. Biol. Chem.* 270(38): 22522-22526 (1995).

Nonner D, Barrett E F, Kaplan P, Barrett J N, "*Bone morphogenic proteins (BMP6 and BMP7) enhance the protective effect of neurotrophins on cultured septal cholinergic neurons during hypoglycemia,*" J. Neurochem. 77:691-699 (2001).

Obata H, Kaji Y, Yamada H, Kato M, Tsuru T, Yamashita H, "*Expression of transforming growth factor-beta superfamily receptors in rat eyes,*" Acta. Opthalmol. Scand. 77:151-156 (1999).

Pang I-H, McCartney M D, Steely H T, Clark A F, "*Human ocular perfusion organ culture: a versatile ex vivo model for glaucoma research,*" J. Glaucoma 9:468-479 (2000).

Pena J D, Taylor A W, Ricard C S, Vidal I, Hernandez M R, "*Transforming growth factor beta isoforms in human optic nerve heads,*" Br. J. Opthalmol. 83:209-218 (1999).

Picht G, Welge-Luessen U, Grehn F, Lutjen-Drecoll E, "*Transforming growth factor beta 2 levels in the aqueous humor in different types of glaucoma and the relation to filtering bleb development,*" Graefes Arch. Clin. Exp. Opthalmol. 239:199-207 (2001).

Quigley H A, McKinnon S J, Zack D J, Pease M E, Kerrigan-Baumrind L A, Kerrigan D F, Mitchell R S, "*Retrograde axonal transport of BDNF in retinal ganglion cells is blocked by acute IOP elevation in rats,*" Invest. Opthalmol. Vis. Sci. 41:3460-3466 (2000).

Quigley H A, "*Neuronal death in glaucoma,*" Prog. Retin. Eye Res. 18:39-57 (1999).

Quigley H A, Nickells R W, Kerrigan L A, Pease M E, Thibault D J, Zack D J, "*Retinal ganglion cell death in experimental glaucoma and after axotomy occurs by apoptosis,*" Invest. Opthalmol. Vis. Sci. 36:774-786 (1995).

Reddi A H, "*Bone morphonegetic proteins: an unconventional approach to isolation of to first mammalian morphogens,*" Cytokine Growth Factor Rev. 8:11-20 (1997).

Reddi A H, "*Bone morphogenic proteins and skeletal development: the kidney-bone connection,*" Pediatr. Nephrol. 14:598-601 (2000).

Rohen J W, "*Why is intraocular pressure elevated in chronic simple glaucoma? Anatomical considerations.*" Opthalmology 90:758-765 (1983).

Steely H T, Browder S L, Julian M B, Miggans S T, Wilson K L, Clark A F, "*The effects of dexamethasone on fibronectin expression in cultured human trabecular meshwork cells,*" Invest. Opthalmol. Vis. Sci. 33: 2242-2250 (1992).

Steely H T, English-Wright S L, Clark A F, "*Similarity of protein expression in trabecular meshwork and lamina cribrosa: implications for glaucoma,*" Exp. Eye Res. 70:17-30 (2000).

Strong, N. P., *Ophthal. Physiol. Opt.* 12:3-7 (1992).

ten Dijke, P. P., Ichijo, H., Franzen, P., Schulz, P., Saras, J., Toyoshima, H., Heldin, C. H., Miyazono, K., *Oncogene* 8(10):2879-2887 (1993).

Tripathi R C, Borisuth N S, Kolli S P, Tripathi B J, "*Trabecular cells express receptors that bind TGF-beta 1 and TGF-beta 2: a qualitative and quantitative characterization,*" Invest. Opthalmol. Vis. Sci. 34:260-263 (1993b).

Tripathi R C, Borisuth N S, Tripathi B J, "*Detection, quantification, and significance of basic fibroblast growth factor in the aqueous humor of man, cat, dog and pig,*" Exp. Eye Res. 54:447-454 (1992).

Tripathi R C, Borisuth N S, Tripathi B J, Fang V S, "*Analysis of human aqueous humor for epidermal growth factor,*" Exp. Eye Res. 53:407-409 (1991).

Tripathi R C, Chan W F, Li J, Tripathi B J, "*Trabecular cells express the TFG-beta 2 gene and secrete the cytokine,*" Exp. Eye Res. 58:523-528 (1994a).

Tripathi R C, Li J, Borisuth N S, Tripathi B J, "*Trabecular cells of the eye express messenger RNA for transforming growth factor-beta 1 and secrete this cytokine,*" Invest. Opthalmol. Vis. Sci. 34:2562-2569 (1993a).

Tripathi R C, Li J, Chan W F, Tripathi B J, "*Aqueous humor in glaucomatous eyes contains an increased level of TFG-beta 2,*" Exp. Eye Res. 59:723-727 (1994c).

Tripathi R C, Li J, Tripathi B J, "*Immunolocalization of bFGF in the trabecular meshwork and detection of its mRNA in trabecular cells,*" Exp. Eye Res. 58:503-507 (1994b).

Trousse F, Esteve P, Bovolenta P, "*BMP4 mediates apoptotic cell death in the developing chick eye,*" J. Neurosci. 21:1292-1301 (2001).

Tuck, M. W. et al., *Ophthal. Physiol. Opt.* 13:227-232 (1993).

Vernon, S. A., *Eye* 7:134-137 (1993).

Von Bubnoff A, Cho K W, "*Intracellular BMP signaling regulation in vertebrates: pathway or network?*" Dev. Biol. 239:1-14 (2001).

Wang W-H, McNatt L G, Shepard A R, Jacobson N, Nishimura D Y, Stone E M, Sheffield V C, Clark A F, "*Optimal procedure for extracting RNA from human ocular tissues and expression profiling of the congenital glaucoma gene FOXC1 using quantitative RT-PCR,*" Molecular Vision 7:89-94 (2001).

Wilson K, McCartney M D, Miggans S T, Clark A F, "*Dexamethasone induced ultrastructural changes in cultured human trabecular meshwork cells,*" Current Eye Research 12:783-793 (1993).

Wordinger et al., *IOVS* 40(4):S504 (1999a).

Wordinger R J, Agarwal R, Talati M, Fuller J, Lambert W, Calrk A F, "*Expression of bone morphogenic proteins (BMP), BMP receptors, and BMP associated proteins in human trabecular meshwork and optic nerve head cells and tissues,*" Molec. Vision 8:241-256 (2002).

Wordinger R J, Clark A F, Agarwal R, Lambert W, McNatt L, Wilson S E, Qu E, Fung B K-K, "*Cultured human trabecular meshwork cells express functional growth factor receptors,*" Invest. Opthalmol. Vis. Sci. 39: 1575-1589 (1998).

Wordinger R J, Clark A F, Agarwal R, Lambert W, Wilson S E, "*Expression of alternatively spliced growth factor receptor isoforms in the human trabecular meshwork,*" Invest. Opthalmol. Vis. Sci. 40:242-247 (1999b).

Wordinger R J, Lambert W, Agarwal R, Talati M, Clark A F, "*Human trabecular meshwork cells secrete neurotrophins and express neurotrophin receptors (Trk),*" Invest. Opthalmol. Vis. Sci. 41:3833-3841 (2000).

Yamashita H, Ten Dijke P, Heldin C H, Miyazono K, "*Bone morphogenic protein receptors,*" Bone 19:569-574 (1996).

You L, Kruse F E, Pohl J, Volcker H E, "*Bone morphogenic proteins and growth and differentiation factors in the human cornea,*" Invest. Opthalmol. Vis. Sci. 40:296-311 (1999).

Zhang D, Mehler M F, Song Q, Kessler J A, "*Development of bone morphogenic protein receptors in the nervous system and possible roles in regulating trkC expression,*" J. Neurosci. 18:3314-3326 (1998).

We claim:

1. A method for treating glaucoma comprising administering to a patient in need thereof a composition comprising human bone morphogenic protein 7 (hBMP7).

* * * * *

SEQUENCE LISTING

<160> NUMBER OF SEQ ID NOS: 56

<210> SEQ ID NO 1
<211> LENGTH: 1547
<212> TYPE: DNA
<213> ORGANISM: homo sapiens

<400> SEQUENCE: 1

```
ggggacttct tgaacttgca gggagaataa cttgcgcacc ccactttgcg ccggtgcctt      60
tgccccagcg gagcctgctt cgccatctcc gagccccacc gccctccac tcctcggcct      120
tgcccgacac tgagacgctg ttcccagcgt gaaaagagag actgcgcggc cggcacccgg     180
gagaaggagg aggcaaagaa aaggaacgga cattcggtcc ttgcgccagg tcctttgacc     240
agagttttc catgtggacg ctctttcaat ggacgtgtcc ccgcgtgctt cttagacgga      300
ctgcggtctc ctaaaggtcg accatggtgg ccgggacccg ctgtcttcta gcgttgctgc     360
ttccccaggt cctcctgggc ggcgcggctg gcctcgttcc ggagctgggc cgcaggaagt     420
tcgcggcggc gtcgtcgggc cgcccctcat cccagccctc tgacgaggtc ctgagcgagt     480
tcgagttgcg gctgctcagc atgttcggcc tgaaacagag acccaccccc agcagggacg     540
ccgtggtgcc cccctacatg ctagacctgt atcgcaggca ctcaggtcag ccgggctcac     600
ccgcccccaga ccaccggttg gagagggcag ccagccgagc caacactgtg cgcagcttcc   660
accatgaaga tctttggaa gaactaccag aaacgagtgg gaaaacaacc cggagattct     720
tctttaattt aagttctatc cccacggagg agtttatcac ctcagcagag cttcaggttt    780
tccgagaaca gatgcaagat gctttaggaa acaatagcag tttccatcac cgaattaata    840
tttatgaaat cataaaacct gcaacagcca actcgaaatt ccccgtgacc agacttttgg    900
acaccaggtt ggtgaatcag aatgcaagca ggtgggaaag ttttgatgtc accccgctg    960
tgatgcggtg gactgcacag ggacacgcca accatggatt cgtggtggaa gtggcccact  1020
tggaggagaa acaaggtgtc tccaagagac atgttaggat aagcaggtct ttgcaccaag  1080
atgaacacag ctggtcacag ataaggccat tgctagtaac ttttggccat gatggaaaag  1140
ggcatcctct ccacaaaaga gaaaaacgtc aagccaaaca caaacagcgg aaacgcctta  1200
agtccagctg taagagacac cctttgtacg tggacttcag tgacgtgggg tggaatgact  1260
ggattgtggc tccccgggg tatcacgcct tttactgcca cggagaatgc ccttttcctc   1320
tggctgatca tctgaactcc actaatcatg ccattgttca gacgttggtc aactctgtta  1380
actctaagat tcctaaggca tgctgtgtcc cgacagaact cagtgctatc tcgatgctgt  1440
accttgacga gaatgaaaag gttgtattaa agaactatca ggacatggtt gtggagggtt  1500
gtgggtgtcg ctagtacagc aaaattaaat acataaatat atatata               1547
```

<210> SEQ ID NO 2
<211> LENGTH: 396
<212> TYPE: PRT
<213> ORGANISM: homo sapiens

<400> SEQUENCE: 2

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45
```

```
Val Leu Ser Glu Phe Glu Leu Arg Leu Leu Ser Met Phe Gly Leu Lys
 50                  55                  60

Gln Arg Pro Thr Pro Ser Arg Asp Ala Val Val Pro Pro Tyr Met Leu
 65                  70                  75                  80

Asp Leu Tyr Arg Arg His Ser Gly Gln Pro Gly Ser Pro Ala Pro Asp
                 85                  90                  95

His Arg Leu Glu Arg Ala Ala Ser Arg Ala Asn Thr Val Arg Ser Phe
                100                 105                 110

His His Glu Glu Ser Leu Glu Glu Leu Pro Glu Thr Ser Gly Lys Thr
                115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
                180                 185                 190

Asp Thr Arg Leu Val Asn Gln Asn Ala Ser Arg Trp Glu Ser Phe Asp
                195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
                260                 265                 270

Gly His Pro Leu His Lys Arg Glu Lys Arg Gln Ala Lys His Lys Gln
                275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
                340                 345                 350

Asn Ser Lys Ile Pro Lys Ala Cys Cys Val Pro Thr Glu Leu Ser Ala
                355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 3
<211> LENGTH: 1946
<212> TYPE: DNA
<213> ORGANISM: homo sapiens

<400> SEQUENCE: 3
gaaagcgagg gagggaaaga ggaggaagga agatgcgaga aggcagagga ggagggaggg      60
agggaaggag cgcggagccc ggcccggaag ctaggtgagt gtggcatccg agctgaggga     120
cgcgagcctg agacgccgct gctgctccgg ctgagtatct agcttgtctc cccgatggga     180
```

```
ttcccgtcca agctatctcg agcctgcagc gccacagtcc ccggccctcg cccaggttca    240
ctgcaaccgt tcagaggtcc ccaggagctg ctgctggcga gcccgctact gcagggacct    300
atggagccat tccgtagtgc catcccgagc aacgcactgc tgcagcttcc ctgagccttt    360
ccagcaagtt tgttcaagat ggctgtcaa gaatcatgga ctgttattat atgccttgtt     420
ttctgtcaag acaccatgat tcctggtaac cgaatgctga tggtcgtttt attatgccaa    480
gtcctgctag gaggcgcgag ccatgctagt ttgatacctg agacggggaa gaaaaaagtc    540
gccgagattc agggccacgc gggaggacgc cgctcagggc agagccatga gctcctgcgg    600
gacttcgagg cgacacttct gcagatgttt gggctgcgcc gccgcccgca gcctagcaag    660
agtgccgtca ttccggacta catgcgggat ctttaccggc ttcagtctgg ggaggaggag    720
gaagagcaga tccacagcac tggtcttgag tatcctgagc gcccggccag ccgggccaac    780
accgtgagga gcttccacca cgaagaacat ctggagaaca tcccagggac cagtgaaaac    840
tctgcttttc gtttcctctt taacctcagc agcatccctg agaacgaggc gatctcctct    900
gcagagcttc ggctcttccg ggagcaggtg gaccagggcc ctgattggga aggggcttc     960 caccgtataa acatttatga ggttatgaag cccccagcag aagtggtgcc tgggcacctc   1020
atcacacgac tactggacac gagactggtc caccacaatg tgacacggtg gaaactttt   1080 gatgtgagcc ctgcggtcct tcgctggacc cgggagaagc agccaaacta tgggctagcc   1140
attgaggtga ctcacctcca tcagactcgg acccaccagg gccagcatgt caggattagc   1200
cgatcgttac tcaagggag tgggaattgg gcccagctcc ggcccctcct ggtcaccttt    1260
ggccatgatg gccggggcca tgccttgacc cgacgccgga gggccaagcg tagccctaag   1320
catcactcac agcgggccag gaagaagaat aagaactgcc ggcgccactc gctctatgtg   1380
gacttcagcg atgtgggctg gaatgactgg attgtggccc caccaggcta ccaggccttc   1440
tactgccatg gggactgccc ctttccactg gctgaccacc tcaactcaac caaccatgcc   1500
attgtgcaga ccctggtcaa ttctgtcaat tccagtatcc ccaaagcctg ttgtgtgccc   1560
actgaactga gtgccatctc catgctgtac ctggatgagt atgataaggt ggtactgaaa   1620
aattatcagg agatggtagt agagggatgt gggtgccgct gagatcaggc agtccttgag   1680
gatagacaga tatacacacc acacacacac accacataca ccacacacac acgttcccat   1740
ccactcaccc acacactaca cagactgctt cctttatagct ggacttttat ttaaaaaaaa   1800
aaaaaaaaaa atgaaaaaaa tccctaaaca ttcaccttga ccttatttat gactttacgt    1860
gcaaatgttt tgaccatatt gatcatatat tttgacaaaa tatatttata actacgtatt    1920
aaaagaaaaa aataaaatga gtcatt                                         1946
```

<210> SEQ ID NO 4
<211> LENGTH: 408
<212> TYPE: PRT
<213> ORGANISM: homo sapiens

<400> SEQUENCE: 4

```
Met Ile Pro Gly Asn Arg Met Leu Met Val Val Leu Leu Cys Gln Val
1               5                  10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60
```

```
Phe Gly Leu Arg Arg Arg Pro Gln Pro Ser Lys Ser Ala Val Ile Pro
 65                  70                  75                  80

Asp Tyr Met Arg Asp Leu Tyr Arg Leu Gln Ser Gly Glu Glu Glu Glu
                 85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
                180                 185                 190

Gly His Leu Ile Thr Arg Leu Leu Asp Thr Arg Leu Val His His Asn
            195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
                260                 265                 270

Val Thr Phe Gly His Asp Gly Arg Gly His Ala Leu Thr Arg Arg Arg
            275                 280                 285

Arg Ala Lys Arg Ser Pro Lys His His Ser Gln Arg Ala Arg Lys Lys
        290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 5
<211> LENGTH: 2153
<212> TYPE: DNA
<213> ORGANISM: homo sapiens

<400> SEQUENCE: 5
ctggtatatt tgtgcctgct ggaggtggaa ttaacagtaa gaaggagaaa gggattgaat      60
ggacttacag gaaggatttc aagtaaattc agggaaacac atttacttga atagtacaac     120
ctagagtatt attttacact aagacgacac aaaagatgtt aaagttatca ccaagctgcc     180
```

```
ggacagatat atattccaac accaaggtgc agatcagcat agatctgtga ttcagaaatc    240
aggatttgtt ttggaaagag ctcaagggtt gagaagaact caaaagcaag tgaagattac    300
tttgggaact acagtttatc agaagatcaa cttttgctaa ttcaaatacc aaaggcctga    360
ttatcataaa ttcatatagg aatgcatagg tcatctgatc aaataatatt agccgtcttc    420
tgctacatca atgcagcaaa aactcttaac aactgtggat aattggaaat ctgagtttca    480
gctttcttag aaataactac tcttgacata ttccaaaata tttaaaatag gacaggaaaa    540
tcggtgagga tgttgtgctc agaaatgtca ctgtcatgaa aaataggtaa atttgttttt    600
tcagctactg ggaaactgta cctcctagaa ccttaggttt ttttttttt aagaggacaa    660 gaaggactaa aaatatcaac ttttgctttt ggacaaaaat gcatctgact gtattttac    720 ttaagggtat tgtgggtttc ctctggagct gctgggttct agtgggttat gcaaaaggag    780
gtttgggaga caatcatgtt cactccagtt ttatttatag aagactacgg aaccacgaaa    840
gacgggaaat acaaagggaa attctctcta tcttgggttt gcctcacaga cccagaccat    900
tttcacctgg aaaacaagcg tcctctgcac ctctctttat gctggatctc tacaatgcca    960
tgaccaatga agaaaatcct gaagagtcgg agtactcagt aagggcatcc ttggcagaag   1020
agaccagagg ggcaagaaag ggatacccag cctctcccaa tgggtatcct cgtcgcatac   1080
agttatctcg gacgactcct ctgaccaccc agagtcctcc tctagccagc tccatgata    1140 ccaactttct gaatgatgct gacatggtca tgagctttgt caacttagtt gaaagagaca   1200
aggatttttc tcaccagcga aggcattaca agaatttcg atttgatctt acccaaattc    1260
ctcatggaga ggcagtgaca gcagctgaat tccggatata caaggaccgg agcaacaacc   1320
gatttgaaaa tgaaacaatt aagattagca tatatcaaat catcaaggaa tacacaaata   1380
gggatgcaga tctgttcttg ttagacacaa gaaaggccca agctttagat gtgggttggc   1440
ttgtctttga tatcactgtg accagcaatc attgggtgat taatccccag aataatttgg   1500
gcttacagct ctgtgcagaa acaggggatg gacgcagtat caacgtaaaa tctgctggtc   1560
ttgtgggaag acagggacct cagtcaaaac aaccattcat ggtggccttc ttcaaggcga   1620
gtgaggtact tcttcgatcc gtgagagcag ccaacaaacg aaaaaatcaa aaccgcaata   1680
aatccagctc tcatcaggac tcctccagaa tgtccagtgt tggagattat aacacaagtg   1740
agcaaaaaca agcctgtaag aagcacgaac tctatgtgag cttccgggat ctgggatggc   1800
aggactggat tatagcacca gaaggatacg ctgcattta ttgtgatgga aatgttctt     1860 ttccacttaa cgcccatatg aatgccacca accacgctat agttcagact ctggttcatc   1920
tgatgtttcc tgaccacgta ccaaagcctt gttgtgctcc aaccaaatta atgccatct    1980 ctgttctgta ctttgatgac agctccaatg tcattttgaa aaaatataga aatatggtag   2040
tacgctcatg tggctgccac taatattaaa taatattgat aataacaaaa agatctgtat   2100
taaggtttat ggctgcaata aaaagcatac tttcagacaa acagaaaaaa aaa            2153
```

<210> SEQ ID NO 6
<211> LENGTH: 454
<212> TYPE: PRT
<213> ORGANISM: homo sapiens

<400> SEQUENCE: 6

```
Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
            20                  25                  30
```

```
His Val His Ser Ser Phe Ile Tyr Arg Arg Leu Arg Asn His Glu Arg
            35                  40                  45

Arg Glu Ile Gln Arg Glu Ile Leu Ser Ile Leu Gly Leu Pro His Arg
         50                  55                  60

Pro Arg Pro Phe Ser Pro Gly Lys Gln Ala Ser Ala Pro Leu Phe
 65                  70                  75                  80

Met Leu Asp Leu Tyr Asn Ala Met Thr Asn Glu Glu Asn Pro Glu Glu
                85                  90                  95

Ser Glu Tyr Ser Val Arg Ala Ser Leu Ala Glu Glu Thr Arg Gly Ala
             100                 105                 110

Arg Lys Gly Tyr Pro Ala Ser Pro Asn Gly Tyr Pro Arg Arg Ile Gln
             115                 120                 125

Leu Ser Arg Thr Thr Pro Leu Thr Thr Gln Ser Pro Pro Leu Ala Ser
         130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                 165                 170                 175

Tyr Lys Glu Phe Arg Phe Asp Leu Thr Gln Ile Pro His Gly Glu Ala
             180                 185                 190

Val Thr Ala Ala Glu Phe Arg Ile Tyr Lys Asp Arg Ser Asn Asn Arg
         195                 200                 205

Phe Glu Asn Glu Thr Ile Lys Ile Ser Ile Tyr Gln Ile Ile Lys Glu
210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
             245                 250                 255

Asn His Trp Val Ile Asn Pro Gln Asn Asn Leu Gly Leu Gln Leu Cys
         260                 265                 270

Ala Glu Thr Gly Asp Gly Arg Ser Ile Asn Val Lys Ser Ala Gly Leu
     275                 280                 285

Val Gly Arg Gln Gly Pro Gln Ser Lys Gln Pro Phe Met Val Ala Phe
     290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser Ser His Gln Asp Ser Ser
             325                 330                 335

Arg Met Ser Ser Val Gly Asp Tyr Asn Thr Ser Glu Gln Lys Gln Ala
             340                 345                 350

Cys Lys Lys His Glu Leu Tyr Val Ser Phe Arg Asp Leu Gly Trp Gln
             355                 360                 365

Asp Trp Ile Ile Ala Pro Glu Gly Tyr Ala Ala Phe Tyr Cys Asp Gly
     370                 375                 380

Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
             405                 410                 415

Pro Cys Cys Ala Pro Thr Lys Leu Asn Ala Ile Ser Val Leu Tyr Phe
         420                 425                 430

Asp Asp Ser Ser Asn Val Ile Leu Lys Lys Tyr Arg Asn Met Val Val
         435                 440                 445

Arg Ser Cys Gly Cys His
```

<210> SEQ ID NO 7
<211> LENGTH: 1878
<212> TYPE: DNA
<213> ORGANISM: homo sapiens

<400> SEQUENCE: 7

| | | | | | |
|---|---|---|---|---|---|
| gggcgcagcg | gggcccgtct | gcagcaagtg | accgacggcc | gggacggccg | cctgcccct | 60 |
| ctgccacctg | gggcggtgcg | ggcccggagc | ccggagcccg | ggtagcgcgt | agagccggcg | 120 |
| cgatgcacgt | gcgctcactg | cgagctgcgg | cgccgcacag | cttcgtggcg | ctctgggcac | 180 |
| ccctgttcct | gctgcgctcc | gccctggccg | acttcagcct | ggacaacgag | gtgcactcga | 240 |
| gcttcatcca | ccgcgcctc | cgcagccagg | agcggcggga | gatgcagcgc | gagatcctct | 300 |
| ccattttggg | cttgccccac | cgcccgcgcc | cgcacctcca | gggcaagcac | aactcggcac | 360 |
| ccatgttcat | gctggacctg | tacaacgcca | tggcggtgga | ggagggcggc | gggcccggcg | 420 |
| gccagggctt | ctcctacccc | tacaaggccg | tcttcagtac | ccagggcccc | cctctggcca | 480 |
| gcctgcaaga | tagccatttc | ctcaccgacg | ccgacatggt | catgagcttc | gtcaacctcg | 540 |
| tggaacatga | caaggaattc | ttccacccac | gctaccacca | tcgagagttc | cggtttgatc | 600 |
| tttccaagat | cccagaaggg | gaagctgtca | cggcagccga | attccggatc | tacaaggact | 660 |
| acatccggga | acgcttcgac | aatgagacgt | tccggatcag | cgtttatcag | gtgctccagg | 720 |
| agcacttggg | cagggaatcg | gatctcttcc | tgctcgacag | ccgtacctc | tgggcctcgg | 780 |
| aggagggctg | gctggtgttt | gacatcacag | ccaccagcaa | ccactgggtg | gtcaatccgc | 840 |
| ggcacaacct | gggcctgcag | ctctcggtgg | agacgctgga | tgggcagagc | atcaacccca | 900 |
| agttggcggg | cctgattggg | cggcacgggc | cccagaacaa | gcagcccttc | atggtggctt | 960 |
| tcttcaaggc | cacggaggtc | cacttccgca | gcatccggtc | cacggggagc | aaacagcgca | 1020 |
| gccagaaccg | ctccaagacg | cccaagaacc | aggaagccct | gcggatggcc | aacgtggcag | 1080 |
| agaacagcag | cagcgaccag | aggcaggcct | gtaagaagca | cgagctgtat | gtcagcttcc | 1140 |
| gagacctggg | ctggcaggac | tggatcatcg | cgcctgaagg | ctacgccgcc | tactactgtg | 1200 |
| agggggagtg | tgccttccct | ctgaactcct | acatgaacgc | caccaaccac | gccatcgtgc | 1260 |
| agacgctggt | ccacttcatc | aacccggaaa | cggtgcccaa | gccctgctgt | gcgcccacgc | 1320 |
| agctcaatgc | catctccgtc | ctctacttcg | atgacagctc | caacgtcatc | ctgaagaaat | 1380 |
| acagaaacat | ggtggtccgg | gcctgtggct | gccactagct | cctccgagaa | ttcagaccct | 1440 |
| ttggggccaa | gttttctgg | atcctccatt | gctcgccttg | gccaggaacc | agcagaccaa | 1500 |
| ctgccttttg | tgagaccttc | ccctccctat | ccccaacttt | aaaggtgtga | gagtattagg | 1560 |
| aaacatgagc | agcatatggc | ttttgatcag | tttttcagtg | gcagcatcca | atgaacaaga | 1620 |
| tcctacaagc | tgtgcaggca | aaacctagca | ggaaaaaaaa | acaacgcata | agaaaaatg | 1680 |
| gccgggccag | gtcattggct | gggaagtctc | agccatgcac | ggactcgttt | ccagaggtaa | 1740 |
| ttatgagcgc | ctaccagcca | ggccaccag | ccgtgggagg | aagggggcgt | ggcaagggt | 1800 |
| gggcacattg | gtgtctgtgc | gaaaggaaaa | ttgacccgga | agttcctgta | ataaatgtca | 1860 |
| caataaaacg | aatgaatg | | | | | 1878 |

<210> SEQ ID NO 8
<211> LENGTH: 431
<212> TYPE: PRT
<213> ORGANISM: homo sapiens

```
<400> SEQUENCE: 8

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
        275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415
```

Leu Lys Lys Tyr Arg Asn Met Val Val Arg Ala Cys Gly Cys His
            420                 425                 430

<210> SEQ ID NO 9
<211> LENGTH: 22
<212> TYPE: DNA
<213> ORGANISM: homo sapiens

<400> SEQUENCE: 9
actgcggtct cctaaaggtc ga                                          22

<210> SEQ ID NO 10
<211> LENGTH: 21
<212> TYPE: DNA
<213> ORGANISM: homo sapiens

<400> SEQUENCE: 10
gctgacctga gtgcctgcga t                                           21

<210> SEQ ID NO 11
<211> LENGTH: 26
<212> TYPE: DNA
<213> ORGANISM: homo sapiens

<400> SEQUENCE: 11
gaatgctgat ggtcgttttt attatg                                      26

<210> SEQ ID NO 12
<211> LENGTH: 20
<212> TYPE: DNA
<213> ORGANISM: homo sapiens

<400> SEQUENCE: 12
agactgaagc cggtaaagat                                             20

<210> SEQ ID NO 13
<211> LENGTH: 26
<212> TYPE: DNA
<213> ORGANISM: homo sapiens

<400> SEQUENCE: 13
aagaggacaa gaaggactaa aaatat                                      26

<210> SEQ ID NO 14
<211> LENGTH: 25
<212> TYPE: DNA
<213> ORGANISM: homo sapiens

<400> SEQUENCE: 14
gtagagatcc agcataaaga gaggt                                       25

<210> SEQ ID NO 15
<211> LENGTH: 20
<212> TYPE: DNA
<213> ORGANISM: homo sapiens

<400> SEQUENCE: 15
agcccgggta gcgcgtagag                                             20

<210> SEQ ID NO 16
<211> LENGTH: 21
<212> TYPE: DNA
<213> ORGANISM: homo sapiens

<400> SEQUENCE: 16

```
gcgccggtgg atgaagctcg a                                    21

<210> SEQ ID NO 17
<211> LENGTH: 24
<212> TYPE: DNA
<213> ORGANISM: homo sapiens

<400> SEQUENCE: 17
taaaggtgac agtacacagg aaca                                 24

<210> SEQ ID NO 18
<211> LENGTH: 23
<212> TYPE: DNA
<213> ORGANISM: homo sapiens

<400> SEQUENCE: 18
tctatgatgg caaagcaatg tcc                                  23

<210> SEQ ID NO 19
<211> LENGTH: 26
<212> TYPE: DNA
<213> ORGANISM: homo sapiens

<400> SEQUENCE: 19
tacaagcctg ccataagtga agaagc                               26

<210> SEQ ID NO 20
<211> LENGTH: 25
<212> TYPE: DNA
<213> ORGANISM: homo sapiens

<400> SEQUENCE: 20
atcatcgtga aacaatatcc gtctg                                25

<210> SEQ ID NO 21
<211> LENGTH: 26
<212> TYPE: DNA
<213> ORGANISM: homo sapiens

<400> SEQUENCE: 21
tcctctcatc agccatttgt cctttc                               26

<210> SEQ ID NO 22
<211> LENGTH: 22
<212> TYPE: DNA
<213> ORGANISM: homo sapiens

<400> SEQUENCE: 22
agttactaca cattcttcat ag                                   22

<210> SEQ ID NO 23
<211> LENGTH: 20
<212> TYPE: DNA
<213> ORGANISM: homo sapiens

<400> SEQUENCE: 23
ctctgctcac tctgcacctg                                      20

<210> SEQ ID NO 24
<211> LENGTH: 20
<212> TYPE: DNA
<213> ORGANISM: homo sapiens

<400> SEQUENCE: 24
```

```
ccggtcacca tcaaaatagc                                               20

<210> SEQ ID NO 25
<211> LENGTH: 20
<212> TYPE: DNA
<213> ORGANISM: homo sapiens

<400> SEQUENCE: 25
atcaaccgct tctgttacgg                                               20

<210> SEQ ID NO 26
<211> LENGTH: 20
<212> TYPE: DNA
<213> ORGANISM: homo sapiens

<400> SEQUENCE: 26
atgcaacgac actgcttcac                                               20

<210> SEQ ID NO 27
<211> LENGTH: 20
<212> TYPE: DNA
<213> ORGANISM: homo sapiens

<400> SEQUENCE: 27
tgccacctga gaaaggctac                                               20

<210> SEQ ID NO 28
<211> LENGTH: 20
<212> TYPE: DNA
<213> ORGANISM: homo sapiens

<400> SEQUENCE: 28
acagacaggc tcatccgact                                               20

<210> SEQ ID NO 29
<211> LENGTH: 20
<212> TYPE: DNA
<213> ORGANISM: homo sapiens

<400> SEQUENCE: 29
cactacgacc caggcttcat                                               20

<210> SEQ ID NO 30
<211> LENGTH: 20
<212> TYPE: DNA
<213> ORGANISM: homo sapiens

<400> SEQUENCE: 30
ctccgcagct tcttgcttag                                               20

<210> SEQ ID NO 31
<211> LENGTH: 20
<212> TYPE: DNA
<213> ORGANISM: homo sapiens

<400> SEQUENCE: 31
atccttcttc atctggctgc                                               20

<210> SEQ ID NO 32
<211> LENGTH: 20
<212> TYPE: DNA
<213> ORGANISM: homo sapiens

<400> SEQUENCE: 32
```

```
aattggtgtc ctgaggatcg                                                    20

<210> SEQ ID NO 33
<211> LENGTH: 20
<212> TYPE: DNA
<213> ORGANISM: homo sapiens

<400> SEQUENCE: 33
atagtgagcc cttcccacct                                                    20

<210> SEQ ID NO 34
<211> LENGTH: 20
<212> TYPE: DNA
<213> ORGANISM: homo sapiens

<400> SEQUENCE: 34
aatgaacaga cccgcatttc                                                    20

<210> SEQ ID NO 35
<211> LENGTH: 21
<212> TYPE: DNA
<213> ORGANISM: homo sapiens

<400> SEQUENCE: 35
gatcgccact ccagctacat c                                                  21

<210> SEQ ID NO 36
<211> LENGTH: 16
<212> TYPE: DNA
<213> ORGANISM: homo sapiens

<400> SEQUENCE: 36
gggcacggca atgacc                                                        16

<210> SEQ ID NO 37
<211> LENGTH: 2932
<212> TYPE: DNA
<213> ORGANISM: homo sapiens

<400> SEQUENCE: 37
gctccgcgcc gagggctgga ggatgcgttc cctggggtcc ggacttatga aaatatgcat        60
cagtttaata ctgtcttgga attcatgaga tggaagcata ggtcaaagct gtttggagaa       120
aatcagaagt acagttttat ctagccacat cttggaggag tcgtaagaaa gcagtgggag       180
ttgaagtcat tgtcaagtgc ttgcgatctt ttacaagaaa atctcactga atgatagtca       240
tttaaattgg tgaagtagca agaccaatta ttaaaggtga cagtacacag gaaacattac       300
aattgaacaa tgactcagct atacatttac atcagattat tgggagccta tttgttcatc       360
atttctcgtg ttcaaggaca gaatctggat agtatgcttc atggcactgg gatgaaatca       420
gactccgacc agaaaaagtc agaaaatgga gtaaccttag caccagagga taccttgcct       480
tttttaaagt gctattgctc agggcactgt ccagatgatg ctattaataa cacatgcata       540
actaatggac attgctttgc catcatagaa gaagatgacc agggagaaac cacattagct       600
tcagggtgta tgaaatatga aggatctgat tttcagtgca agattctcc aaaagcccag       660
ctacgccgga caatagaatg ttgtcggacc aatttatgta accagtattt gcaacccaca       720
ctgcccctg ttgtcatagg tccgtttttt gatggcagca ttcgatggct ggttttgctc       780
atttctatgg ctgtctgcat aattgctatg atcatcttct ccagctgctt ttgttacaaa       840
cattattgca agagcatctc aagcagacgt cgttacaatc gtgatttgga acaggatgaa       900
```

```
gcatttattc cagttggaga atcactaaaa gaccttattg accagtcaca aagttctggt      960
agtgggtctg gactaccttt attggttcag cgaactattg ccaaacagat tcagatggtc     1020
cggcaagttg gtaaaggccg atatggaaga gtatggatgg gcaaatggcg tggcgaaaaa     1080
gtggcggtga agtattctt taccactgaa gaagccagct ggtttcgaga aacagaaatc     1140
taccaaactg tgctaatgcg ccatgaaaac atacttggtt tcatagcggc agacattaaa     1200
ggtacaggtt cctggactca gctctatttg attactgatt accatgaaaa tggatctctc     1260
tatgacttcc tgaaatgtgc tacactggac accagagccc tgcttaaatt ggcttattca     1320
gctgcctgtg gtctgtgcca cctgcacaca gaaatttatg caccccaagg aaagcccgca     1380
attgctcatc gagacctaaa gagcaaaaac atcctcatca agaaaatgg gagttgctgc     1440
attgctgacc tgggccttgc tgttaaattc aacagtgaca caaatgaagt tgatgtgccc     1500
ttgaatacca gggtgggcac caaacgctac atggctcccg aagtgctgga cgaaagcctg     1560
aacaaaaacc acttccagcc ctacatcatg gctgacatct acagcttcgg cctaatcatt     1620
tgggagatgg ctcgtcgttg tatcacagga gggatcgtgg aagaatacca attgccatat     1680
tacaacatgg taccgagtga tccgtcatac gaagatatgc gtgaggttgt gtgtgtcaaa     1740
cgtttgcggc caattgtgtc taatcggtgg aacagtgatg aatgtctacg agcagttttg     1800
aagctaatgt cagaatgctg ggcccacaat ccagcctcca gactcacagc attgagaatt     1860
aagaagacgc ttgccaagat ggttgaatcc caagatgtaa aaatctgatg gttaaaccat     1920
cggaggagaa actctagact gcaagaactg ttttttaccca tggcatgggt ggaattagag     1980
tggaataagg atgttaactt ggttctcaga ctctttcttc actacgtgtt cacaggctgc     2040
taatattaaa cctttcagta ctcttattag gatacaagct gggaacttct aaacacttca     2100
ttctttatat atggacagct ttattttaaa tgtggttttt gatgcctttt tttaagtggg     2160
tttttatgaa ctgcatcaag acttcaatcc tgattagtgt ctccagtcaa gctctgggta     2220
ctgaattgcc tgttcataaa acggtgcttt ctgtgaaagc cttaagaaga taaatgagcg     2280
cagcagagat ggagaaatag actttgcctt ttacctgaga cattcagttc gtttgtattc     2340
tacctttgta aaacagccta tagatgatga tgtgtttggg atactgctta ttttatgata     2400
gtttgtcctg tgtccttagt gatgtgtgtg tgtctccatg cacatgcacg ccgggattcc     2460
tctgctgcca tttgaattag aagaaaataa tttatatgca tgcacaggaa gatattggtg     2520
gccggtggtt ttgtgcttta aaaatgcaat atctgaccaa gattcgccaa tctcatacaa     2580
gccatttact ttgcaagtga gatagcttcc ccaccagctt tattttttaa catgaaagct     2640
gatgccaagg ccaaaagaag tttaaagcat ctgtaaattt ggactgtttt ccttcaacca     2700
ccattttttt tgtggttatt attttttgtca cggaaagcat cctctccaaa gttggagctt     2760
ctattgccat gaaccatgct tacaaagaaa gcacttctta ttgaagtgaa ttcctgcatt     2820
tgatagcaat gtaagtgcct ataaccatgt tctatattct ttattctcag taactttaa     2880
aagggaagtt atttatattt tgtgtataat gtgctttatt tgcaaatcac cc             2932
```

<210> SEQ ID NO 38
<211> LENGTH: 532
<212> TYPE: PRT
<213> ORGANISM: homo sapiens

<400> SEQUENCE: 38

Met Thr Gln Leu Tyr Ile Tyr Ile Arg Leu Leu Gly Ala Tyr Leu Phe
1               5                   10                  15

```
Ile Ile Ser Arg Val Gln Gly Gln Asn Leu Asp Ser Met Leu His Gly
         20                  25                  30

Thr Gly Met Lys Ser Asp Ser Asp Gln Lys Lys Ser Glu Asn Gly Val
             35                  40                  45

Thr Leu Ala Pro Glu Asp Thr Leu Pro Phe Leu Lys Cys Tyr Cys Ser
 50                  55                  60

Gly His Cys Pro Asp Asp Ala Ile Asn Asn Thr Cys Ile Thr Asn Gly
 65                  70                  75                  80

His Cys Phe Ala Ile Ile Glu Glu Asp Asp Gln Gly Glu Thr Thr Leu
                 85                  90                  95

Ala Ser Gly Cys Met Lys Tyr Glu Gly Ser Asp Phe Gln Cys Lys Asp
             100                 105                 110

Ser Pro Lys Ala Gln Leu Arg Arg Thr Ile Glu Cys Cys Arg Thr Asn
         115                 120                 125

Leu Cys Asn Gln Tyr Leu Gln Pro Thr Leu Pro Pro Val Val Ile Gly
     130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                 165                 170                 175

Lys His Tyr Cys Lys Ser Ile Ser Ser Arg Arg Arg Tyr Asn Arg Asp
             180                 185                 190

Leu Glu Gln Asp Glu Ala Phe Ile Pro Val Gly Glu Ser Leu Lys Asp
         195                 200                 205

Leu Ile Asp Gln Ser Gln Ser Ser Gly Ser Gly Ser Gly Leu Pro Leu
     210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                 245                 250                 255

Lys Val Ala Val Lys Val Phe Phe Thr Thr Glu Glu Ala Ser Trp Phe
             260                 265                 270

Arg Glu Thr Glu Ile Tyr Gln Thr Val Leu Met Arg His Glu Asn Ile
         275                 280                 285

Leu Gly Phe Ile Ala Ala Asp Ile Lys Gly Thr Gly Ser Trp Thr Gln
     290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                 325                 330                 335

Ser Ala Ala Cys Gly Leu Cys His Leu His Thr Glu Ile Tyr Gly Thr
             340                 345                 350

Gln Gly Lys Pro Ala Ile Ala His Arg Asp Leu Lys Ser Lys Asn Ile
         355                 360                 365

Leu Ile Lys Lys Asn Gly Ser Cys Cys Ile Ala Asp Leu Gly Leu Ala
     370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
                 405                 410                 415

Leu Asn Lys Asn His Phe Gln Pro Tyr Ile Met Ala Asp Ile Tyr Ser
             420                 425                 430

Phe Gly Leu Ile Ile Trp Glu Met Ala Arg Arg Cys Ile Thr Gly Gly
         435                 440                 445
```

```
Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
    530

<210> SEQ ID NO 39
<211> LENGTH: 2032
<212> TYPE: DNA
<213> ORGANISM: homo sapiens

<400> SEQUENCE: 39
cgcggggcgc ggagtcggcg gggcctcgcg ggacgcgggc agtgcggaga ccgcggcgct      60
gaggacgcgg gagccgggag cgcacgcgcg gggtggagtt cagcctactc tttcttagat     120
gtgaaaggaa aggaagatca tttcatgcct tgttgataaa ggttcagact tctgctgatt     180
cataaccatt tggctctgag ctatgacaag agaggaaaca aaaagttaaa cttacaagcc     240
tgccataagt gagaagcaaa cttccttgat aacatgcttt tgcgaagtgc aggaaaatta     300
aatgtgggca ccaagaaaga ggatggtgag agtacagccc ccaccccccg tccaaaggtc     360
ttgcgttgta atgccacca ccattgtcca gaagactcag tcaacaatat ttgcagcaca     420
gacggatatt gtttcacgat gatagaagag gatgactctg ggttgcctgt ggtcacttct     480
ggttgcctag gactagaagg ctcagatttt cagtgtcggg acactcccat tcctcatcaa     540
agaagatcaa ttgaatgctg cacagaaagg aacgaatgta ataaagacct acaccctaca     600
ctgcctccat tgaaaaacag agattttgtt gatggaccta caccacag ggctttactt      660 atatctgtga ctgtctgtag tttgctcttg gtccttatca tattattttg ttacttccgg     720
tataaaagac aagaaaccag acctcgatac agcattgggt tagaacagga tgaaacttac     780
attcctcctg gagaatccct gagagactta attgagcagt ctcagagctc aggaagtgga     840
tcaggcctcc ctctgctggt ccaaaggact atagctaagc agattcagat ggtgaaacag     900
attggaaaag gtcgctatgg ggaagtttgg atgggaaagt ggcgtggcga aaggtagct      960 gtgaaagtgt tcttcaccac agaggaagcc agctggttca gagagacaga aatatatcag    1020
acagtgttga tgaggcatga aaacattttg ggtttcattg ctgcagatat caaagggaca    1080
gggtcctgga cccagttgta cctaatcaca gactatcatg aaaatggttc cctttatgat    1140
tatctgaagt ccaccaccct agacgctaaa tcaatgctga agttagccta ctcttctgtc    1200
agtggcttat gtcatttaca cacagaaatc tttagtactc aaggcaaacc agcaattgcc    1260
catcgagatc tgaaaagtaa aaacattctg gtgaagaaaa atggaacttg ctgtattgct    1320
gacctgggcc tggctgttaa atttattagt gatacaaatg aagttgacat accacctaac    1380
actcgagttg gcaccaaacg ctatatgcct ccagaagtgt tggacgagag cttgaacaga    1440
aatcacttcc agtcttacat catggctgac atgtatagtt ttggcctcat cctttgggag    1500
gttgctagga gatgtgtatc aggaggtata gtggaagaat accagcttcc ttatcatgac    1560
ctagtgccca gtgaccctc ttatgaggac atgagggaga ttgtgtgcat caagaagtta    1620
```

```
cgcccctcat tcccaaaccg gtggagcagt gatgagtgtc taaggcagat gggaaaactc   1680
atgacagaat gctgggctca caatcctgca tcaaggctga cagccctgcg ggttaagaaa   1740
acacttgcca aaatgtcaga gtcccaggac attaaactct gataggagag gaaaagtaag   1800
catctctgca gaaagccaac aggtactctt ctgtttgtgg gcagagcaaa agacatcaaa   1860
taagcatcca cagtacaagc cttgaacatc gtcctgcttc ccagtgggtt cagacctcac   1920 cttcaggga gcgacctggg caaagacaga gaagctccca gaaggagaga ttgatccgtg     1980
tctgtttgta ggcggagaaa ccgttgggta acttgttcaa gatatgatgc at            2032
```

<210> SEQ ID NO 40
<211> LENGTH: 502
<212> TYPE: PRT
<213> ORGANISM: homo sapiens

<400> SEQUENCE: 40

```
Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300
```

| | | | | | | | | | | | | |
|---|---|---|---|---|---|---|---|---|---|---|---|---|
|Ala|Tyr|Ser|Ser|Val|Ser|Gly|Leu|Cys|His|Leu|His|Thr|Glu|Ile|Phe|
|305| | | |310| | | |315| | | |320| | | |
|Ser|Thr|Gln|Gly|Lys|Pro|Ala|Ile|Ala|His|Arg|Asp|Leu|Lys|Ser|Lys|
| | | | |325| | | | |330| | | | |335| |
|Asn|Ile|Leu|Val|Lys|Lys|Asn|Gly|Thr|Cys|Cys|Ile|Ala|Asp|Leu|Gly|
| | | |340| | | | |345| | | | |350| | |
|Leu|Ala|Val|Lys|Phe|Ile|Ser|Asp|Thr|Asn|Glu|Val|Asp|Ile|Pro|Pro|
| | |355| | | | |360| | | | |365| | | |
|Asn|Thr|Arg|Val|Gly|Thr|Lys|Arg|Tyr|Met|Pro|Pro|Glu|Val|Leu|Asp|
| |370| | | | |375| | | | |380| | | | |
|Glu|Ser|Leu|Asn|Arg|Asn|His|Phe|Gln|Ser|Tyr|Ile|Met|Ala|Asp|Met|
|385| | | | |390| | | | |395| | | | |400|
|Tyr|Ser|Phe|Gly|Leu|Ile|Leu|Trp|Glu|Val|Ala|Arg|Arg|Cys|Val|Ser|
| | | | |405| | | | |410| | | | |415| |
|Gly|Gly|Ile|Val|Glu|Glu|Tyr|Gln|Leu|Pro|Tyr|His|Asp|Leu|Val|Pro|
| | | |420| | | | |425| | | | |430| | |
|Ser|Asp|Pro|Ser|Tyr|Glu|Asp|Met|Arg|Glu|Ile|Val|Cys|Ile|Lys|Lys|
| | |435| | | | |440| | | | |445| | | |
|Leu|Arg|Pro|Ser|Phe|Pro|Asn|Arg|Trp|Ser|Ser|Asp|Glu|Cys|Leu|Arg|
| |450| | | | |455| | | | |460| | | | |
|Gln|Met|Gly|Lys|Leu|Met|Thr|Glu|Cys|Trp|Ala|His|Asn|Pro|Ala|Ser|
|465| | | | |470| | | | |475| | | | |480|
|Arg|Leu|Thr|Ala|Leu|Arg|Val|Lys|Lys|Thr|Leu|Ala|Lys|Met|Ser|Glu|
| | | | |485| | | | |490| | | | |495| |
|Ser|Gln|Asp|Ile|Lys|Leu| | | | | | | | | | |
| | | | |500| | | | | | | | | | | |

```
<210> SEQ ID NO 41
<211> LENGTH: 3611
<212> TYPE: DNA
<213> ORGANISM: homo sapiens

<400> SEQUENCE: 41 cgcccccga   ccccggatcg   aatccccgcc   ctccgcaccc   tggatatgtt   ttctcccaga     60
cctggatatt   ttttgatat   cgtgaaacta   cgagggaaat   aatttggggg   atttcttctt    120
ggctccctgc   tttccccaca   gacatgcctt   ccgtttggag   gccgcggca    ccccgtccga    180
ggcgaaggaa   ccccccagc    cgcgagggag   agaaatgaag   ggaatttctg   cagcggcatg    240
aaagctctgc   agctaggtcc   tctcatcagc   catttgtcct   tcaaactgt    attgtgatac    300
gggcaggatc   agtccacggg   agagaagacg   agcctcccgg   ctgtttctcc   gccggtctac    360
ttcccatatt   tctttctttt   gccctcctga   ttcttggctg   gcccagggat   gacttcctcg    420
ctgcagcggc   cctggcgggt   gccctggcta   ccatggacca   tcctgctggt   cagcactgcg    480
gctgcttcgc   agaatcaaga   acggctatgt   gcgtttaaag   atccgtatca   gcaagacctt    540
gggataggtg   agagtagaat   ctctcatgaa   atgggacaa   tattatgctc   gaaaggtagc     600
acctgctatg   gcctttggga   gaaatcaaaa   ggggacataa   atcttgtaaa   caaggatgt     660
tggtctcaca   ttggagatcc   ccaagagtgt   cactatgaag   aatgtgtagt   aactaccact    720
cctcccctaa   ttcagaatgg   aacataccgt   ttctgctgtt   gtagcacaga   tttatgtaat    780
gtcaacttta   ctgagaattt   tccacctcct   gacacaacac   cactcagtcc   acctcattca    840
tttaaccgag   atgagacaat   aatcattgct   ttggcatcag   tctctgtatt   agctgttttg    900
atagttgcct   tatgctttgg   atacagaatg   ttgacaggag   accgtaaaca   aggtcttcac    960
agtatgaaca   tgatggaggc   agcagcatcc   gaaccctctc   ttgatctaga   taatctgaaa   1020
```

```
ctgttggagc tgattggccg aggtcgatat ggagcagtat ataaaggctc cttggatgag    1080
cgtccagttg ctgtaaaagt gttttccttt gcaaaccgtc agaatttat caacgaaaag    1140 aacatttaca gagtgccttt gatggaacat gacaacattg cccgctttat agttggagat    1200
gagagagtca ctgcagatgg acgcatggaa tatttgcttg tgatggagta ctatcccaat    1260
ggatctttat gcaagtattt aagtctccac acaagtgact gggtaagctc ttgccgtctt    1320
gctcattctg ttactagagg actggcttat cttcacacag aattaccacg aggagatcat    1380
tataaacctg caatttccca tcgagattta aacagcagaa atgtcctagt gaaaaatgat    1440
ggaacctgtg ttattagtga ctttggactg tccatgaggc tgactggaaa tagactggtg    1500
cgcccagggg aggaagataa tgcagccata agcgaggttg cactatcag atatatggca    1560 ccagaagtgc tagaaggagc tgtgaacttg agggactgtg aatcagcttt gaaacaagta    1620
gacatgtatg ctcttggact aatctattgg gagatattta tgagatgtac agacctcttc    1680 ccagggaat ccgtaccaga gtaccagatg cttttcaga cagaggttgg aaaccatccc    1740
acttttgagg atatgcaggt tctcgtgtct agggaaaaac agagacccaa gttcccagaa    1800
gcctggaaag aaaatagcct ggcagtgagg tcactcaagg agacaatcga agactgttgg    1860
gaccaggatg cagaggctcg gcttactgca cagtgtgctg aggaaaggat ggctgaactt    1920
atgatgattt gggaaagaaa caaatctgtg agcccaacag tcaatccaat gtctactgct    1980
atgcagaatg aacgcaacct gtcacataat aggcgtgtgc caaaaattgg tccttatcca    2040
gattattctt cctcctcata cattgaagac tctatccatc atactgacag catcgtgaag    2100
aatatttcct ctgagcattc tatgtccagc acacctttga ctataggga aaaaaccga    2160 aattcaatta actatgaacg acagcaagca caagctcgaa tccccagccc tgaaacaagt    2220
gtcaccagcc tctccaccaa cacaacaacc acaaacacca caggactcac gccaagtact    2280
ggcatgacta ctatatctga gatgccatac ccagatgaaa caaatctgca taccacaaat    2340
gttgcacagt caattgggcc aacccctgtc tgcttacagc tgacagaaga agacttggaa    2400
accaacaagc tagacccaaa agaagttgat aagaacctca aggaaagctc tgatgagaat    2460
ctcatggagc actctcttaa acagttcagt ggcccagacc cactgagcag tactagttct    2520
agcttgcttt acccactcat aaaacttgca gtagaagcaa ctggacagca ggacttcaca    2580
cagactgcaa atggccaagc atgtttgatt cctgatgttc tgcctactca gatctatcct    2640
ctccccaagc agcagaacct tcccaagaga cctactagtt tgcctttgaa caccaaaaat    2700
tcaacaaaag agcccgggct aaaatttggc agcaagcaca aatcaaactt gaaacaagtc    2760
gaaactggag ttgccaagat gaatacaatc aatgcagcag aacctcatgt ggtgacagtc    2820
accatgaatg gtgtggcagg tagaaaccac agtgttaact cccatgctgc cacaacccaa    2880
tatgccaatg gacagtact atctggccaa acaaccaaca tagtgacaca tagggcccaa    2940
gaaatgttgc agaatcagtt tattggtgag acacccggc tgaatattaa ttccagtcct    3000
gatgagcatg agcctttact gagacgagag caacaagctg gccatgatga aggtgttctg    3060
gatcgtcttg tggacaggag ggaacggcca ctagaaggtg gccgaactaa ttccaataac    3120 acaacagca atccatgttc agaacaagat gttcttgcac agggtgttcc aagcacagca    3180
gcagatcctg ggccatcaaa gcccagaaga gcacagaggc ctaattctct ggatctttca    3240
gccacaaatg tcctggatgg cagcagtata cagataggtg agtcaacaca agatggcaaa    3300
tcaggatcag gtgaaaagat caagaaacgt gtgaaaactc cctattctct taagcggtgg    3360
cgcccctcca cctgggtcat ctccactgaa tcgctggact gtgaagtcaa caataatggc    3420
```

```
agtaacaggg cagttcattc caaatccagc actgctgttt accttgcaga aggaggcact   3480
gctacaacca tggtgtctaa agatatagga atgaactgtc tgtgaaatgt tttcaagcct   3540
atggagtgaa attattttt gcatcattta acatgcaga agatgtttaa aataaaaaa    3600 aaaactgctt t                                                       3611
```

<210> SEQ ID NO 42
<211> LENGTH: 1038
<212> TYPE: PRT
<213> ORGANISM: homo sapiens

<400> SEQUENCE: 42

```
Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335
```

-continued

```
Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670

Val Asp Lys Asn Leu Lys Glu Ser Ser Asp Glu Asn Leu Met Glu His
        675                 680                 685

Ser Leu Lys Gln Phe Ser Gly Pro Asp Pro Leu Ser Ser Thr Ser Ser
    690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
        755                 760                 765
```

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
            820                 825                 830

Gly Gln Thr Thr Asn Ile Val Thr His Arg Ala Gln Glu Met Leu Gln
        835                 840                 845

Asn Gln Phe Ile Gly Glu Asp Thr Arg Leu Asn Ile Asn Ser Ser Pro
    850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Glu Arg Pro Leu Glu
                885                 890                 895

Gly Gly Arg Thr Asn Ser Asn Asn Asn Ser Asn Pro Cys Ser Glu
            900                 905                 910

Gln Asp Val Leu Ala Gln Gly Val Pro Ser Thr Ala Ala Asp Pro Gly
        915                 920                 925

Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Asn Gly Ser Asn Arg Ala
        995                 1000                1005

Val His Ser Lys Ser Ser Thr Ala Val Tyr Leu Ala Glu Gly Gly
    1010                1015                1020

Thr Ala Thr Thr Met Val Ser Lys Asp Ile Gly Met Asn Cys Leu
1025                1030                1035

<210> SEQ ID NO 43
<211> LENGTH: 3561
<212> TYPE: DNA
<213> ORGANISM: homo sapiens

<400> SEQUENCE: 43

```
cccgggtcag cgcccgcccg cccgcgctcc tcccggccgc tcctcccgcc ccgcccggcc    60
cggcgccgac tctgcggccg cccgacgagc ccctcgcggc actgccccgg cccggcccc   120
ggccccggcc ccctcccgcc gcaccgcccc cggcccggcc ctcgccctc cgcactcccg   180
cctccctccc tccgcccgct cccgcgccct cctccctccc tcctcccag ctgtcccgtt   240
cgcgtcatgc cgagcctccc ggcccgcgcg gcccgctgc tgctcctcgg gctgctgctg   300
ctcggctccc ggccggcccg cggcgccggc cccgagcccc ccgtgctgcc catccgttct   360
gagaaggagc cgctgcccgt tcggggagcg gcaggctgca ccttcggcgg gaaggtctat   420
gccttggacg agacgtggca cccggaccta ggggagccat tcgggggtgat gcgctgcgtg   480
ctgtgcgcct gcgaggcgac agggaccttg aggcccagag agatgaagta gcttgtctag   540
ggtcacgcag cttcctcagt ggggtcgccg taccaggggc cctggcaggg tcagctgcaa   600
```

```
gaacatcaaa ccagagtgcc caaccccggc ctgtgggcag ccgcgccagc tgccgggaca    660
ctgctgccag acctgccccc aggagcgcag cagttcggag cggcagccga gcggcctgtc    720
cttcgagtat ccgcgggacc cggagcatcg cagttatagc gaccgcgggg agccaggcgc    780
tgaggagcgg gcccgtggtg acggccacac ggacttcgtg gcgctgctga cagggccgag    840
gtcgcaggcg gtggcacgag cccgagtctc gctgctgcgc tctagcctcc gcttctctat    900
ctcctacagg cggctggacc gccctaccag gatccgcttc tcagactcca atggcagtgt    960
cctgtttgag caccctgcag cccccaccca agatggcctg gtctgtgggg tgtggcgggc   1020
agtgcctcgg ttgtctctgc ggctccttag ggcagaacag ctgcatgtgg cacttgtgac   1080
actcactcac ccttcagggg aggtctgggg gcctctcatc cggcaccggg ccctggctgc   1140
agagaccttc agtgccatcc tgactctaga aggcccccca cagcagggcg tagggggcat   1200
caccctgctc actctcagtg acacagagga ctccttgcat ttttttgctgc tcttccgagg   1260
gctgctggaa cccaggagtg gggattctac accaggggca gctactgcga gaacttcagg   1320
ccaatgtctc agcccaggaa ccaggctttg ctgaggtgct gcccaacctg acagtccagg   1380
agatggactg gctggtgctg ggggagctgc agatggccct ggagtgggca ggcaggccag   1440
ggctgcgcat cagtggacac attgctgcca ggaagagctg cgacgtcctg caaagtgtcc   1500
tttgtggggc tgatgccctg atcccagtcc agacgggtgc tgccggctca gccagcctca   1560
cgctgctagg aaatggctcc ctgatctatc aggtgcaagt ggtagggaca agcagtgagg   1620
tggtggccat gacactggag accaagcctc agcggaggga tcagcgcact gtcctgtgcc   1680
acatggctgg actccagcca ggaggacaca cggccgtggg tatctgccct gggctgggtg   1740
cccgaggggc tcatatgctg ctgcagaatg agctcttcct gaacgtgggc accaaggact   1800
tcccagacgg agagcttcgg gggcacgtgg ctgccctgcc ctactgtggg catagctccc   1860
gccatgacac gctgcccgtg cccctagcag gagccctggt gctaccccct gtgaagagcc   1920
aagcagcagg gcacgcctgg cttccttgg atacccactg tcacctgcac tatgaagtgc   1980
tgctggctgg gcttggtggc tcagaacaag gcactgtcac tgcccacctc cttgggcctc   2040
ctggaacgcc agggcctcgg cggctgctga agggattcta tggctcagag gcccagggtg   2100
tggtgaagga cctggagccg gaactgctgc ggcacctggc aaaaggcatg gcctccctga   2160
tgatcaccac caagggtagc cccagagggg agctccgagg gcaggtgcac atagccaacc   2220
aatgtgaggt tggcggactg cgcctggagg cggccggggc cgaggggtg cgggcgctgg   2280
gggctccgga tacagcctct gctgcgccgc ctgtggtgcc tggtctcccg gccctagcgc   2340
ccgccaaacc tggtggtcct gggcggcccc gagaccccaa cacatgcttc ttcgaggggc   2400
agcagcgccc ccacggggct cgctgggcgc ccaactacga cccgctctgc tcactctgca   2460
cctgccagag acgaacggtg atctgtgacc cggtggtgtg cccaccgccc agctgcccac   2520
acccggtgca ggctcccgac cagtgctgcc ctgtttgccc tgagaaacaa gatgtcagag   2580
acttgccagg gctgccaagg agccgggacc caggagaggg ctgctatttt gatggtgacc   2640
ggagctggcg ggcagcgggt acgcggtggc acccgttgt gccccccttt ggcttaatta   2700
agtgtgctgt ctgcacctgc aagggggggca ctggagaggg gcactgtgag aaggtgcagt   2760
gtccccggct ggcctgtgcc cagctgtgc gtgtcaaccc caccgactgc tgcaaacagt   2820
gtccagtggg gtcggggggcc cacccccagc tgggggaccc catgcaggct gatgggcccc   2880
ggggctgccg ttttgctggg cagtggttcc cagagagtca gagctggcac ccctcagtgc   2940
cccctttttgg agagatgagc tgtatcacct gcagatgtgg ggcaggggtg cctcactgtg   3000
```

| | |
|---|---|
| agcgggatga ctgttcactg ccactgtcct gtggctcggg gaaggagagt cgatgctgtt | 3060 |
| cccgctgcac ggcccaccgg cggccagccc cagagaccag aactgatcca gagctggaga | 3120 |
| aagaagccga aggctcttag ggagcagcca gagggccaag tgaccaagag gatggggcct | 3180 |
| gagctgggga aggggtggca tcgaggacct tcttgcattc tcctgtggga agcccagtgc | 3240 |
| ctttgctccc ctgtcctgcc tctactccca ccccactac ctctgggaac acagctcca | 3300 |
| caaggggag aggcagctgg gccagaccga ggtcacagcc actccaagtc ctgccctgcc | 3360 |
| accctcggcc tctgtcctgg aagccccacc cctttcctcc tgtacataat gtcactggct | 3420 |
| tgttgggatt tttaatttat cttcactcag caccaagggc ccccgacact ccactcctgc | 3480 |
| tgcccctgag ctgagcagag tcattattgg agagttttgt atttattaaa acatttcttt | 3540 |
| ttcagtcaaa aaaaaaaaaa a | 3561 |

<210> SEQ ID NO 44
<211> LENGTH: 94
<212> TYPE: PRT
<213> ORGANISM: homo sapiens

<400> SEQUENCE: 44

Met Pro Ser Leu Pro Ala Pro Pro Ala Pro Leu Leu Leu Gly Leu
1               5                   10                  15

Leu Leu Leu Gly Ser Arg Pro Ala Arg Gly Ala Gly Pro Glu Pro Pro
            20                  25                  30

Val Leu Pro Ile Arg Ser Glu Lys Glu Pro Leu Pro Val Arg Gly Ala
        35                  40                  45

Ala Gly Cys Thr Phe Gly Gly Lys Val Tyr Ala Leu Asp Glu Thr Trp
    50                  55                  60

His Pro Asp Leu Gly Glu Pro Phe Gly Val Met Arg Cys Val Leu Cys
65                  70                  75                  80

Ala Cys Glu Ala Thr Gly Thr Leu Arg Pro Arg Glu Met Lys
                85                  90

<210> SEQ ID NO 45
<211> LENGTH: 4049
<212> TYPE: DNA
<213> ORGANISM: homo sapiens

<400> SEQUENCE: 45

| | |
|---|---|
| gcggccgcac tcagcgccac gcgtcgaaag cgcaggcccc gaggacccgc cgcactgaca | 60 |
| gtatgagccg cacagcctac acggtggag ccctgcttct cctcttgggg accctgctgc | 120 |
| cggctgctga aggaaaaag aaagggtccc aaggtgccat ccccccgcca gacaaggccc | 180 |
| agcacaatga ctcagagcag actcagtcgc ccagcagcc tggctccagg aaccgggggc | 240 |
| ggggccaagg gcgggcact gccatgcccg ggaggaggt gctggagtcc agccaagagg | 300 |
| ccctgcatgt gacggagcgc aaatacctga agcgagactg tgcaaaaccc agccgctta | 360 |
| agcagaccat ccacgaggaa ggctgcaaca gtcgcaccat catcaaccgc ttctgttacg | 420 |
| gccagtgcaa ctctttctac atccccagc acatccggaa ggaggaagt tcctttcagt | 480 |
| cctgctcctt ctgcaagccc aagaaattca ctaccatgat ggtcacactc aactgccctg | 540 |
| aactacagcc acctaccaag aagaagagag tcacacgtgt gaagcagtgt cgttgcatat | 600 |
| ccatcgattt ggattaagcc aaatccaggt gcacccagca tgtcctagga atgcagcccc | 660 |
| aggaagtccc agacctaaaa caaccagatt cttacttggc ttaaacctag aggccagaag | 720 |
| aaccccagc tgcctcctgg caggagcctg cttgtgcgta gttcgtgtgc atgagtgtgg | 780 |

```
atgggtgcct gtgggtgttt ttagacacca gagaaaacac agtctctgct agagagcact    840
ccctattttg taaacatatc tgctttaatg gggatgtacc agaaacccac ctcaccccgg    900
ctcacatcta aaggggcggg gccgtggtct ggttctgact tgtgtttttt gtgccctcct    960
ggggaccaga atctcctttc ggaatgaatg ttcatggaag aggctcctct gagggcaaga   1020
gacctgtttt agtgctgcat tcgacatgga aaagtccttt taacctgtgc ttgcatcctc   1080
ctttcctcct cctcctcaca atccatctct tcttaagttg atagtgacta tgtcagtcta   1140
atctcttgtt tgccaaggtt cctaaattaa ttcacttaac catgatgcaa atgttttttca   1200
tttttgtgaag accctccaga ctctgggaga ggctggtgtg ggcaaggaca agcaggatag   1260
tggagtgaga aagggagggt ggagggtgag gccaaatcag gtccagcaaa agtcagtagg   1320
gacattgcag aagcttgaaa ggccaatacc agaacacagg ctgatgcttc tgagaaagtc   1380
ttttcctagt atttaacaga acccaagtga acagaggaga aatgagattg ccagaaagtg   1440
attaactttg gccgttgcaa tctgctcaaa cctaacacca aactgaaaac ataaatactg   1500
accactccta tgttcggacc caagcaagtt agctaaacca aaccaactcc tctgctttgt   1560
ccctcaggtg gaaagagag gtagtttaga actctctgca tagggtggg aattaatcaa   1620
aaacckcaga ggctgaaatt cctaatacct ttcctttatc gtggttatag tcagctcatt   1680
tccattccac tatttcccat aatgcttctg agagccacta acttgattga taaagatcct   1740
gcctctgctg agtgtacctg acagtaagtc taaagatgar agagtttagg gactactctg   1800
ttttagcaag aratattktg ggggtctttt tgttttaact attgtcagga gattgggcta   1860
ragagaagac gacgagagta aggaaataaa gggrattgcc tctggctaga gagtaagtta   1920
ggtgttaata cctggtagaa atgtaaggga tatgacctcc ctttctttat gtgctcactg   1980
aggatctgag gggaccctgt taggagagca tagcatcatg atgtattagc tgttcatctg   2040
ctactggttg gatggacata actattgtaa ctattcagta tttactggta ggcactgtcc   2100
tctgattaaa cttggcctac tggcaatggc tacttaggat tgatctaagg gccaaagtgc   2160
agggtgggtg aactttattg tactttggat ttggttaacc tgttttcttc aagcctgagg   2220
ttttatatac aaactccctg aatactcttt ttgccttgta tcttctcagc ctccatcagcca   2280
agtcctatgt aatatggaaa acaaacactg cagacttgag attcagttgc cgatcaaggc   2340
tctggcattc agagaaccct tgcaactcga gaagctgttt ttatttcgtt tttgttttga   2400
tccagtgctc tcccatctaa caactaaaca ggagccattt caaggcggga gatattttaa   2460
acacccaaaa tgttgggtct gattttcaaa cttttaaact cactactgat gattctcacg   2520
ctaggcgaat ttgtccaaac acatagtgtg tgtgttttgt atacactgta tgaccccacc   2580
ccaaatcttt gtattgtcca cattctccaa caataaagca cagagtggat ttaattaagc   2640
acacaaatgc taaggcagaa ttttgagggt gggagagaag aaaagggaaa gaagctgaaa   2700
atgtaaaacc acaccaggga ggaaaaatga cattcagaac cagcaaacac tgaatttctc   2760
ttgttgtttt aactctgcca caagaatgca atttcgttaa tggagatgac ttaagttggc   2820
agcagtaatc ttcttttagg agcttgtacc acagtcttgc ataagtgc agatttggct   2880
caagtaaaga gaattccctc aacactaact tcactgggat aatcagcagc gtaactaccc   2940
taaaagcata tcactagcca aagagggaaa tatctgttct tcttactgtg cctatattaa   3000
gactagtaca aatgtggtgt gtcttccaac tttcattgaa aatgccatat ctataccata   3060
ttttattcga gtcactgatg atgtaatgat atatttttc attattatag tagaatatttt  3120
ttatggcaag atatttgtgg tcttgatcat acctattaaa ataatgccaa acaccaaata   3180
```

-continued

```
tgaattttat gatgtacact ttgtgcttgg cattaaaaga aaaaaacaca catcctggaa    3240
gtctgtaagt tgttttttgt tactgtaggt cttcaaagtt aagagtgtaa gtgaaaaatc    3300
tggaggagag gataatttcc actgtgtgga atgtgaatag ttaaatgaaa agttatggtt    3360
atttaatgta attattactt caaatccttt ggtcactgtg atttcaagca tgttttcttt    3420
ttctccttta tatgactttc tctgagttgg gcaaagaaga agctgacaca ccgtatgttg    3480
ttagagtctt ttatctggtc aggggaaaca aaatcttgac ccagctgaac atgtcttcct    3540
gagtcagtgc ctgaatcttt atttttttaaa ttgaatgttc cttaaaggtt aacatttcta    3600
aagcaatatt aagaaagact ttaaatgtta ttttggaaga cttacgatgc atgtatacaa    3660
acgaatagca gataatgatg actagttcac acataaagtc ctttttaagga gaaaatctaa    3720 aatgaaaagt ggataaacag aacatttata agtgatcagt taatgcctaa gagtgaaagt    3780
agttctattg acattcctca agatatttaa tatcaactgc attatgtatt atgtctgctt    3840
aaatcattta aaaacggcaa agaattatat agactatgag gtaccttgct gtgtaggagg    3900
atgaaagggg agttgatagt ctcataaaac taatttggct tcaagtttca tgaatctgta    3960
actagaattt aattttcacc ccaataatgt tctatatagc ctttgctaaa gagcaactaa    4020
taaattaaac ctattctttc aaaaaaaaa                                      4049
```

<210> SEQ ID NO 46
<211> LENGTH: 184
<212> TYPE: PRT
<213> ORGANISM: homo sapiens

<400> SEQUENCE: 46

```
Met Ser Arg Thr Ala Tyr Thr Val Gly Ala Leu Leu Leu Leu Leu Gly
1               5                   10                  15

Thr Leu Leu Pro Ala Ala Glu Gly Lys Lys Gly Ser Gln Gly Ala
            20                  25                  30

Ile Pro Pro Pro Asp Lys Ala Gln His Asn Asp Ser Glu Gln Thr Gln
        35                  40                  45

Ser Pro Gln Gln Pro Gly Ser Arg Asn Arg Gly Arg Gly Gln Gly Arg
    50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
        115                 120                 125

Arg His Ile Arg Lys Glu Glu Gly Ser Phe Gln Ser Cys Ser Phe Cys
    130                 135                 140

Lys Pro Lys Lys Phe Thr Thr Met Met Val Thr Leu Asn Cys Pro Glu
145                 150                 155                 160

Leu Gln Pro Pro Thr Lys Lys Arg Val Thr Arg Val Lys Gln Cys
                165                 170                 175

Arg Cys Ile Ser Ile Asp Leu Asp
            180
```

<210> SEQ ID NO 47
<211> LENGTH: 1386
<212> TYPE: DNA
<213> ORGANISM: homo sapiens

<400> SEQUENCE: 47

```
gctcctcgcc ccgcgcctgc ccccaggatg gtccgcgcga ggcaccagcc gggtgggctt    60
tgcctcctgc tgctgctgct ctgccagttc atggaggacc gcagtgccca ggctgggaac   120
tgctggctcc gtcaagcgaa gaacggccgc tgccaggtcc tgtacaagac cgaactgagc   180
aaggaggagt gctgcagcac cggccggctg agcacctcgt ggaccgagga ggacgtgaat   240
gacaacacac tcttcaagtg gatgattttc aacggggggcg ccccaactg catcccctgt    300
aaagaaacgt gtgagaacgt ggactgtgga cctgggaaaa aatgccgaat gaacaagaag   360
aacaaacccc gctgcgtctg cgccccggat tgttccaaca tcacctggaa gggtccagtc   420
tgcgggctgg atgggaaaac ctaccgcaat gaatgtgcac tcctaaaggc aagatgtaaa   480
gagcagccag aactggaagt ccagtaccaa ggcagatgta aaaagacttg tcgggatgtt   540
ttctgtccag gcagctccac atgtgtggtg accagacca ataatgccta ctgtgtgacc    600
tgtaatcgga tttgcccaga gcctgcttcc tctgagcaat atctctgtgg aatgatgga    660
gtcacctact ccagtgcctg ccacctgaga aaggctacct gcctgctggg cagatctatt   720
ggattagcct atgagggaaa gtgtatcaaa gcaaagtcct gtgaagatat ccagtgcact   780
ggtgggaaaa aatgtttatg ggatttcaag gttgggagag gccgtgttc cctctgtgat    840
gagctgtgcc ctgacagtaa gtcggatgag cctgtctgtg ccagtgacaa tgccacttat   900
gccagcgagt gtgccatgaa ggaagctgcc tgctcctcag gtgtgctact ggaagtaaag   960
cactccggat cttgcaactg aatctgcccg taaaacctga gccattgatt cttcagaact  1020
ttctgcagtt tttgacttca tagattatgc tttaaaaaat tttttttaac ttattgcata  1080
acagcagatg ccaaaaacaa aaaaagcatc tcactgcaag tcacataaaa atgcaacgct  1140
gtaatatggc tgtatcagag ggctttgaaa acatacactg agctgcttct gcgctgttgt  1200
tgtccgtatt taaacaacag ctcccctgta ttccccatc tagccatttc ggaagacacc   1260
gaggaagagg aggaagatga agaccaggac tacagctttc ctatatcttc tattctagag  1320
tggtaaactc tctataagtg ttcagtgttc acatagcctt tgtgcaaaaa aaaaaaaaa   1380
aaaaaa                                                            1386
```

<210> SEQ ID NO 48
<211> LENGTH: 317
<212> TYPE: PRT
<213> ORGANISM: homo sapiens

<400> SEQUENCE: 48

```
Met Val Arg Ala Arg His Gln Pro Gly Gly Leu Cys Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
```

Gly Pro Val Cys Gly Leu Asp Gly Lys Thr Tyr Arg Asn Glu Cys Ala
            115                 120                 125
Leu Leu Lys Ala Arg Cys Lys Glu Gln Pro Glu Leu Glu Val Gln Tyr
130                 135                 140
Gln Gly Arg Cys Lys Lys Thr Cys Arg Asp Val Phe Cys Pro Gly Ser
145                 150                 155                 160
Ser Thr Cys Val Val Asp Gln Thr Asn Asn Ala Tyr Cys Val Thr Cys
                165                 170                 175
Asn Arg Ile Cys Pro Glu Pro Ala Ser Ser Glu Gln Tyr Leu Cys Gly
            180                 185                 190
Asn Asp Gly Val Thr Tyr Ser Ser Ala Cys His Leu Arg Lys Ala Thr
        195                 200                 205
Cys Leu Leu Gly Arg Ser Ile Gly Leu Ala Tyr Glu Gly Lys Cys Ile
    210                 215                 220
Lys Ala Lys Ser Cys Glu Asp Ile Gln Cys Thr Gly Gly Lys Lys Cys
225                 230                 235                 240
Leu Trp Asp Phe Lys Val Gly Arg Gly Arg Cys Ser Leu Cys Asp Glu
                245                 250                 255
Leu Cys Pro Asp Ser Lys Ser Asp Glu Pro Val Cys Ala Ser Asp Asn
            260                 265                 270
Ala Thr Tyr Ala Ser Glu Cys Ala Met Lys Glu Ala Ala Cys Ser Ser
        275                 280                 285
Gly Val Leu Leu Glu Val Lys His Ser Gly Ser Cys Asn
    290                 295                 300
                305                 310                 315

<210> SEQ ID NO 49
<211> LENGTH: 699
<212> TYPE: DNA
<213> ORGANISM: homo sapiens

<400> SEQUENCE: 49
atggagcgct gccccagcct aggggtcacc ctctacgccc tggtggtggt cctggggctg      60
cgggcgacac cggccggcgg ccagcactat ctccacatcc gccggcacc cagcgacaac     120
ctgccctgg tggacctcat cgaacaccca gaccctatct ttgaccccaa ggaaaaggat     180
ctgaacgaga gctgctgcg ctcgctgctc ggggggccact acgacccagg cttcatggcc     240
acctcgcccc ccgaggaccg gcccggcggg ggcggggtg cagctggggg cgcggaggac     300
ctggcggagc tggaccagct gctgcggcag cggccgtcgg gggccatgcc gagcgagatc     360
aaagggctag agttctccga gggcttggcc cagggcaaga agcagcgcct aagcaagaag     420
ctgcggagga agttacagat gtggctgtgg tcgcagacat tctgccccgt gctgtacgcg     480
tggaacgacc tgggcagccg cttttggccg cgctacgtga aggtgggcag ctgcttcagt     540
aagcgctcgt gctccgtgcc cgagggcatg gtgtgcaagc cgtccaagtc cgtgcacctc     600
acggtgctgc ggtggcgctg tcagcggcgc gggggccagc gctgcggctg gattcccatc     660
cagtacccca tcatttccga gtgcaagtgc tcgtgctag                             699

<210> SEQ ID NO 50
<211> LENGTH: 232
<212> TYPE: PRT
<213> ORGANISM: homo sapiens

<400> SEQUENCE: 50

Met Glu Arg Cys Pro Ser Leu Gly Val Thr Leu Tyr Ala Leu Val Val
1               5                   10                  15

Val Leu Gly Leu Arg Ala Thr Pro Ala Gly Gln His Tyr Leu His
            20                  25                  30

Ile Arg Pro Ala Pro Ser Asp Asn Leu Pro Leu Val Asp Leu Ile Glu
            35                  40                  45

His Pro Asp Pro Ile Phe Asp Pro Lys Glu Lys Asp Leu Asn Glu Thr
50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
            115                 120                 125

Leu Ala Gln Gly Lys Lys Gln Arg Leu Ser Lys Leu Arg Arg Lys
130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
            195                 200                 205

Arg Arg Gly Gly Gln Arg Cys Gly Trp Ile Pro Ile Gln Tyr Pro Ile
            210                 215                 220

Ile Ser Glu Cys Lys Cys Ser Cys
225                 230

<210> SEQ ID NO 51
<211> LENGTH: 804
<212> TYPE: DNA
<213> ORGANISM: homo sapiens

<400> SEQUENCE: 51

```
atgcatctcc tcttatttca gctgctggta ctcctgcctc taggaaagac cacacggcac      60
caggatggcc gccagaatca gagttctctt tcccccgtac tcctgccaag gaatcaaaga     120
gagcttccca caggcaacca tgaggaagct gaggagaagc cagatctgtt tgtcgcagtg     180
ccacaccttg tagccaccag ccctgcaggg gaaggccaga ggcagagaga gaagatgctg     240
tccagatttg gcaggttctg gaagaagcct gagagagaaa tgcatccatc cagggactca     300
gatagtgagc ccttcccacc tgggacccag tccctcatcc agccgataga tggaatgaaa     360
atggagaaat ctcctcttcg ggaagaagcc aagaaattct ggcaccactt catgttcaga     420
aaaactccgg cttctcaggg ggtcatcttg cccatcaaaa gccatgaagt acattgggag     480
acctgcagga cagtgccctt cagccagact ataacccacg aaggctgtga aaaagtagtt     540
gttcagaaca acctttgctt tgggaaatgc gggtctgttc attttcctgg agccgcgcag     600
cactcccata cctcctgctc tcactgtttg cctgccaagt tcaccacgat gcacttgcca     660
ctgaactgca ctgaactttc ctccgtgatc aaggtggtga tgctggtgga ggagtgccag     720
tgcaaggtga agacggagca tgaagatgga cacatcctac atgctggctc ccaggattcc     780
tttatcccag gagtttcagc ttga                                            804
```

<210> SEQ ID NO 52
<211> LENGTH: 267
<212> TYPE: PRT
<213> ORGANISM: homo sapiens

<400> SEQUENCE: 52

```
Met His Leu Leu Leu Phe Gln Leu Leu Val Leu Leu Pro Leu Gly Lys
1               5                   10                  15
Thr Thr Arg His Gln Asp Gly Arg Gln Asn Gln Ser Ser Leu Ser Pro
            20                  25                  30
Val Leu Leu Pro Arg Asn Gln Arg Glu Leu Pro Thr Gly Asn His Glu
        35                  40                  45
Glu Ala Glu Glu Lys Pro Asp Leu Phe Val Ala Val Pro His Leu Val
    50                  55                  60
Ala Thr Ser Pro Ala Gly Glu Gly Gln Arg Gln Arg Glu Lys Met Leu
65                  70                  75                  80
Ser Arg Phe Gly Arg Phe Trp Lys Lys Pro Glu Arg Glu Met His Pro
                85                  90                  95
Ser Arg Asp Ser Asp Ser Glu Pro Phe Pro Pro Gly Thr Gln Ser Leu
            100                 105                 110
Ile Gln Pro Ile Asp Gly Met Lys Met Glu Lys Ser Pro Leu Arg Glu
        115                 120                 125
Glu Ala Lys Lys Phe Trp His His Phe Met Phe Arg Lys Thr Pro Ala
    130                 135                 140
Ser Gln Gly Val Ile Leu Pro Ile Lys Ser His Glu Val His Trp Glu
145                 150                 155                 160
Thr Cys Arg Thr Val Pro Phe Ser Gln Thr Ile Thr His Glu Gly Cys
                165                 170                 175
Glu Lys Val Val Val Gln Asn Asn Leu Cys Phe Gly Lys Cys Gly Ser
            180                 185                 190
Val His Phe Pro Gly Ala Ala Gln His Ser His Thr Ser Cys Ser His
        195                 200                 205
Cys Leu Pro Ala Lys Phe Thr Thr Met His Leu Pro Leu Asn Cys Thr
    210                 215                 220
Glu Leu Ser Ser Val Ile Lys Val Val Met Leu Val Glu Glu Cys Gln
225                 230                 235                 240
Cys Lys Val Lys Thr Glu His Glu Asp Gly His Ile Leu His Ala Gly
                245                 250                 255
Ser Gln Asp Ser Phe Ile Pro Gly Val Ser Ala
            260                 265
```

<210> SEQ ID NO 53
<211> LENGTH: 1523
<212> TYPE: DNA
<213> ORGANISM: homo sapiens

<400> SEQUENCE: 53

```
ctggcgcggg cgggagctgc ggcggatacc cttgcgtgct gtggagaccc tactctcttc      60
gctgagaacg gccgctagcg gggactgaag gccgggagcc cactcccgac ccggggctag     120
cgtgcgtccc tagagtcgag cggggcaagg gagccagtgg ccgccgacgg gggaccggga     180
aacttttctg ggctcctggg cgcgcccgt agccgcgctc catgctccgg cagcggcccg      240
aaacccagcc ccgccgctga cggcgcccgc cgctccgggc agggcccatg ccctgcgcgc     300
tccggggtc gtaggctgcc gccgagccgg ggctccggaa gccggcgggg gcgccgcggc      360
cgtgcgggc gtcaatggat cgccactcca gctacatctt catctggctg cagctggagc      420
```

```
tctgcgccat ggccgtgctg ctcaccaaag gtgaaattcg atgctactgt gatgctgccc      480
actgtgtagc cactggttat atgtgtaaat ctgagctcag cgcctgcttc tctagacttc      540
ttgatcctca gaactcaaat tccccactca cccatggctg cctggactct cttgcaagca      600
cgacagacat ctgccaagcc aaacaggccc gaaaccactc tggcaccacc atacccacat      660
tggaatgctg tcatgaagac atgtgcaatt acagagggct gcacgatgtt ctctctcctc      720
ccaggggtga ggcctcagga caaggaaaca ggtatcagca tgatggtagc agaaaccttca      780 tcaccaaggt gcaggagctg acttcttcca agagttgtg gttccgggca gcggtcattg      840
ccgtgcccat tgctggaggg ctgatttttag tgttgcttat tatgttggcc ctgaggatgc      900
ttcgaagtga aaataagagg ctgcaggatc agcggcaaca gatgctctcc cgtttgcact      960
acagctttca cggacaccat tccaaaaagg ggcaggttgc aaagttagac ttggaatgca     1020
tggtgccggt cagtgggcac gagaactgct gtctgacctg tgataaaatg agacaagcag     1080
acctcagcaa cgataagatc ctctcgcttg ttcactgggg catgtacagt gggcacggga     1140
agctggaatt cgtatgacgg agtcttatct gaactacact tactgaacag cttgaaggcc     1200
ttttgagttc tgctggacag gagcacttta tctgaagaca aactcattta atcatctttg     1260
agagacaaaa tgacctctgc aaacagaatc ttggatattt cttctgaagg attatttgca     1320
cagacttaaa tacagttaaa tgtgttattt gcttttaaaa ttataaaaag caaagagaag     1380
actttgtaca cactgtcacc agggttattt gcatccaagg gagctggaat tgagtaccta     1440
aataaacaaa aatgtgccct atgtaagctt ctacatcttg atttattgta aagatttaaa     1500
agaaatatat atattttgtc tga                                             1523

<210> SEQ ID NO 54
<211> LENGTH: 260
<212> TYPE: PRT
<213> ORGANISM: homo sapiens

<400> SEQUENCE: 54

Met Asp Arg His Ser Ser Tyr Ile Phe Ile Trp Leu Gln Leu Glu Leu
1               5                   10                  15

Cys Ala Met Ala Val Leu Leu Thr Lys Gly Glu Ile Arg Cys Tyr Cys
                20                  25                  30

Asp Ala Ala His Cys Val Ala Thr Gly Tyr Met Cys Lys Ser Glu Leu
            35                  40                  45

Ser Ala Cys Phe Ser Arg Leu Leu Asp Pro Gln Asn Ser Asn Ser Pro
        50                  55                  60

Leu Thr His Gly Cys Leu Asp Ser Leu Ala Ser Thr Thr Asp Ile Cys
65                  70                  75                  80

Gln Ala Lys Gln Ala Arg Asn His Ser Gly Thr Thr Ile Pro Thr Leu
                85                  90                  95

Glu Cys Cys His Glu Asp Met Cys Asn Tyr Arg Gly Leu His Asp Val
            100                 105                 110

Leu Ser Pro Pro Arg Gly Glu Ala Ser Gly Gln Gly Asn Arg Tyr Gln
        115                 120                 125

His Asp Gly Ser Arg Asn Leu Ile Thr Lys Val Gln Glu Leu Thr Ser
    130                 135                 140

Ser Lys Glu Leu Trp Phe Arg Ala Ala Val Ile Ala Val Pro Ile Ala
145                 150                 155                 160

Gly Gly Leu Ile Leu Val Leu Leu Ile Met Leu Ala Leu Arg Met Leu
                165                 170                 175

Arg Ser Glu Asn Lys Arg Leu Gln Asp Gln Arg Gln Gln Met Leu Ser
```

```
                   180               185               190
Arg Leu His Tyr Ser Phe His Gly His His Ser Lys Lys Gly Gln Val
        195               200               205

Ala Lys Leu Asp Leu Glu Cys Met Val Pro Val Ser Gly His Glu Asn
        210               215               220

Cys Cys Leu Thr Cys Asp Lys Met Arg Gln Ala Asp Leu Ser Asn Asp
225               230               235               240

Lys Ile Leu Ser Leu Val His Trp Gly Met Tyr Ser Gly His Gly Lys
                245               250               255

Leu Glu Phe Val
        260

<210> SEQ ID NO 55
<211> LENGTH: 23
<212> TYPE: DNA
<213> ORGANISM: Artificial
<220> FEATURE:
<223> OTHER INFORMATION: Synthetic primer

<400> SEQUENCE: 55
aggccaaccg cgagaagatg acc                                      23

<210> SEQ ID NO 56
<211> LENGTH: 22
<212> TYPE: DNA
<213> ORGANISM: Artificial
<220> FEATURE:
<223> OTHER INFORMATION: Synthetic primer

<400> SEQUENCE: 56
gaagtccagg gcgacgtagc ac                                       22
```